(12) United States Patent
Zhang et al.

(10) Patent No.: US 12,152,071 B2
(45) Date of Patent: *Nov. 26, 2024

(54) EGFL6 SPECIFIC MONOCLONAL ANTIBODIES AND METHODS OF THEIR USE

(71) Applicant: THE BOARD OF REGENTS OF THE UNIVERSITY OF TEXAS SYSTEM, Austin, TX (US)

(72) Inventors: Ningyan Zhang, Pearland, TX (US); Zhiqiang An, Pearland, TX (US); Anil K. Sood, Pearland, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 314 days.

This patent is subject to a terminal disclaimer.

(21) Appl. No.: 17/096,280

(22) Filed: Nov. 12, 2020

(65) Prior Publication Data

US 2021/0130450 A1    May 6, 2021

Related U.S. Application Data

(63) Continuation of application No. 16/075,711, filed as application No. PCT/US2017/016659 on Feb. 6, 2017, now Pat. No. 10,875,912.

(60) Provisional application No. 62/291,987, filed on Feb. 5, 2016.

(51) Int. Cl.
| | |
|---|---|
| *C07K 16/22* | (2006.01) |
| *A61K 9/00* | (2006.01) |
| *A61K 39/00* | (2006.01) |
| *A61P 35/00* | (2006.01) |
| *C12N 15/113* | (2010.01) |
| *G01N 33/574* | (2006.01) |

(52) U.S. Cl.
CPC ............ *C07K 16/22* (2013.01); *A61K 9/0019* (2013.01); *A61P 35/00* (2018.01); *C12N 15/1136* (2013.01); *G01N 33/57449* (2013.01); *A61K 2039/505* (2013.01); *C07K 2317/24* (2013.01); *C07K 2317/565* (2013.01); *C07K 2317/76* (2013.01); *C07K 2317/92* (2013.01); *C12N 2310/14* (2013.01); *G01N 2333/485* (2013.01)

(58) Field of Classification Search
None
See application file for complete search history.

(56) References Cited

U.S. PATENT DOCUMENTS

| | | | |
|---|---|---|---|
| 10,875,912 B2 * | 12/2020 | Zhang | .................. A61K 9/0019 |
| 2003/0036508 A1 | 2/2003 | Ford et al. | |
| 2008/0138894 A1 | 6/2008 | Maertens et al. | |
| 2010/0119550 A1 | 5/2010 | Gomi et al. | |
| 2012/0014958 A1 | 1/2012 | Borras et al. | |
| 2013/0129735 A1 | 5/2013 | Ye et al. | |
| 2013/0129765 A1 | 5/2013 | Murphy et al. | |
| 2015/0037349 A1 | 2/2015 | Castanheira Aires da Silva et al. | |

FOREIGN PATENT DOCUMENTS

| | | |
|---|---|---|
| WO | WO 2002/30977 | 4/2002 |
| WO | WO 2014/150720 A1 | 9/2014 |
| WO | WO 2014/190273 A1 | 11/2014 |

OTHER PUBLICATIONS

Kang et al., Int J Med Sci, 17(10):1320-26, 2020.*
Su et al., Int J Clin Exp Pathol 15(11):436-443, 2022.*
Adamczyk, et al., Surface Plasmon Resonance (SPR) as a Tool for Antibody Conjugate Analysis, Bioconjugate Chem., 10:1032-1037, 1999.
Chim, Shek Man, et al. "EGFL6 promotes endothelial cell migration and angiogenesis through the activation of extracellular signal-regulated kinase." *Journal of Biological Chemistry* 286.25 (2011): 22035-22046.
International Search Report + Written Opinion for PCT/US17/16659, mailed on Jul. 10, 2017.
Office Communication issued in Russian Application No. 2018131611, dated Mar. 23, 2021. Original and English Translation.
Office Communication issued in Russian Application No. 2018131611, dated May 19, 2020. Original and English Translation.
Partial Supplementary European Search Report issued in European Application No. 17748334.4, dated Jul. 24, 2019.
Rudikoff et al., "Single amino acid substitution altering antigen-binding specificity", *Immunology*, vol. 79, Mar. 1982, pp. 1979-1983.
Yarilin A. A., *Osnovy immunologii*: Textbook.—M.: Medicine, 1999, 608 pages; p. 171, the second paragraph, pp. 172-173. Russian Original.
Yarilin A. A., *Osnovy immunologii*: Textbook.—M.: Medicine, 1999, 608 pages; p. 171, the second paragraph, pp. 172-173. English Translation.
Office Communication issued in Chinese Application No. 202110985801.8, dated Aug. 23, 2023. English Translation.

* cited by examiner

*Primary Examiner* — Marianne P Allen
(74) *Attorney, Agent, or Firm* — Parker Highlander PLLC

(57) ABSTRACT

Isolated or recombinant anti-EGFL6 monoclonal antibodies are provided. In some cases, antibodies of the embodiments can be used for the detection, diagnosis and/or therapeutic treatment of human diseases, such as cancer.

5 Claims, 30 Drawing Sheets

Specification includes a Sequence Listing.

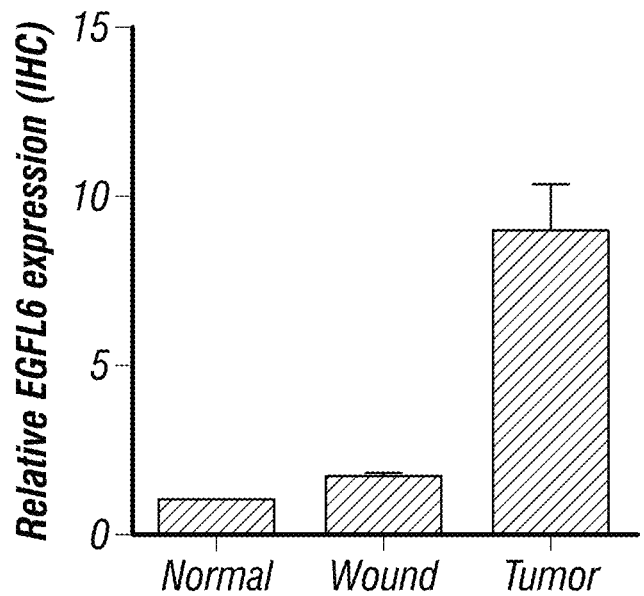
EGFL6
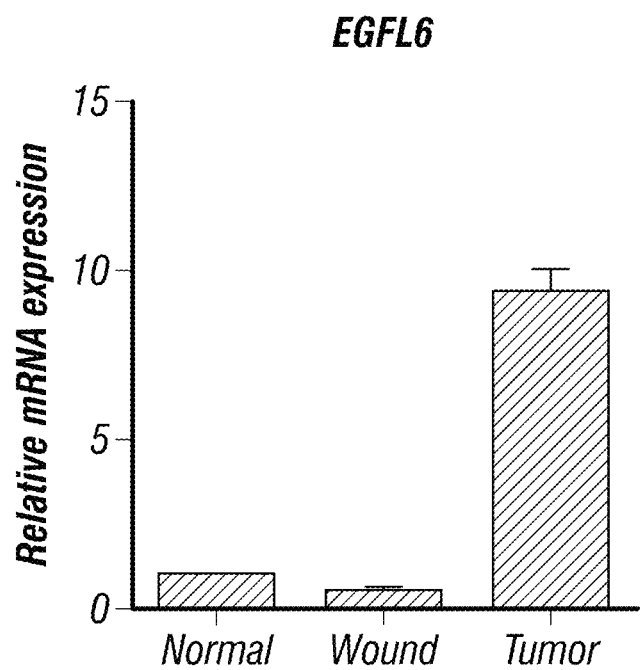
FIG. 4D

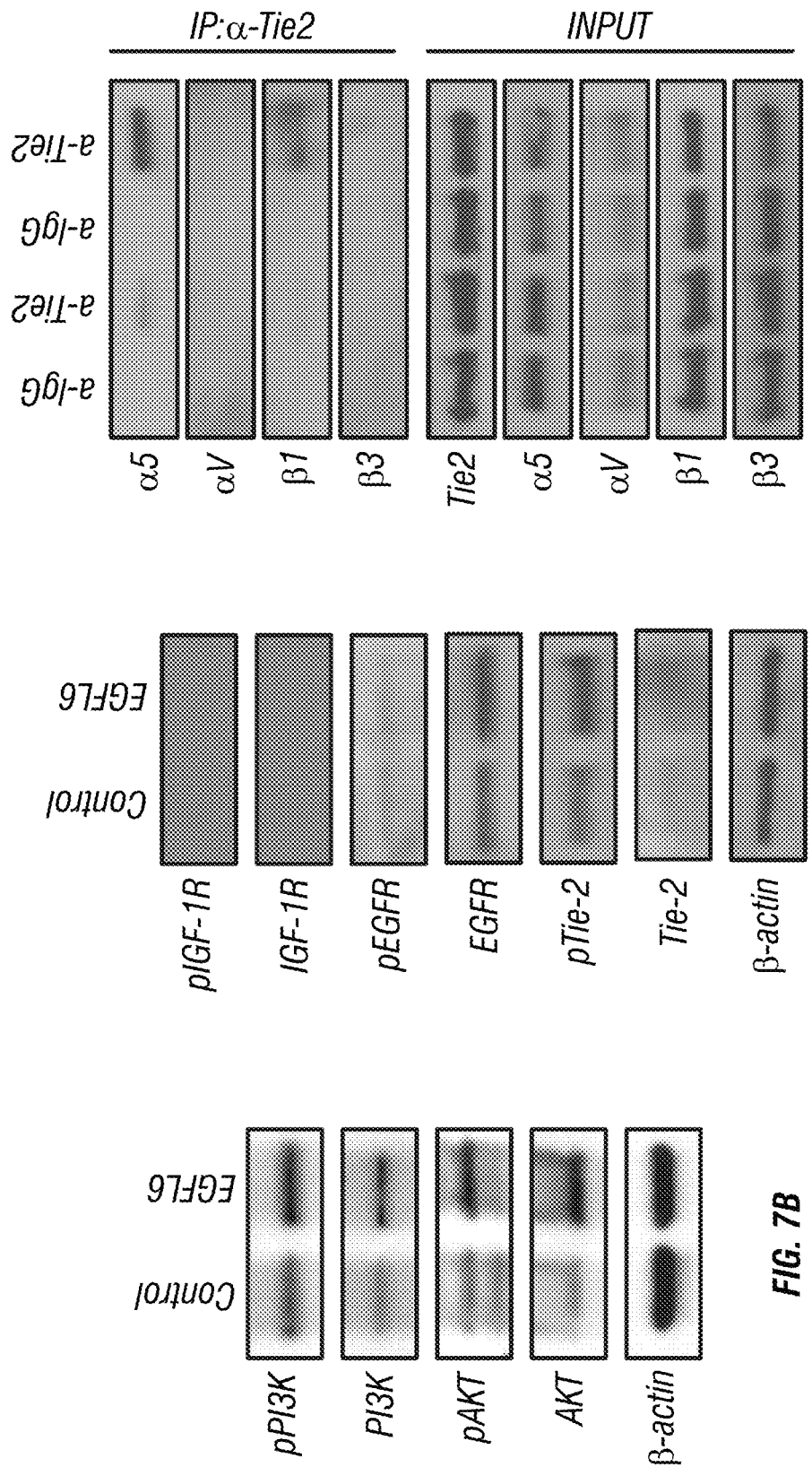

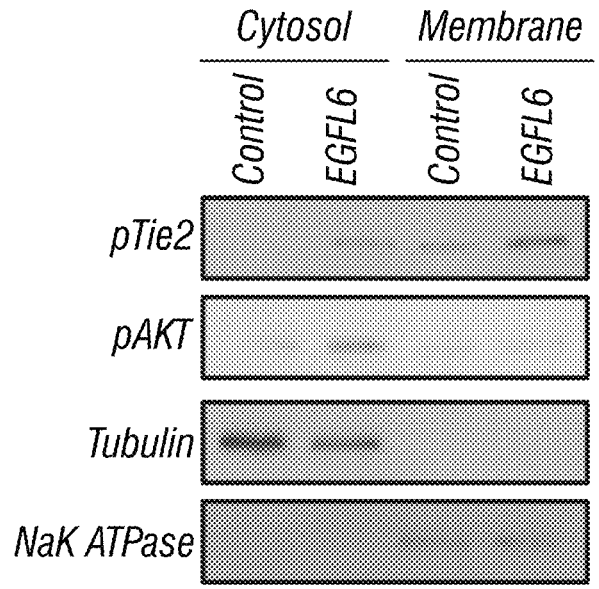
FIG. 7E
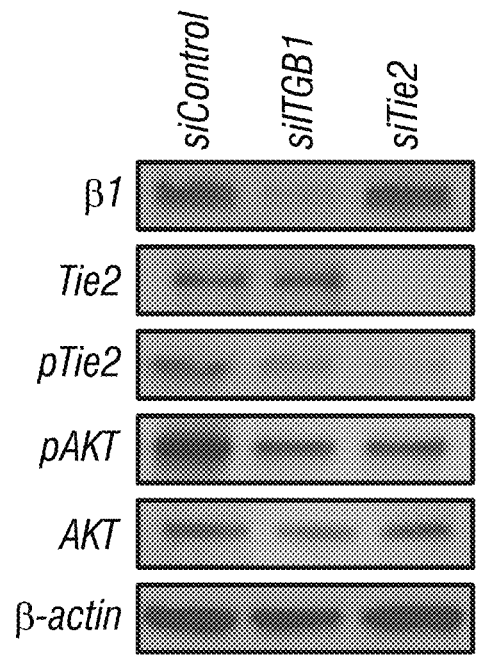
FIG. 7F
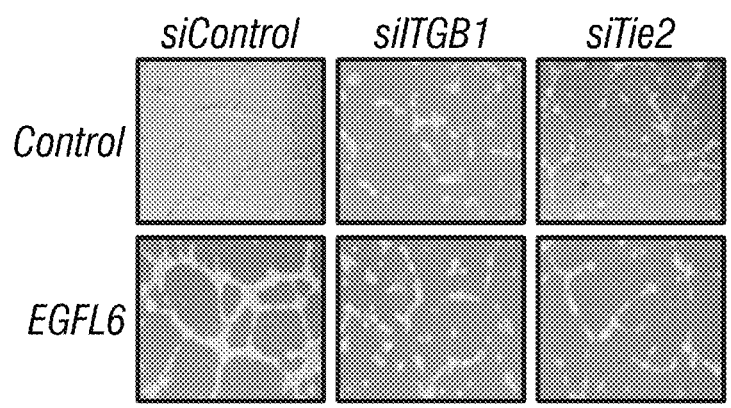
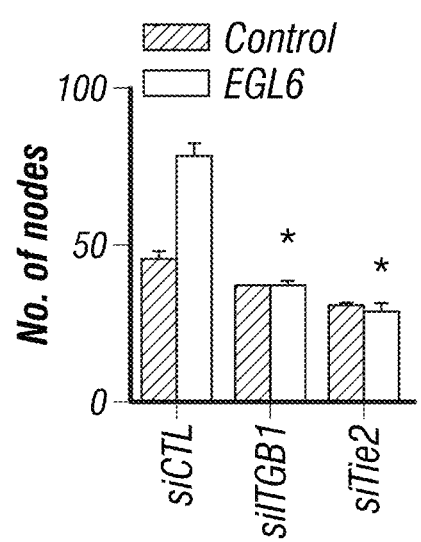
FIG. 7G

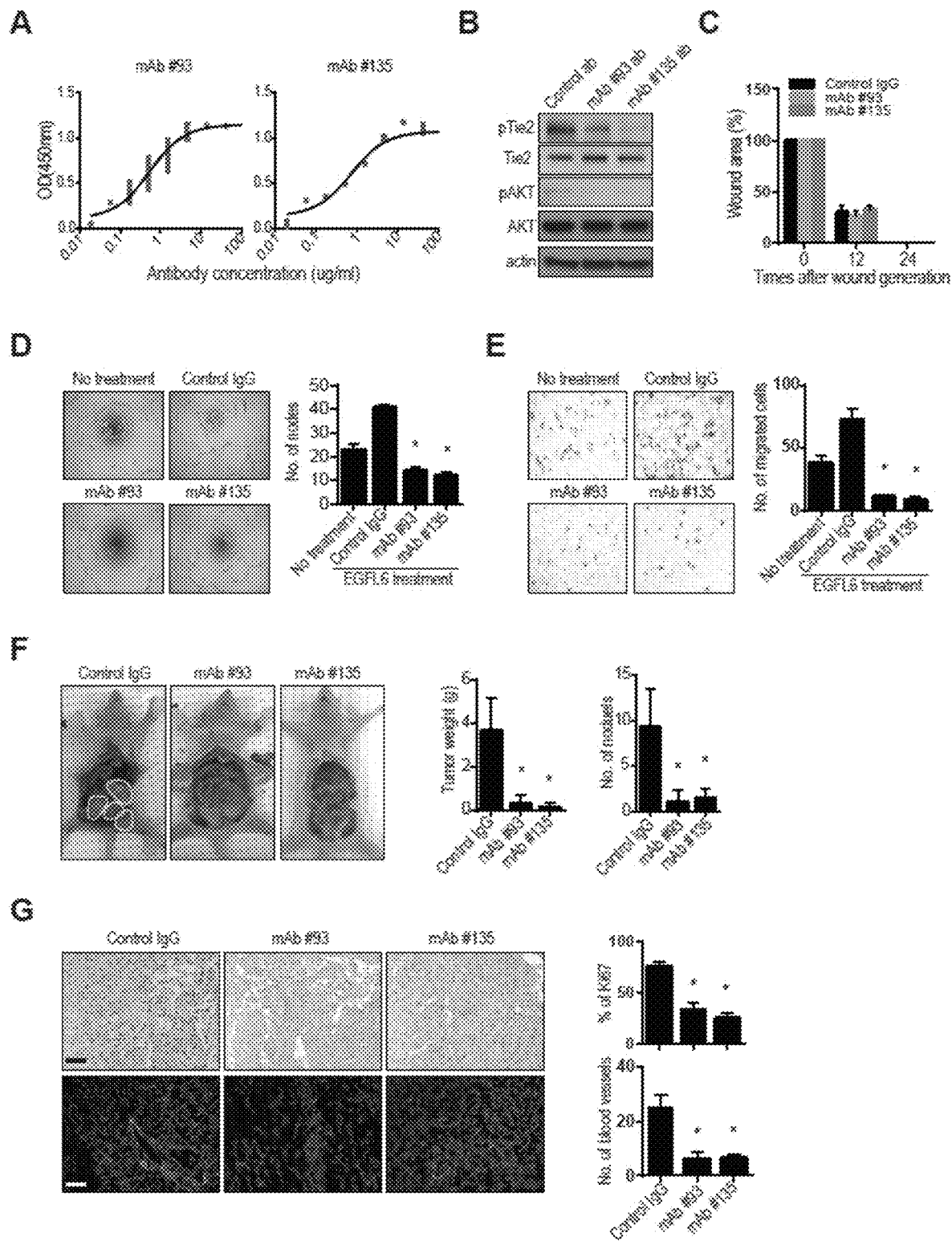
FIGS. 8A-G

A
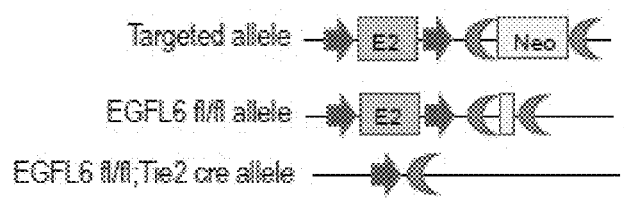
B EC isolation using CD31 bead
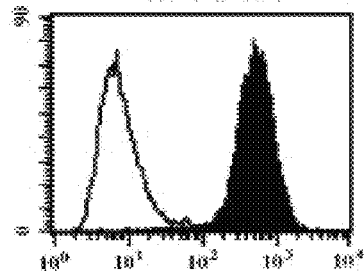
C
RNA level in EC
FIGS. 9A-C

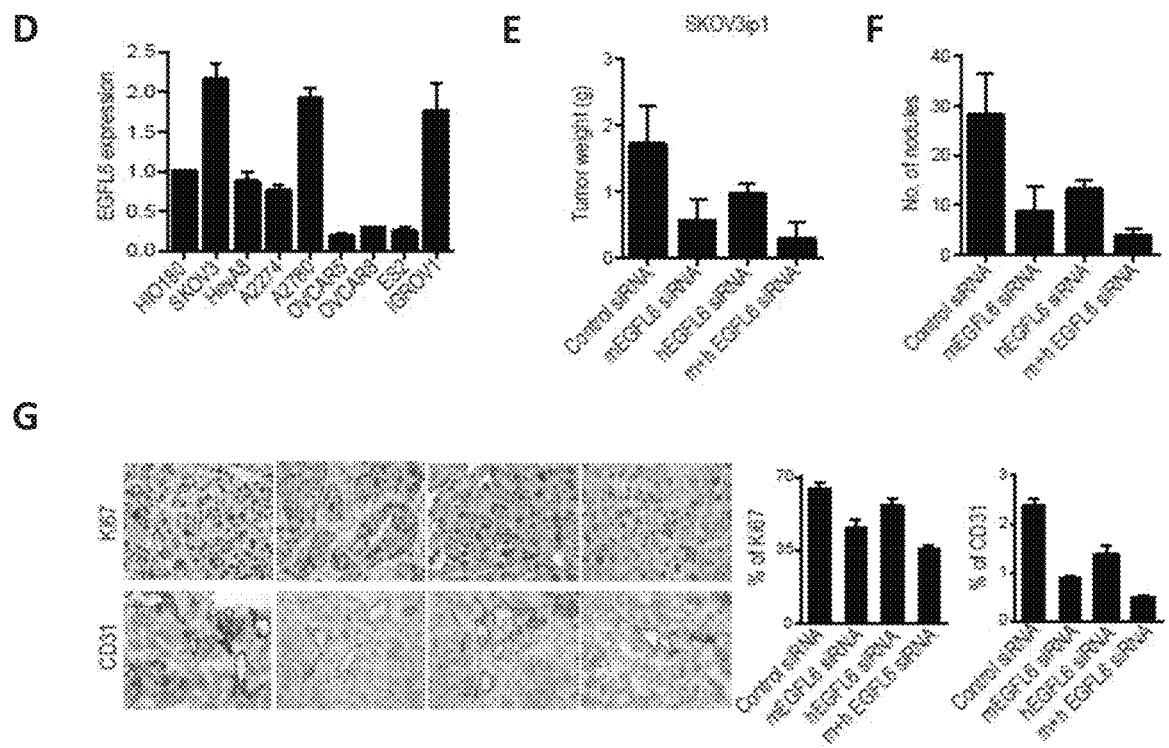
FIGS. 9D-G

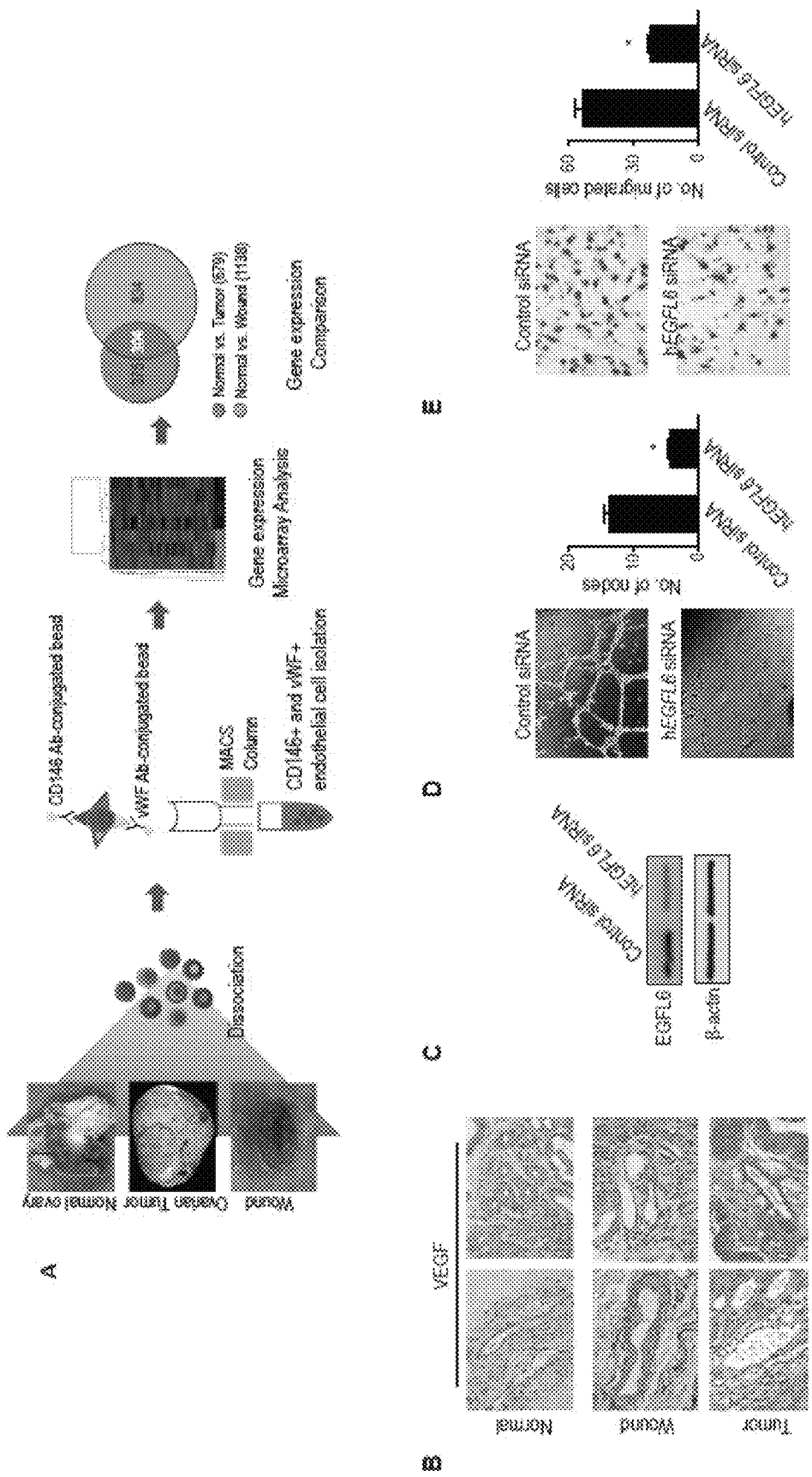
FIGS. 10A-E

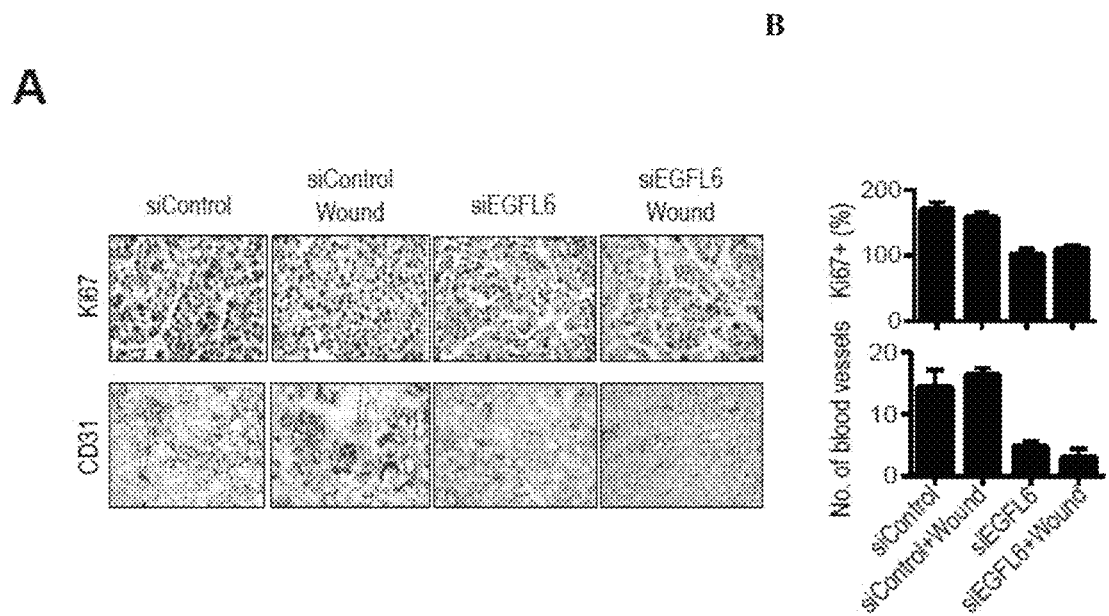
FIGS. 11A-B

EGFL6 SPECIFIC MONOCLONAL ANTIBODIES AND METHODS OF THEIR USE

This application is a continuation of U.S. patent application Ser. No. 16/075,711, filed Aug. 6, 2018, as a national phase application under 35 U.S.C. § 371 of International Application No. PCT/US2017/016659, filed Feb. 6, 2017, which claims the benefit of U.S. Provisional Patent Application No. 62/291,987, filed Feb. 5, 2016, the entirety of each of which is incorporated herein by reference.

The instant application contains a Sequence Listing, which has been submitted in ASCII format on Jan. 25, 2021, and is hereby incorporated by reference in its entirety. Said ASCII copy, created on Dec. 10, 2020, is named UTSHP0324USC1_updated_ST25.txt and is 67,512 bytes in size.

BACKGROUND OF THE INVENTION

1. Field of the Invention

The present invention relates generally to the field of cancer biology. More particularly, it concerns EGFL6 targeting monoclonal antibodies for the treatment and detection of cancer.

2. Description of Related Art

Human epidermal growth factor (EGF)-like domain multiple 6 (EGFL6) was first discovered in tumors and fetal tissues and is a member of the EGF repeat superfamily. EGFL6 was identified as a secreted protein with four and one-half EGF-like repeat domains, two N-linked glycosylation sites, one integrin association motif (RGD), a tyrosine phosphorylation site, and a MAM domain (Yeung et al., 1999). Studies have shown that high expression of EGFL6 is associated with tumor tissues in certain cancer types such as ovarian cancer and lung cancer, while limited expression was found in healthy adult tissue (Buckanovich et al., 2007; Chim et al., 2011; and Oberauer et al., 2010). However, there remains a need for reagents and the therapeutics for the treatment of EGFL6-posative cancers.

SUMMARY OF THE INVENTION

Described herein are EGFL6 monoclonal antibodies that bind to EGFL6. In further aspects, provided EGFL6-binding antibodies reduce EGFL6 signaling and can be used to inhibit cancer cell proliferation. Thus, in a first embodiment, there is provided an isolated or recombinant monoclonal antibody that specifically binds to an EGFL6. In certain aspects, an antibody that competes for the binding of an EGFL6 with the E1-33, E1-34, E1-80, E1-89, E2-93, E1-38, E1-52, E2-36, E1-95, E2-116, E2-135, or E1-142 monoclonal antibody is provided. In certain aspects, the antibody may comprise all or part of the heavy chain variable region and/or light chain variable region of the E1-33, E1-34, E1-80, E1-89, E2-93, E1-38, E1-52, E2-36, E1-95, E2-116, E2-135, or E1-142 monoclonal antibodies. In a further aspect, the antibody may comprise an amino acid sequence that corresponds to a first, second, and/or third complementarity determining region (CDR) from the light variable and/or heavy variable chain of the E1-33, E1-34, E1-80, E1-89, E2-93, E1-38, E1-52, E2-36, E1-95, E2-116, E2-135, or E1-142 monoclonal antibodies of the present embodiments.

In certain aspects, the isolated antibody comprises CDR sequences at least 80%, 85%, 90%, 91%, 92%, 93%, 94%, 95%, 96%, 97%, 98%, 99% or 100% identical to the CDR regions of the E1-33, E1-34, E1-80, E1-89, E2-93, E1-38, E1-52, E2-36, E1-95, E2-116, E2-135, or E1-142 heavy and light chain amino acid sequences. In further aspects, an antibody comprises CDR regions identical to the E1-33, E1-34, E1-80, E1-89, E2-93, E1-38, E1-52, E2-36, E1-95, E2-116, E2-135, or E1-142 CDR regions, except for one or two amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a E1-33, E1-34, E1-80, E1-89, E2-93, E1-38, E1-52, E2-36, E1-95, E2-116, E2-135, or E1-142 monoclonal antibody. Thus, in some specific aspects, an antibody of the embodiments comprises (a) a first $V_H$ CDR at least 80%, 85%, 90%, 91%, 92%, 93%, 94%, 95%, 96%, 97%, 98%, 99% or 100% identical to $V_H$ CDR1 of E1-33 (SEQ ID NO: 4), E1-34 (SEQ ID NO: 10), E1-80 (SEQ ID NO: 16), E1-89 (SEQ ID NO: 22), E2-93 (SEQ ID NO: 28), E1-38 (SEQ ID NO: 34), E1-52 (SEQ ID NO: 40), E2-36 (SEQ ID NO: 46), E1-95 (SEQ ID NO: 52), E2-116 (SEQ ID NO: 58), E2-135 (SEQ ID NO: 64), or E1-142 (SEQ ID NO: 70); (b) a second $V_H$ CDR at least 80%, 85%, 90%, 91%, 92%, 93%, 94%, 95%, 96%, 97%, 98%, 99% or 100% identical to $V_H$ CDR2 of E1-33 (SEQ ID NO: 5), E1-34 (SEQ ID NO: 11), E1-80 (SEQ ID NO: 17), E1-89 (SEQ ID NO: 23), E2-93 (SEQ ID NO: 29), E1-38 (SEQ ID NO: 35), E1-52 (SEQ ID NO: 41), E2-36 (SEQ ID NO: 47), E1-95 (SEQ ID NO: 53), E2-116 (SEQ ID NO: 59), E2-135 (SEQ ID NO: 65), or E1-142 (SEQ ID NO: 71); (c) a third $V_H$ CDR at least 80%, 85%, 90%, 91%, 92%, 93%, 94%, 95%, 96%, 97%, 98%, 99% or 100% identical to $V_H$ CDR3 of E1-33 (SEQ ID NO: 6), E1-34 (SEQ ID NO: 12), E1-80 (SEQ ID NO: 18), E1-89 (SEQ ID NO: 24), E2-93 (SEQ ID NO: 30), E1-38 (SEQ ID NO: 36), E1-52 (SEQ ID NO: 42), E2-36 (SEQ ID NO: 48), E1-95 (SEQ ID NO: 54), E2-116 (SEQ ID NO: 60), E2-135 (SEQ ID NO: 66), or E1-142 (SEQ ID NO: 72); (d) a first $V_L$ CDR at least 80%, 85%, 90%, 91%, 92%, 93%, 94%, 95%, 96%, 97%, 98%, 99% or 100% identical to $V_L$ CDR1 of E1-33 (SEQ ID NO: 76), E1-34 (SEQ ID NO: 82), E1-80 (SEQ ID NO: 88), E1-89 (SEQ ID NO: 93), E2-93 (SEQ ID NO: 99), E1-38 (SEQ ID NO: 104), E1-52 (SEQ ID NO: 108), E2-36 (SEQ ID NO: 113), E1-95 (SEQ ID NO: 117), E2-116 (SEQ ID NO: 121), E2-135 (SEQ ID NO: 126), or E1-142 (SEQ ID NO: 131); (e) a second $V_L$ CDR at least 80%, 85%, 90%, 91%, 92%, 93%, 94%, 95%, 96%, 97%, 98%, 99% or 100% identical to $V_L$ CDR2 of E1-33 (SEQ ID NO: 77), E1-34 (SEQ ID NO: 83), E1-80 (SEQ ID NO: 77), E1-89 (SEQ ID NO: 94), E2-93 (SEQ ID NO: 100), E1-38 (SEQ ID NO: 100), E1-52 (SEQ ID NO: 77), E2-36 (SEQ ID NO: 83), E1-95 (SEQ ID NO: 83), E2-116 (SEQ ID NO: 100), E2-135 (SEQ ID NO: 127), or E1-142 (SEQ ID NO: 100); and (f) a third $V_L$ CDR at least 80%, 85%, 90%, 91%, 92%, 93%, 94%, 95%, 96%, 97%, 98%, 99% or 100% identical to $V_L$ CDR3 of E1-33 (SEQ ID NO: 78), E1-34 (SEQ ID NO: 84), E1-80 (SEQ ID NO: 89), E1-89 (SEQ ID NO: 95), E2-93 (SEQ ID NO: 101), E1-38 (SEQ ID NO: 105), E1-52 (SEQ ID NO: 109), E2-36 (SEQ ID NO: 114), E1-95 (SEQ ID NO: 118), E2-116 (SEQ ID NO: 122), E2-135 (SEQ ID NO: 128), or E1-142 (SEQ ID NO: 132).

In certain aspects, such an antibody is a humanized or de-immunized antibody comprising the foregoing CDRs on a human IgGs (e.g., IgG1, IgG2, IgG4, or a genetically modified IgG) backbone.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-33, which are represented by SEQ ID NOs: 4, 5, 6, 76, 77, and 78, respectively. In one aspect, the isolated antibody comprises CDR sequences that are identical to the CDR sequences of monoclonal antibody E1-33.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-33 (SEQ ID NO: 157) or the humanized $V_H$ domain of E1-33 mAB; and a $V_L$ domain at least about 80%, 85%, 90%, 91%, 92%, 93%, 94%, 95%, 96%, 97%, 98%, 99% or 100% identical to the $V_L$ domain of E1-33 (SEQ ID NO: 158) or the humanized $V_L$ domain of E1-33 mAB. For example, the antibody can comprise a $V_H$ domain at least 95% identical to the $V_H$ domain of the humanized E1-33 mAB and a $V_L$ domain at least 95% identical to the $V_L$ domain of the humanized E1-33 mAB. Thus, in some aspects, an antibody comprises a $V_H$ domain identical to the $V_H$ domain of humanized E1-33 mAB and a $V_L$ domain identical to the $V_L$ domain of the humanized E1-33 mAB. In a specific example, the isolated antibody can comprise $V_H$ and $V_L$ domains identical to those of monoclonal antibody E1-33.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-34, which are represented by SEQ ID NOs: 10, 11, 12, 82, 83, and 84, respectively. In one aspect, the isolated antibody comprises CDR sequences that are identical to the CDR sequences of monoclonal antibody E1-34.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-34 (SEQ ID NO: 159) or the humanized $V_H$ domain of E1-34 mAB; and a $V_L$ domain at least about 80%, 85%, 90%, 91%, 92%, 93%, 94%, 95%, 96%, 97%, 98%, 99% or 100% identical to the $V_L$ domain of E1-34 (SEQ ID NO: 160) or the humanized $V_L$ domain of E1-34 mAB. For example, the antibody can comprise a $V_H$ domain at least 95% identical to the $V_H$ domain of the humanized E1-34 mAB and a $V_L$ domain at least 95% identical to the $V_L$ domain of the humanized E1-34 mAB. Thus, in some aspects, an antibody comprises a $V_H$ domain identical to the $V_H$ domain of humanized E1-34 mAB and a $V_L$ domain identical to the $V_L$ domain of the humanized E1-34 mAB. In a specific example, the isolated antibody can comprise $V_H$ and $V_L$ domains identical to those of monoclonal antibody E1-34.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-80, which are represented by SEQ ID NOs: 16, 17, 18, 88, 77, and 89, respectively. In one aspect, the isolated antibody comprises CDR sequences that are identical to the CDR sequences of monoclonal antibody E1-80.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-80 (SEQ ID NO: 161) or the humanized $V_H$ domain of E1-80 mAB; and a $V_L$ domain at least about 80%, 85%, 90%, 91%, 92%, 93%, 94%, 95%, 96%, 97%, 98%, 99% or 100% identical to the $V_L$ domain of E1-80 (SEQ ID NO: 162) or the humanized $V_L$ domain of E1-80 mAB. For example, the antibody can comprise a $V_H$ domain at least 95% identical to the $V_H$ domain of the humanized E1-80 mAB and a $V_L$ domain at least 95% identical to the $V_L$ domain of the humanized E1-80 mAB. Thus, in some aspects, an antibody comprises a $V_H$ domain identical to the $V_H$ domain of humanized E1-80 mAB and a $V_L$ domain identical to the $V_L$ domain of the humanized E1-80 mAB. In a specific example, the isolated antibody can comprise $V_H$ and $V_L$ domains identical to those of monoclonal antibody E1-80.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-89, which are represented by SEQ ID NOs: 22, 23, 24, 93, 94, and 95, respectively. In one aspect, the isolated antibody comprises CDR sequences that are identical to the CDR sequences of monoclonal antibody E1-89.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-89 (SEQ ID NO: 163) or the humanized $V_H$ domain of E1-89 mAB; and a $V_L$ domain at least about 80%, 85%, 90%, 91%, 92%, 93%, 94%, 95%, 96%, 97%, 98%, 99% or 100% identical to the $V_L$ domain of E1-89 (SEQ ID NO: 164) or the humanized $V_L$ domain of E1-89 mAB. For example, the antibody can comprise a $V_H$ domain at least 95% identical to the $V_H$ domain of the humanized E1-89 mAB and a $V_L$ domain at least 95% identical to the $V_L$ domain of the humanized E1-89 mAB. Thus, in some aspects, an antibody comprises a $V_H$ domain identical to the $V_H$ domain of humanized E1-89 mAB and a $V_L$ domain identical to the $V_L$ domain of the humanized E1-89 mAB. In a specific example, the isolated antibody can comprise $V_H$ and $V_L$ domains identical to those of monoclonal antibody E1-89.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E2-93, which are represented by SEQ ID NOs: 28, 29, 30, 99, 100, and 101, respectively. In one aspect, the isolated antibody comprises CDR sequences that are identical to the CDR sequences of monoclonal antibody E2-93.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E2-93 (SEQ ID NO: 165) or the humanized $V_H$ domain of E2-93 mAB; and a $V_L$ domain at least about 80%, 85%, 90%, 91%, 92%, 93%, 94%, 95%, 96%, 97%, 98%, 99% or 100% identical to the $V_L$ domain of E2-93 (SEQ ID NO: 166) or the humanized $V_L$ domain of E2-93 mAB. For example, the antibody can comprise a $V_H$ domain at least 95% identical to the $V_H$ domain of the humanized E2-93 mAB and a $V_L$ domain at least 95% identical to the $V_L$ domain of the humanized E2-93 mAB. Thus, in some aspects, an antibody comprises a $V_H$ domain identical to the $V_H$ domain of humanized E2-93 mAB and a $V_L$ domain identical to the $V_L$ domain of the humanized E2-93 mAB. In a specific example, the isolated antibody can comprise $V_H$ and $V_L$ domains identical to those of monoclonal antibody E2-93.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-38, which are represented by SEQ ID NOs: 34, 35, 36, 104, 100, and 105, respectively. In one aspect, the isolated antibody comprises CDR sequences that are identical to the CDR sequences of monoclonal antibody E1-38.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-38 (SEQ ID NO: 167) or the humanized $V_H$ domain of E1-38 mAB; and a $V_L$ domain at least about 80%, 85%, 90%, 91%, 92%, 93%, 94%, 95%, 96%, 97%, 98%, 99% or 100% identical to the $V_L$ domain of E1-38 (SEQ ID NO: 168) or the humanized $V_L$ domain of E1-38 mAB. For example, the antibody can comprise a $V_H$ domain at least 95% identical to the $V_H$ domain of the humanized E1-38 mAB and a $V_L$ domain at least 95% identical to the $V_L$ domain of the humanized E1-38 mAB. Thus, in some aspects, an antibody comprises a $V_H$ domain identical to the $V_H$ domain of humanized E1-38 mAB and a $V_L$ domain identical to the $V_L$ domain of the humanized E1-38 mAB. In a specific example, the isolated antibody can comprise $V_H$ and $V_L$ domains identical to those of monoclonal antibody E1-38.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-52, which are represented by SEQ ID NOs: 40, 41, 42, 108, 77, and 109, respectively. In one aspect, the isolated antibody comprises CDR sequences that are identical to the CDR sequences of monoclonal antibody E1-52.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-52 (SEQ ID NO: 169) or the humanized $V_H$ domain of E1-52 mAB; and a $V_L$ domain at least about 80%, 85%, 90%, 91%, 92%, 93%, 94%, 95%, 96%, 97%, 98%, 99% or 100% identical to the $V_L$ domain of E1-52 (SEQ ID NO: 170) or the humanized $V_L$ domain of E1-52 mAB. For example, the antibody can comprise a $V_H$ domain at least 95% identical to the $V_H$ domain of the humanized E1-52 mAB and a $V_L$ domain at least 95% identical to the $V_L$ domain of the humanized E1-52 mAB. Thus, in some aspects, an antibody comprises a $V_H$ domain identical to the $V_H$ domain of humanized E1-52 mAB and a $V_L$ domain identical to the $V_L$ domain of the humanized E1-52 mAB. In a specific example, the isolated antibody can comprise $V_H$ and $V_L$ domains identical to those of monoclonal antibody E1-52.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E2-36, which are represented by SEQ ID NOs: 46, 47, 48, 113, 83, and 114, respectively. In one aspect, the isolated antibody comprises CDR sequences that are identical to the CDR sequences of monoclonal antibody E2-36.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E2-36 (SEQ ID NO: 171) or the humanized $V_H$ domain of E2-36 mAB; and a $V_L$ domain at least about 80%, 85%, 90%, 91%, 92%, 93%, 94%, 95%, 96%, 97%, 98%, 99% or 100% identical to the $V_L$ domain of E2-36 (SEQ ID NO: 172) or the humanized $V_L$ domain of E2-36 mAB. For example, the antibody can comprise a $V_H$ domain at least 95% identical to the $V_H$ domain of the humanized E2-36 mAB and a $V_L$ domain at least 95% identical to the $V_L$ domain of the humanized E2-36 mAB. Thus, in some aspects, an antibody comprises a $V_H$ domain identical to the $V_H$ domain of humanized E2-36 mAB and a $V_L$ domain identical to the $V_L$ domain of the humanized E2-36 mAB. In a specific example, the isolated antibody can comprise $V_H$ and $V_L$ domains identical to those of monoclonal antibody E2-36.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E1-95, which are represented by SEQ ID NOs: 52, 53, 54, 117, 83, 119, respectively. In one aspect, the isolated antibody comprises CDR sequences that are identical to the CDR sequences of monoclonal antibody E1-95.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E1-95 (SEQ ID NO: 173) or the humanized $V_H$ domain of E1-95 mAB; and a $V_L$ domain at least about 80%, 85%, 90%, 91%, 92%, 93%, 94%, 95%, 96%, 97%, 98%, 99% or 100% to the $V_L$ domain of E1-95 (SEQ ID NO: 174) or the humanized $V_L$ domain of E1-95 mAB. For example, the antibody can comprise a $V_H$ domain at least 95% identical to the $V_H$ domain of the humanized E1-95 mAB and a $V_L$ domain at least 95% identical to the $V_L$ domain of the humanized E1-95 mAB. Thus, in some aspects, an antibody comprises a $V_H$ domain identical to the $V_H$ domain of humanized E1-95 mAB and a $V_L$ domain identical to the $V_L$ domain of the humanized E1-95 mAB. In a specific example, the isolated antibody can comprise $V_H$ and $V_L$ domains identical to those of monoclonal antibody E1-95.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of monoclonal antibody E2-116, which are represented by SEQ ID NOs: 58, 59, 60, 121, 100, and 122, respectively. In one aspect, the isolated antibody comprises CDR sequences that are identical to the CDR sequences of monoclonal antibody E2-116.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E2-116 (SEQ ID NO: 175) or the humanized $V_H$ domain of E2-116 mAB; and a $V_L$ domain at least about 80%, 85%, 90%, 91%, 92%, 93%, 94%, 95%, 96%, 97%, 98%, 99% or 100% identical to the $V_L$ domain of E2-116 (SEQ ID NO: 176) or the humanized $V_L$ domain of E2-116 mAB. For example, the antibody can comprise a $V_H$ domain at least 95% identical to the $V_H$ domain of the humanized E2-116 mAB and a $V_L$ domain at least 95% identical to the $V_L$ domain of the humanized E2-116 mAB. Thus, in some aspects, an antibody comprises a $V_H$ domain identical to the V_H domain of humanized E2-116 mAB and a V_L domain identical to the V_L domain of the humanized E2-116 mAB. In a specific example, the isolated antibody can comprise V_H and V_L domains identical to those of monoclonal antibody E2-116.

In further aspects, the isolated antibody comprises a first V_H, a second V_H, a third V_H, a first V_L, a second V_L, and a third V_L CDR sequence at least 80%, 85%, 90%, 91%, 92%, 93%, 94%, 95%, 96%, 97%, 98%, 99% or 100% identical to the corresponding CDR sequence of monoclonal antibody E2-135, which are represented by SEQ ID NOs: 64, 65, 66, 126, 127, and 128, respectively. In one aspect, the isolated antibody comprises CDR sequences that are identical to the CDR sequences of monoclonal antibody E2-135.

In another aspect, the isolated antibody comprises a V_H domain at least about 80%, 85%, 90%, 91%, 92%, 93%, 94%, 95%, 96%, 97%, 98%, 99% or 100% identical to the V_H domain of E2-135 (SEQ ID NO: 177) or the humanized V_H domain of E2-135 mAB; and a V_L domain at least about 80%, 85%, 90%, 91%, 92%, 93%, 94%, 95%, 96%, 97%, 98%, 99% or 100% identical to the V_L domain of E2-135 (SEQ ID NO: 178) or the humanized V_L domain of E2-135 mAB. For example, the antibody can comprise a V_H domain at least 95% identical to the V_H domain of the humanized E2-135 mAB and a V_L domain at least 95% identical to the V_L domain of the humanized E2-135 mAB. Thus, in some aspects, an antibody comprises a V_H domain identical to the V_H domain of humanized E2-135 mAB and a V_L domain identical to the V_L domain of the humanized E2-135 mAB. In a specific example, the isolated antibody can comprise V_H and V_L domains identical to those of monoclonal antibody E2-135.

In further aspects, the isolated antibody comprises a first V_H, a second V_H, a third V_H, a first V_L, a second V_L, and a third V_L CDR sequence at least 80%, 85%, 90%, 91%, 92%, 93%, 94%, 95%, 96%, 97%, 98%, 99% or 100% identical to the corresponding CDR sequence of monoclonal antibody E1-142, which are represented by SEQ ID NOs: 70, 71, 72, 131, 100, and 132, respectively. In one aspect, the isolated antibody comprises CDR sequences that are identical to the CDR sequences of monoclonal antibody E1-142.

In another aspect, the isolated antibody comprises a V_H domain at least about 80%, 85%, 90%, 91%, 92%, 93%, 94%, 95%, 96%, 97%, 98%, 99% or 100% identical to the V_H domain of E1-142 (SEQ ID NO: 179) or the humanized V_H domain of E1-142 mAB; and a V_L domain at least about 80%, 85%, 90%, 91%, 92%, 93%, 94%, 95%, 96%, 97%, 98%, 99% or 100% identical to the V_L domain of E1-142 (SEQ ID NO: 180) or the humanized V_L domain of E1-142 mAB. For example, the antibody can comprise a V_H domain at least 95% identical to the V_H domain of the humanized E1-142 mAB and a V_L domain at least 95% identical to the V_L domain of the humanized E1-142 mAB. Thus, in some aspects, an antibody comprises a V_H domain identical to the V_H domain of humanized E1-142 mAB and a V_L domain identical to the V_L domain of the humanized E1-142 mAB. In a specific example, the isolated antibody can comprise V_H and V_L domains identical to those of monoclonal antibody E1-142.

In some aspects, an antibody of the embodiments may be an IgG (e.g., IgG1, IgG2, IgG3 or IgG4), IgM, IgA, genetically modified IgG isotype, or an antigen binding fragment thereof. The antibody may be a Fab', a F(ab')2 a F(ab')3, a monovalent scFv, a bivalent scFv, a bispecific or a single domain antibody. The antibody may be a human, humanized, or de-immunized antibody. In a further aspect, the isolated antibody is the E1-33, E1-34, E1-80, E1-89, E2-93, E1-38, E1-52, E2-36, E1-95, E2-116, E2-135, or E1-142 antibody.

In some aspects, the antibody may be conjugated to an imaging agent, a chemotherapeutic agent, a toxin, or a radionuclide. In specific aspects, the antibody may be conjugated to auristatin or to monomethyl auristatin E (MMAE) in particular.

In one embodiment, there is provided a recombinant polypeptide comprising an antibody V_H domain comprising CDRs 1-3 of the V_H domain of E1-33 (SEQ ID NOs: 4, 5, and 6); CDRs 1-3 of the V_H domain of E1-34 (SEQ ID NOs: 10, 11, and 12); CDRs 1-3 of the V_H domain of E1-80 (SEQ ID NOs: 16, 17, and 18); CDRs 1-3 of the V_H domain of E1-89 (SEQ ID NOs: 22, 23, and 24); CDRs 1-3 of the V_H domain of E2-93 (SEQ ID NOs: 28, 29, and 30); CDRs 1-3 of the V_H domain of E1-38 (SEQ ID NOs: 34, 35, and 36); CDRs 1-3 of the V_H domain of E1-52 (SEQ ID NOs: 40, 41, and 42); CDRs 1-3 of the V_H domain of E2-36 (SEQ ID NOs: 46, 47, and 48); CDRs 1-3 of the V_H domain of E1-95 (SEQ ID NOs: 52, 53, and 54); CDRs 1-3 of the V_H domain of E2-116 (SEQ ID NOs: 58, 59, and 60); CDRs 1-3 of the V_H domain of E2-135 (SEQ ID NOs: 64, 65, and 66); or CDRs 1-3 of the V_H domain of E1-142 (SEQ ID NOs: 70, 71, and 72). In another embodiment, there is provided a recombinant polypeptide comprising an antibody V_L domain comprising CDRs 1-3 of the V_L domain of E1-33 (SEQ ID NOs: 76, 77, and 78); CDRs 1-3 of the V_L domain of E1-34 (SEQ ID NOs: 82, 83, and 84); CDRs 1-3 of the V_L domain of E1-80 (SEQ ID NOs: 88, 77, and 89); CDRs 1-3 of the V_L domain of E1-89 (SEQ ID NOs: 93, 94, and 95); CDRs 1-3 of the V_L domain of E2-93 (SEQ ID NOs: 99, 100, and 101); CDRs 1-3 of the V_L domain of E1-38 (SEQ ID NOs: 104, 100, and 105); CDRs 1-3 of the V_L domain of E1-52 (SEQ ID NOs: 108, 77, and 109); CDRs 1-3 of the V_L domain of E2-36 (SEQ ID NOs: 113, 83, and 114); CDRs 1-3 of the V_L domain of E1-95 (SEQ ID NOs: 117, 83, and 118); CDRs 1-3 of the V_L domain of E2-116 (SEQ ID NOs: 121, 100, and 122); CDRs 1-3 of the V_L domain of E2-135 (SEQ ID NOs: 126, 127, and 128); or CDRs 1-3 of the V_L domain of E1-142 (SEQ ID NOs: 131, 100, and 132).

In some embodiments, there is provided an isolated polynucleotide molecule comprising nucleic acid sequence encoding an antibody or a polypeptide comprising an antibody V_H or V_L domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a V_L or V_H chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering an effective amount of an antibody disclosed herein. In certain aspects, the antibody is a monoclonal antibody of the embodiments herein, such as the E1-33, E1-34, E1-80, E1-89, E2-93, E1-38, E1-52, E2-36, E1-95, E2-116, E2-135, or E1-142 antibody or a recombinant polypeptide comprising antibody segment derived therefrom.

In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In specific aspects, the cancer is an epithelial cancer. In other aspects, cancer may be a colorectal adenocarcinoma, lung adenocarcinoma, lung squamous cell carcinoma, breast cancer, hepatocellular carcinoma, ovarian cancer, kidney renal clear cell carcinoma, lung cancer or kidney cancer.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In another embodiment, there is provided a method for detecting a cancer in a subject comprising testing for the presence of elevated EGFL6 relative to a control in a sample from the subject, wherein the testing comprises contacting the sample with an antibody disclosed herein. For example, the method may be an in vitro or in vivo method.

Certain embodiments are directed to an antibody or recombinant polypeptide composition comprising an isolated and/or recombinant antibody or polypeptide that specifically binds EGFL6. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a EGFL6-binding antibody as provided herein.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a EGFL6-binding antibody as provided herein.

In yet further aspects, an antibody or polypeptide of the embodiments comprises an amino acid segment that is at least 80%, 85%, 90%, 91%, 92%, 93%, 94%, 95%, 96%, 97%, 98%, 99% or 100% identical (or any range derivable therein) to a V, VJ, VDJ, D, DJ, J or CDR domain of a EGFL6-binding antibody (as provided in Tables 1 and 2). For example, a polypeptide may comprise 1, 2 or 3 amino acid segment that are at least 80%, 85%, 90%, 91%, 92%, 93%, 94%, 95%, 96%, 97%, 98%, 99% or 100% identical (or any range derivable therein) to CDRs 1, 2, and/or 3 a EGFL6-binding antibody as provided in Tables 1 and 2.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIGS. 4A-D. EGFL6 is upregulated in tumor associated endothelial cells but not in normal ovary and wound healing tissue. A) Summary of isolation of endothelial cells. B) Gene microarray of endothelial cells from normal ovary, healing wound tissue and ovarian tumor associated endothelial cells. C) Expression of EGFL6, CD31 and VEGF in ovarian patients. D) Validation of gene microarray data using Q-RT PCR. Scale bar=100 μm.

FIGS. 7A-K. Treatment of endothelial cells with EGFL6 activates of PI3kinase/AKT signaling. A) RPPA analysis in control and EGFL6 treated RF24 cells. B) Western blotting of EGFL6 mediated activation of PI3Kinase/AKT signaling. C) Western blotting of EGFL6 mediated IGF-R, EGFR, and Tie2 receptor activation. D) Tie2 antibody pull-downed intergrin proteins. E) Tie2 and AKT signal pathway in cytosol and membrane fractioned proteins. F) Tie2 and AKT signal pathway in siITGB1 and siTie2 treated RF24cells. G, H) Silencing of integrin and Tie2 using specific siRNAs decreases the EGFL6 mediated tube formation (G) and migration (H) in endothelial cells. I) RGD blocking peptide decreases the integrin-mediated signal pathway J) migration K) and tube formation in endothelial cells.

FIGS. 8A-G. EGFL6 functional blocking antibody reduces angiogenesis and tumor growth. A) Line graph represent antibody binding affinity. B) Effect of EGFL6 blocking antibodies on Tie2/AKT activation in RF24 cells. Control, mAb93 and mAb135 working concentration is 10 ug/ml. C) Effect of EGFL6 blocking antibodies on wound healing assay with dermal endothelial cells. D) Effect of EGFL6 blocking antibodies on tube formation and E) migration in RF24 cells. F) Effect of EGFL6 blocking antibodies on SKOV3ip1 tumor bearing mice tumor weight, tumor nodules. G) Ki67 and CD31 expression shown the cell proliferation and vessel density. Seven days following tumor cell injection, mice were randomly divided into three groups (10 mice/group) to receive therapy: (1) Control Ab (5 mg/kg), (2) EGFL6 Ab 93 (5 mg/kg), and (3) EGFL6 Ab 135 (5 mg/kg). Antibody was given once a week. Tumors were harvested as described in the Examples herein. Wound was created and tumors were harvested as described in the Examples herein. Error bars indicates SEM. *P<0.05 vs. Control Ab.

FIG. 8H shows a representative for each group, and the bar graph illustrates the average of tube numbers in each treated group. Error bars indicate the standard error and n=3.

FIGS. 9A-C. Generation of Tie2-cre; EGFL6$^{f/f}$ knockout mice. A) Generation of Tie2 cre; EGFL6 knockout mouse. B) CD31 expression in isolated endothelial cell with littermate and EGFL6 knockout mouse. C) EGFL6 expression in isolated endothelial cells.

FIGS. 9D-G. EGFL6 gene silencing reduces the tumor burden and angiogenesis in SKOV3ip1 ovarian orthotopic mouse models. D) Expression of EGFL6 in various ovarian cancer cells. E, F) Effects of endothelial cell (mEGFL6 siRNA) or tumor (hEGFL6 siRNA) targeted EGFL6 siRNA on tumor weight and tumor nodules in SKOV3ip1 orthotopic mouse models of ovarian cancer. Seven days following tumor cell injection, mice were randomly divided into four groups (10 mice/group) to receive therapy: (1) Control siRNA, (2) mEGFL6 siRNA, (3) hEGFL6 siRNA (4) mEGFL6 siRNA+hEGFL6 siRNA. Mice were sacrificed when any animals in a control or treatment group became moribund (after 3-4 weeks of therapy) and tumor weight (E) and number of tumor nodules (F) were recorded. Error bars indicates SEM. G) Effect of targeted EGFL6 siRNAs on proliferation and microvessel density. Harvested tumors were stained for Ki67 proliferation and CD31. Scale bar=50 μm. The bars in the graphs correspond sequentially to the labeled columns of images at left. Error bars indicates SEM.

FIGS. 10A-E. EGFL6 regulates tumor angiogenesis. A) Human normal ovary, ovarian tumor, and healing wound tissues were dissociated, and isolated endothelial cells and samples were processed for microarray. B) Expression of VEGF in human normal ovary, wound, and ovarian tumor samples. C), D), E) Control siRNA- and EGFL6 siRNA-treated RF24 cells and characterized tube formation and migration. Representative images of human ovarian cancer vasculature with low or high immunohistochemical staining for EGFL6. Scale bar=200 m. Error bars indicates SEM. *p<0.05 vs. Control siRNA.

FIGS. 11A-B. Animals were treated with either Control siRNA-CH or mEGFL6 siRNA-CH with or without wound. Harvested tumors were stained for Ki67 (proliferation) and CD31 (microvessel). Error bars indicates SEM.

DESCRIPTION OF ILLUSTRATIVE EMBODIMENTS

Figure 1:
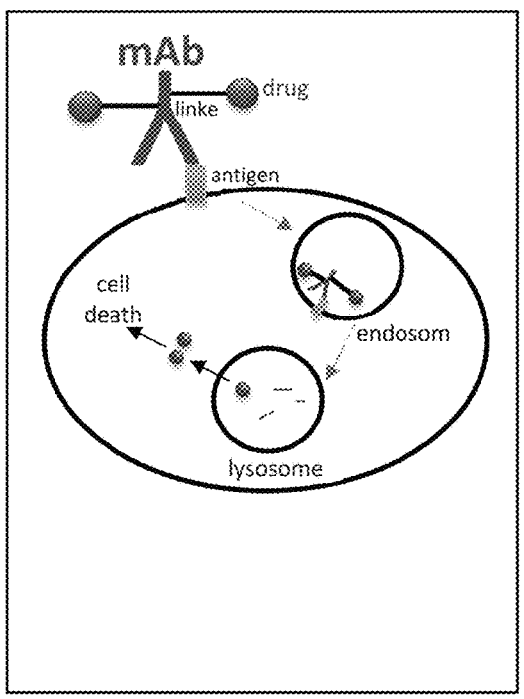
FIG. 1. A schematic diagram illustrating the working principles of ADC (antibody-drug conjugate). Upon binding to its target antigen, the MAb-antigen complex is internalized into endosomes which is then fused with lysosomes where the MAb is degraded and the drug is released.

EGFL6 is a member of the EGF repeat superfamily that is involved in wound healing. However, elevated EGFL6 has also been found in variety of cancer cell types, such as ovarian cancer and lung cancer. Studies herein demonstrate that inhibition of EGFL6 activity is effective for inhibiting cancer cell proliferation and angiogenesis in tumor tissues. Moreover, EGFL6-binding antibodies provided here were found to be effective for inhibiting EGFL6 activity and cancer cell growth. Thus, antibodies of the embodiments provide new effective methods for treating cancers and inhibiting angiogenesis.

I. ANTIBODIES OF THE EMBODIMENTS

In certain embodiments, an antibody or a fragment thereof that binds to at least a portion of EGFL6 protein and inhibits EGFL6 signaling and cancer cell proliferation are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-EGFL6 antibody is a monoclonal antibody or a humanized antibody.

Thus, by known means and as described herein, polyclonal or monoclonal antibodies, antibody fragments, and binding domains and CDRs (including engineered forms of any of the foregoing) may be created that are specific to EGFL6 protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and CH1 domains; (ii) the "Fd" fragment consisting of the $V_H$ and CH1 domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a EGFL6 extracellular domain (ECD) protein, in order to produce antibodies specific for EGFL6 protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a EGFL6 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells (CD45+CD5−CD19+) may be isolated from freshly prepared rabbit peripheral blood mononuclear cells of immunized rabbits and further selected for EGFL6 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. EGFL6 specific binding Fab may be selected out through multiple rounds enrichment panning and sequenced. Selected EGFL6 binding hits may be expressed as full length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to EGFL6 will have the ability to neutralize or counteract the effects of EGFL6 regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds EGFL6.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against EGFL6, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6?-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. TREATMENT OF DISEASES

Certain aspects of the present embodiments can be used to prevent or treat a disease or disorder associated with EGFL6 signaling. Signaling of EGFL6 may be reduced by any suitable drugs to prevent cancer cell proliferation. Preferably, such substances would be an anti-EGFL6 antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the EGFL6 signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/ aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve an antibody or an antibody fragment against EGFL6 to inhibit its activity in cancer cell proliferation, in combination with a second or additional therapy. Such therapy can be applied in the treatment of any disease that is associated with EGFL6-mediated cell proliferation. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

---
A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A
---

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs (FIG. 1). This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons □, □□ and □, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. KITS AND DIAGNOSTICS

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one EGFL6 antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation and Cloning of Monoclonal Antibodies Targeting Human EGFL6

EGFL6 (Genebank accession #Q8IUX8) protein was used to immunize New Zealand rabbits at RevMAb Biosciences USA, Inc. Titer of anti-EGFL6 sera was determined by series of dilutions of serum in ELISA for binding by coating EGFL6 protein on 96-well plates (max-sorb plates, Nunc) and were detected with an anti-rabbit antibody conjugated with horseradish peroxidase (HRP) and TMB substrate. After 2-3 immunization boosts, the titer reached >$10^6$ and peripheral blood samples were collected from the immunized rabbits for B cells (CD45+CD5−CD19+) isolation from the freshly prepared peripheral blood mononuclear cells (PBMCs) using a fluorescence assisted cell sorting (FACS) instrument (BD FACSAria™ III, BD Biosciences). The isolated B cells were plated as single B cells and cultured for 7-10 days. The culture supernatants were assayed for EGFL6 binding. Cells from the positives wells were lysed, total RNA was isolated, and cDNA was synthesized using a superscript reverse transcriptase II (Invitrogen) according to manufacturer's suggestion. DNA sequences of antibody variable region from both heavy chains and light chains were amplified by polymerase chain reaction (PCR) using a set of designed primers and sequenced. Both DNA and amino acid sequences are listed in Section V. below. CDRs of the anti-EGFL6 monoclonal antibodies were identified using the IMGT program and are listed in Tables 1 and 2.

TABLE 1

CDRs of heavy chain variable sequences of EGFL6 antibodies.

| mAb | CDR1 | CDR2 | CDR3 |
|---|---|---|---|
| E1-33 | ggactcgacctcagtagctactactac (SEQ ID NO: 1) GLDLSSYYY (SEQ ID NO: 4) | atttatgctggtagtagtggtagcact (SEQ ID NO: 2) IYAGSSGST (SEQ ID NO: 5) | gcgagaggtggtggtagtacttatgctcaatattttaacttg (SEQ ID NO: 3) ARGGGSTYAQYFNL (SEQ ID NO: 6) |
| E1-34 | ggattctccttcagtagtatttattgg (SEQ ID NO: 7) GFSFSSIYW (SEQ ID NO: 10) | attcagattactagtggtatcact (SEQ ID NO: 8) IQITSGIT (SEQ ID NO: 11) | agaaggggatatggtgcctatgctggtactggtgcctctgacttg (SEQ ID NO: 9) RRGYGAYAGTGASDL (SEQ ID NO: 12) |
| E1-80 | ggattcaccctcaatagttatat (SEQ ID NO: 13) GFTLNSYY (SEQ ID NO: 16) | attgatagtgatagtcctactacg (SEQ ID NO: 14) ISDSPTT (SEQ ID NO: 17) | gcgagaggctatggtcctgttcgattggatctc (SEQ ID NO: 15) ARGYGPVRLDL (SEQ ID NO: 18) |
| E1-89 | ggattctccttcagtagcggctactgg (SEQ ID NO: 19) GFSFSSGYW (SEQ ID NO: 22) | atttatgctggtagtagtggtgggcac (SEQ ID NO: 20) IYAGSSGGH (SEQ ID NO: 23) | tgtacaagagataattatggtggtggtggttctgcttccaaattg (SEQ ID NO: 21) CTRDNYGGGGSASKL (SEQ ID NO: 24) |
| E2-93 | ggattctccttcagtagttatgga (SEQ ID NO: 25) GFSFSSYG (SEQ ID NO: 28) | attggtcttagtagtgagatc (SEQ ID NO: 26) IGLSSEI (SEQ ID NO: 29) | gtgagagatctttatcatagtaatggtttg (SEQ ID NO: 27) VRDLYHSNGL (SEQ ID NO: 30) |
| E1-38 | ggattctccttcaatagcggctactgg (SEQ ID NO: 31) GFSFNSGYW (SEQ ID NO: 34) | atctatactagtagtcctactggtgcc (SEQ ID NO: 32) IYTSSPTGA (SEQ ID NO: 35) | tgtacaagagataattttggtggtggtggttctgcttccaaattg (SEQ ID NO: 33) CTRDNFGGGGSASKL (SEQ ID NO: 36) |

TABLE 1-continued

CDRs of heavy chain variable sequences of EGFL6 antibodies.

| mAb | Heavy Chain CDR1 | CDR2 | CDR3 |
|---|---|---|---|
| E1-52 | ggattcaccctcagtagctactac (SEQ ID NO: 37) GFTLSSYY (SEQ ID NO: 40) | attgatactgataatgatatt agg (SEQ ID NO: 38) IDTDNDIR (SEQ ID NO: 41) | gggagaggctatggtgcgctcggttggatctc (SEQ ID NO: 39) GRGYGALRLDL (SEQ ID NO: 42) |
| E2-36 | ggattctccctcagtagctacca c (SEQ ID NO: 43) GFSLSSYH (SEQ ID NO: 46) | attaataattatggtgccaca (SEQ ID NO: 44) INNYGAT (SEQ ID NO: 47) | gccagaagtcctgggattcctggttataattcg (SEQ ID NO: 45) ARSPGIPGYNS (SEQ ID NO: 48) |
| E1-95 | ggattctccttcagtagcaattc a (SEQ ID NO: 49) GFSFSSNS (SEQ ID NO: 52) | attgctagtagtagtagtcat agt (SEQ ID NO: 50) IASSSSHS (SEQ ID NO: 53) | gcgagagattctggtaatcgtggttacctttatgcg ggcgactttaacttg (SEQ ID NO: 51) ARDSGNRGYLYAGDFNL (SEQ ID NO: 54) |
| E2-116 | ggattcgacctcagtagctccta ctac (SEQ ID NO: 55) GFDLSSSYY (SEQ ID NO: 58) | attgacggtggtgggggtgag cccact (SEQ ID NO: 56) IDGGGEPT (SEQ ID NO: 59) | gcgagacgagatgctggtgctgggaacgcctttagc ttg (SEQ ID NO: 57) ARRDAGAGNAFSL (SEQ ID NO: 60) |
| E2-135 | ggattcgacttcagtagcagcta cttt (SEQ ID NO: 61) GFDFSSSYF (SEQ ID NO: 64) | atttatactgttattagtcgt aagact (SEQ ID NO: 62) IYTVISRKT (SEQ ID NO: 65) | gcgagatcggcaacaattgaaagattggatctc (SEQ ID NO: 63) ARSATIERLDL (SEQ ID NO: 66) |
| E1-142 | ggattcaccatcaataactacaa c (SEQ ID NO: 67) GFTINNYN (SEQ ID NO: 70) | atttggaatggtgatggcagc (SEQ ID NO: 68) IWNGDGS (SEQ ID NO: 71) | gcgagaaattttaacttg (SEQ ID NO: 69) ARNFNL (SEQ ID NO: 72) |

TABLE 2

CDRs of light chain variable sequences of EGFL6 antibodies.

| mAb | Light Chain CDR1 | CDR2 | CDR3 |
|---|---|---|---|
| E1-33 | ccgagtgtttataggcactac (SEQ ID NO: 73) PSVYRHY (SEQ ID NO: 76) | tgggcttcc (SEQ ID NO: 74) WAS (SEQ ID NO: 77) | gcaggcgaatatgctagtgatagtgataatcat (SEQ ID NO: 75) AGEYASDSDNH (SEQ ID NO: 78) |
| E1-34 | cagagtgtttataataacaacaac (SEQ ID NO: 79) QSVYNNNN (SEQ ID NO: 82) | gaagcatcc (SEQ ID NO: 80) EAS (SEQ ID NO: 83) | gcaggcggttatgctggctacatttgggct (SEQ ID NO: 81) AGGYAGYIWA (SEQ ID NO: 84) |
| E1-80 | aagaacgcctatttatcctactac (SEQ ID NO: 85) KNAYLSYY (SEQ ID NO: 88) | tgggcttcc (SEQ ID NO: 86) WAS (SEQ ID NO: 77) | gcagccgaatatagtaatgatagtgataatggt (SEQ ID NO: 87) AAEYSNDSDNG (SEQ ID NO: 89) |
| E1-89 | cagagtgtttatagtaacaaccgc (SEQ ID NO: 90) QSVYSNNR (SEQ ID NO: 93) | tatgcagcc (SEQ ID NO: 91) YAA (SEQ ID NO: 94) | gcaggatataaaactgctgattctgatggtattgct (SEQ ID NO: 92) AGYKTADSDGIA (SEQ ID NO: 95) |
| E2-93 | gagagcgtttataataataaccgc (SEQ ID NO: 96) ESVYNNNR (SEQ ID NO: 99) | tatgcatcc (SEQ ID NO: 97) YAS (SEQ ID NO: 100) | gtagcctttaaaggttatggtactgacggcaatgct (SEQ ID NO: 98) VAFKGYGTDGNA (SEQ ID NO: 101) |

TABLE 2-continued

CDRs of light chain variable sequences of EGFL6 antibodies.

| | Light Chain | | |
|---|---|---|---|
| | CDR1 | CDR2 | CDR3 |
| E1-38 | gagagtgtttatagtaacaaccgc (SEQ ID NO: 102) ESVYSNNR (SEQ ID NO: 104) | tatgcatcc (SEQ ID NO: 97) YAS (SEQ ID NO: 100) | gcaggatataagactgccgattctgatggtcttggt (SEQ ID NO: 103) AGYKTADSDGLG (SEQ ID NO: 105) |
| E1-52 | ccgagtgtttataggcactac (SEQ ID NO: 106) PSVYRHY (SEQ ID NO: 108) | tgggcttcc (SEQ ID NO: 86) WAS (SEQ ID NO: 77) | gcaggcgaatatgctagtgatagtgataatcat (SEQ ID NO: 107) AGEYASDSDNH (SEQ ID NO: 109) |
| E2-36 | cagaatgtttatagttacaaccgc (SEQ ID NO: 110) QNVYSYNR (SEQ ID NO: 113) | gaagcatcc (SEQ ID NO: 111) EAS (SEQ ID NO: 83) | gcaggcggttatgattgtaggagttctgattgtgat gct (SEQ ID NO: 112) AGGYDCRSSDCDA (SEQ ID NO: 114) |
| E1-95 | cagagcattaatagttgg (SEQ ID NO: 115) QSINSW (SEQ ID NO: 117) | gaagcatcc (SEQ ID NO: 111) EAS (SEQ ID NO: 83) | caacagggttatagttatagtaatgttgataataat att (SEQ ID NO: 116) QQGYSYSNVDNNI (SEQ ID NO: 118) |
| E2-116 | caaagtgtttatcttcagaacaac (SEQ ID NO: 119) QSVYLQNN (SEQ ID NO: 121) | tatgcatcc (SEQ ID NO: 97) YAS (SEQ ID NO: 100) | cagggcggttacagtggatatatcaattct (SEQ ID NO: 120) QGGYSGYINS (SEQ ID NO: 122) |
| E2-135 | gagagtgtttataataactaccgc (SEQ ID NO: 123) ESVYNNYR (SEQ ID NO: 126) | gctgcatcc (SEQ ID NO: 124) AAS (SEQ ID NO: 127) | gtaggatataaaagtggttatattgatagtattcct (SEQ ID NO: 125) VGYKSGYIDSIP (SEQ ID NO: 128) |
| E1-142 | gcgagtgtttatagtaacaactac (SEQ ID NO: 129) ASVYSNNY (SEQ ID NO: 131) | tatgcatcc (SEQ ID NO: 97) YAS (SEQ ID NO: 100) | gcaggcgattatagtagtagtagtgatatgtgtatt (SEQ ID NO: 130) AGDYSSSDMCI (SEQ ID NO: 132) |

Selected EGFL6 binding hits were expressed as rabbit or rabbit/human chimeric IgGs using a mammalian expression vector system in human embryonic kidney (HEK293) cells (Invitrogen). Antibodies were purified using a column with protein A resin by a fast protein liquid chromatography (FPLC) separation unit. Purified EGFL6 binding antibodies were characterized for their biological properties.

Figure 2:
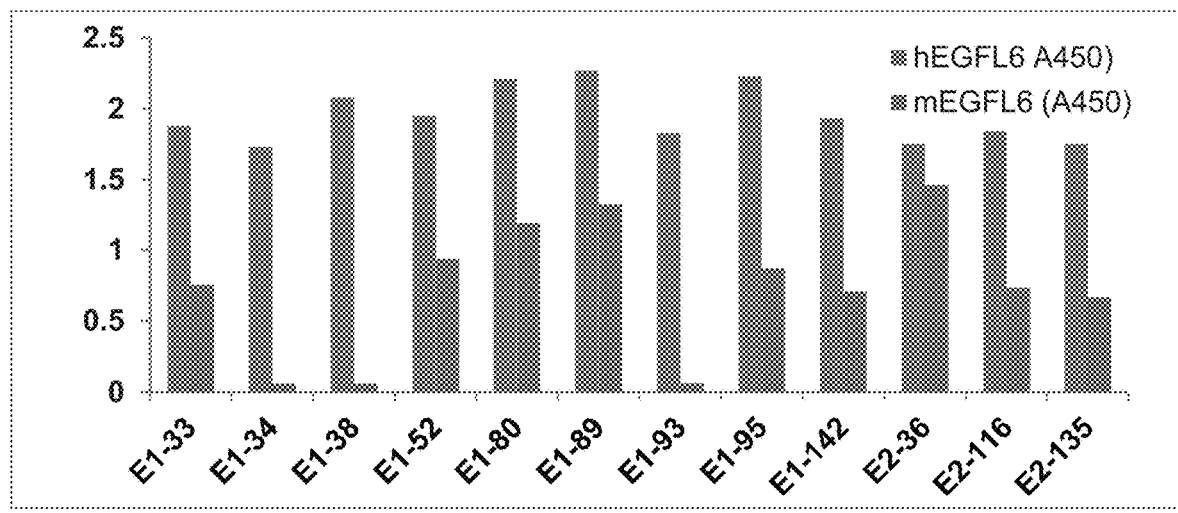
FIG. 2. Detection of high binding EGFL6 antibodies by ELISA. Human (left bars) or mouse (right bars) EGFL6 protein (Sino Biologicals) was coated on a 96-well high binding plate over night at 4° C. in PBS. B cell culture supernatants (5 □l medium and 95 □l of PBS) were added at for binding to EGFL6 antigen coated on the plate. Bound antibody was detected using a secondary antibody against rabbit IgG conjugated with HRP and TMB substrate. Experiments were repeated 2 times for confirmation.
Figure 3:
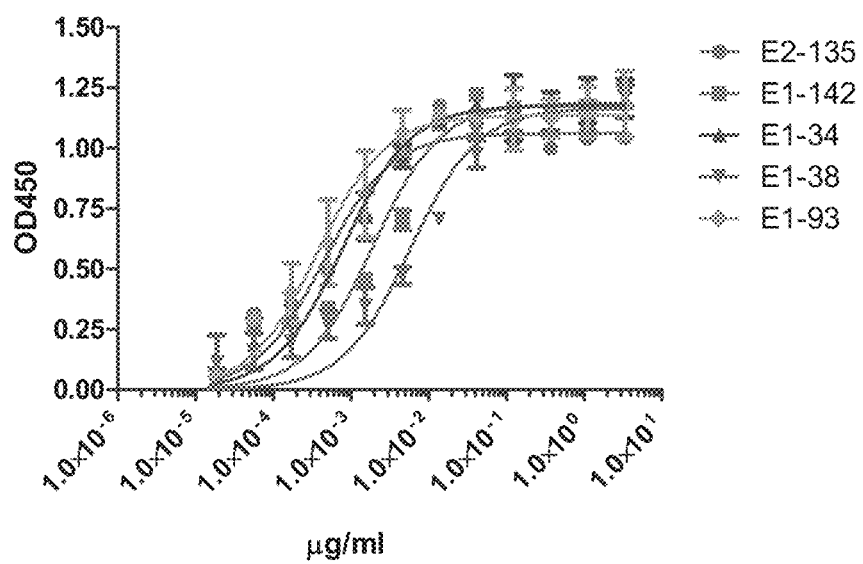
FIG. 3. Determination of binding affinities of EGFL6 antibodies in ELISA. A series of antibody concentrations was assayed in ELISA and 4-parameter fitting was used to calculate binding affinity of the antibodies. Experiments have 3 repeats and error bars indicate standard deviation.

Example 2—Binding Affinity of Anti-EGFL6 Monoclonal Antibodies to the EGFL6 Protein Binding of EGFL6 by monoclonal antibodies was first screened by ELISA using supernatants collected from the B cell cultures (FIG. 2). ELISA titration was used to determine the binding affinity of a panel of monoclonal antibodies to EGFL6 antigen (FIG. 3). Binding constants ($K_D$ and/or EC 50) of a panel of monoclonal antibodies were estimated using the 4 parameter curve fitting with Prism GraphPad program. For Biacore analysis, all experiments were performed at 25° C. at a flow rate of 45 µl/min. An anti-human IgG Fc antibody (from ThermoFisher, at 50 µg/ml each in acetate buffer, pH 5.0) was immobilized onto a carboxymethyl dextran sensorchip (CM5) using amine coupling procedures based on instruction from the manufacturer. Purified rabbit/human chimeric antibody to be tested was diluted at a concentration of 5 µg/ml in 0.5% P20, HBS-EP buffer and injected on FC2 to reach 500 to 1000 RU. FC1 was used as the reference cell. Specific signals correspond to the difference of signals obtained on FC2 versus FC1. The analyte (recombinant human EGFL6, apparent molecular weight 60 kDa on SDS-PAGE gel) was injected during 90 sec at series of concentration dilutions (100, 50, 25, 12.5, 6.25, and 3.13, 1.56 nM) in 0.5% P20, HBS-EP buffer. These concentrations were prepared from stock solution in 0.5% P20, HBS-EP. The dissociation phase of the analyte was monitored over a 30 minutes period. Running buffer was also injected under the same conditions as a double reference. After each running cycle, both flow cells were regenerated by injecting 20 to 45 µl of Glycine-HCl buffer pH 1.5. Binding $K_D$ on EGFL6 was calculated by $k_{off}/k_{on}$ kinetic rate for each EGFL6 monoclonal antibodies (Table 3).

TABLE 3

EGFL6 antibody binding affinities determined by ELISA or Biacore method.

| Antibody name | EC50 (ng/ml) |
|---|---|
| E1-34 | 0.78 |
| E1-38 | 5.81 |
| E2-93 | 0.37 |
| E1-142 | 1.91 |
| E2-135 | 0.44 |

Example 3—Experimental Procedures and Methods

Cell lines and culture: Human epithelial ovarian cancer cell lines, SKOV3ip1 and A2780ip2 were maintained as described (Sood, A. K. et al. Molecular determinants of ovarian cancer plasticity. American Journal of Pathology 158, 1279-1288, 2001). Human immortalized umbilical endothelial cells (RF24) were grown in MEM medium with supplements (sodium pyruvate, non-essential amino acids, MEM vitamins and glutamine; Life Technologies). The derivation and characterization of the mouse ovarian endothelial cells (MOEC) has been described previously (Langley, R. R. et al. Tissue-specific microvascular endothelial cell lines from H-2K(b)-tsA58 mice for studies of angiogenesis and metastasis. *Cancer Research* 63, 2971-2976, 2003). Cell cultures were maintained at 37° C. in a 5% CO2 incubator with 95% humidity. For in vivo injections, cells were trypsinized and centrifuged at 1,200 rpm for 5 min at 4° C., washed twice with PBS, and reconstituted in serum-free Hank's balanced salt solution (Life Technologies, Grand Island, NY, USA). Only single-cell suspensions with more than 95% viability (as determined by trypan blue exclusion) were used for in vivo intra-peritoneal injections.

Endothelial cell isolation: Fresh tissue samples (5 normal ovaries, 5 wound tissue and 10 epithelial high-grade, stage III or IV invasive serous ovarian cancers) were obtained from patients undergoing primary surgical exploration at the M. D. Anderson Cancer Center after approval from the Institutional Review Board. Total RNA from purified endothelial cells was subjected to microarray analysis using the Affymetrix Human U133 plus 2.0 GeneChip platform (Lu, C. et al. Gene alterations identified by expression profiling in tumor-associated endothelial cells from invasive ovarian carcinoma. *Cancer Research* 67, 1757-1768, 2007).

Quantitative real-time PCR validation: Quantitative real-time RT-PCR was performed using 50 ng of total RNA from purified endothelial cells was isolated using the RNeasy mini kit (Qiagen) according to the manufacturer's instructions. Complementary DNA (cDNA) was synthesized from 0.5-1 g of total RNA using Verso cDNA kit (Thermo Scientific). Quantitative PCR (qPCR) analysis was performed in triplicate using the SYBR Green ER qPCR SuperMix Universal (Invitrogen) and Bio-Rad (Bio-Rad Laboratories, Hercules, CA, USA). Relative quantification was calculated using the $2^{-\Delta\Delta CT}$ method normalizing to control for percent fold changes (Donninger, H. et al. Whole genome expression profiling of advance stage papillary serous ovarian cancer reveals activated pathways. *Oncogene* 23, 8065-8077, 2004).

SiRNA constructs and delivery: SiRNAs were purchased from Sigma-Aldrich (The Woodlands, TX, USA). A non-silencing siRNA that did not share sequence homology with any known human mRNA based on a BLAST search was used as control for target siRNA. In vitro transient transfection was performed as described (Landen, C. N., Jr. et al. Therapeutic EphA2 gene targeting in vivo using neutral liposomal small interfering RNA delivery. *Cancer Research* 65, 6910-6918, 2005). Briefly, siRNA (4 g) was incubated with 10 L of Lipofectamine 2000 transfection reagent (Lipofectamine) for 20 min at room temperature according to manufacturer's instructions and added to cells in culture at 80% confluence in 10 cm culture plates.

Reverse phase protein array (RPPA) and Western blot analysis: RF24 and OVCAR3 cells in the presence or absence of human recombinant EGFL6 protein were subjected to RPPA analysis. Western blot analysis was performed as previously (Landen, C. N., Jr. et al. 2005, ibid; Halder, J. et al. Focal adhesion kinase targeting using in vivo short interfering RNA delivery in neutral liposomes for ovarian carcinoma therapy. *Clinical Cancer Research: an official journal of the American Association for Cancer Research* 12, 4916-4924, 2006). Cell lysate of RF24 cells treated with human recombinant EGFL6 protein or anti-EGFL6 antibodies and checked for activation of PI3kinase and AKT signaling using anti-human EGFL6, PI3kinase and AKT antibodies followed by secondary antibodies conjugated with horseradish peroxidase (HRP).

Cell migration assay: Using modified Boyden chambers coated with 0.1% gelatin, migration of the RF24 cells was assessed in the presence or absence of hEGFL6 siRNA. After post transfection of 48 h with hEGFL6 or integrin siRNAs or with EGFL6 antibody or PI3kinase inhibitor for 6 h, RF24 cells ($1.0\times10^5$) in MEM serum free medium were seeded into the upper chamber of the Transwell pore Polycarbonate Membrane insert (Corning, Lowell, MA, USA). The chamber was placed in a 24-well plate containing MEM medium with 15% serum in the lower chamber as chemoattractant. Cells were allowed to migrate in a humidified incubator for 6 h. Cells that had migrated were stained using hematoxylin staining and counted by light microscopy in five random fields (200× original magnification) per sample. Experiments were done in duplicate and performed three times.

Tube formation assay: Matrigel (12.5 mg/mL) was thawed at 4° C. and 50 µL were quickly added to each well of a 96-well plate and allowed to solidify for 10 min at 37° C. The wells were then incubated for 6 h at 37° C. with RF24 cells (20,000 per well), which had previously been treated with EGFL6 or integrin siRNA (for 48 h) or EGFL6 antibody or PI3kinase inhibitor (for 6 h). Experiments were performed in triplicate and repeated twice. Using an Olympus IX81 inverted microscope, five images per well were taken at ×100 magnification. The amount of nodes (defined as when at least three cells formed a single point) per image was quantified. To account for cell clumping, the highest and lowest value was removed from each group.

Promoter analysis and chromatin immunoprecipitation (ChIP) assay: RF24 cells were cultured in low serum medium (0.5% serum) for 18 h and then treated with either EGFL6 or HIF1α (50 ng/mL) for 6 hours. After treatment, ChIP assays were performed using EZ ChIP™ kit (Millipore, Temecula, CA, USA) as described by the manufacturer. Briefly, cross-linked cells were collected, lysed, sonicated and subsequently subjected to immunoprecipitation with EGFL6 (Abchem) antibody or IgG control. Immunocomplexes were collected with protein G agarose beads and eluted. Cross-links were reversed by incubating at 65° C. DNA then was extracted and purified for PCR using primers pairs upstream of the EGFL6 transcription start site.

Flow cytometric analysis: RF24 cells were washed with PBS and harvested with PBS-EDTA 5 mM. Cells were then immunolabeled with different integrin primary antibodies (Sigma-Aldrich) and subsequently stained with secondary antibodies (Invitrogen). Samples were acquired on a FACSCalibur with Cell Quest software and data were analyzed with FlowJo software.

Orthotopic in vivo model of ovarian cancer and tissue processing: Female athymic nude mice (NCr-nu) were purchased from the NCI-Frederick Cancer Research and Development Center (Frederick, MD, USA) and maintained as previously described (Landen, C. N., Jr. et al. 2005, ibid). All mouse studies were approved by the Institutional Animal Care and Use Committee. Mice were cared for in accordance with guidelines set forth by the American Association for Accreditation of Laboratory Animal Care and the US Public Health Service Policy on Human Care and Use of Laboratory Animals. For tumor cells injection, A2780ip2 or SKOV3ip1 or OVCAR3 cells (1×10$^6$) were injected intra peritoneal (i.p). For therapy experiments, each siRNA was given twice weekly at a dose of 150 µg/kg body weight. At the time of sacrifice, mouse and tumor weight, number and distribution of tumors were recorded. Individuals who performed the necropsies were blinded to the treatment group assignments. Tissue specimens were fixed either with formalin, OCT (Miles, Inc., Elkhart, IN, USA) or snap frozen in liquid nitrogen. For off-target effects, SKOV3ip1 tumor bearing mice were treated with two different EGFL6 siRNA sequences same as mentioned above.

Immunohistochemical and Immunofluorescence staining of xenografts: IHC analysis for cell proliferation (Ki67, 1:200, Zymed), microvessel density (MVD, CD31, 1:500, Pharmingen), and hypoxia (carbonic anhydrase Anti-CA9, 1:500, Novus), were all performed as described (Thaker, P. H. et al. Chronic stress promotes tumor growth and angiogenesis in a mouse model of ovarian carcinoma. *Nature Medicine* 12, 939-944, 2006; Lu, C. et al. Regulation of tumor angiogenesis by EZH2. *Cancer Cell* 18, 185-197, 2010). For statistical analyses, sections from five randomly selected tumors per group were stained and 5 random fields per tumor were scored. Pictures were taken at ×200 or ×100 magnification. To quantify MVD in the mouse tumor samples, the number of blood vessels staining positive for CD31 was recorded in 10 random 0.159-mm2 fields at ×200 magnification. To quantify PCNA expression, the number of positive cells (3,3'-diaminobenzidine staining) was counted in 10 random 0.159-mm$^2$ fields at ×100 magnification (Thaker, P. H. et al. 2006, ibid; Lu, C. et al. 2010, ibid). All staining was quantified by 2 investigators in a blinded fashion. Staining for EGFL6 (Santa Cruz) and CD31 was performed using frozen tissue as described (Lu, C. et al. 2010, ibid).

Matrigel plug assay: An in-vivo matrigel plug assay was performed by injecting matrigel plugs into mice subcutaneously. The matrigel plug included either serum free MEM complete medium (as negative control), VEGF (as positive control) or EGFL6 (as test group). After 6 h post injection, animals were sacrificed and the matrigel was collected and hemoglobin assay was performed.

Wound healing assay: On day 1, A2780 ip2 cells were injected into nude mice and on day 2 a wound was created on back of the tumor bearing mice. Animals received veterinary care and were maintained in individual cages. Mice were divided into two groups (n=10).

CH/ControlsiRNA and CH/mEGFL6 siRNA nanoparticles: siRNA treatment was started on day 3 and given twice a week (150 µg/kg). Wound was measured on day 0, 1, 3, 5, 7, 9, 11, 13, and 15 (till the completion of wound healing). The tumors were harvested when animals in any group became moribund.

Hind-Limb Ischemia: Critical hind-limb ischemia as described previously (Baluk, P., Hashizume, H. & McDonald, D. M. Cellular abnormalities of blood vessels as targets in cancer. *Current Opinion in Genetics & Development* 15, 102-111, 2005) was induced in female nude mice after being anesthetized with ketamine (100 mg/kg) by intraperitoneal injection and the femoral artery was excised from its proximal origin as a branch of the external iliac artery to the distal point where it bifurcates into the saphenous and popliteal arteries. After arterial ligation, mice were immediately assigned to the following experimental groups (n=5): control group, ischemia-24 h and ischemia-96 h. Serial laser Doppler imaging analysis (Moor Instruments, Devon, UK) was performed to monitor the blood flow of hind-limbs before and after femoral artery ligation (after 24 h and 96 h). The digital color-coded images were analyzed to quantify the blood flow in the region from the knee to the toe; the mean values of perfusion were calculated. At each time point, tissue from the ischemic limb was harvested and frozen in OCT medium. Mouse monoclonal anti-CD31 was used to determine the MVD and mouse polyclonal anti-EGFL6 antibody for EGFL6 expression on frozen embedded tissues using standard immunostaining procedure.

Human ovarian cancer specimens: Following approval by the Institutional Review Board, 180 paraffin-embedded epithelial ovarian cancer specimens (collected between 1985-2004) with available clinical outcome data and confirmed diagnosis by a board-certified gynecologic pathologist were obtained from the Karmanos Cancer Institute tumor bank.

For human ovarian cancer samples, immunohistochemistry for EGFL6, CD34, and VEGF, was performed, as described previously (Ali-Fehmi, R. et al. Expression of cyclooxygenase-2 in advanced stage ovarian serous carcinoma: correlation with tumor cell proliferation, apoptosis, angiogenesis, and survival. *American Journal of Obstetrics and Gynecology* 192, 819-825, 2005). EGFL6 staining was performed using an anti-human EGFL6 antibody (Sigma-Aldrich). In brief, formalin-fixed, paraffin-embedded tissue sections were de-paraffinized and rehydrated. After antigen retrieval with Diva solution, the endogenous peroxidase was blocked with 3% hydrogen peroxide in methanol for 15 min. After washing with PBS, sections were blocked with protein block (5% normal horse serum and 1% goat serum) for 20 min at room temperature (RT), followed by incubation with the anti-EGFL6 antibody (Sigma-Aldrich) overnight at 4° C. After washing with PBS, sections were incubated with horseradish peroxidase (HRP)-conjugated goat anti-rabbit (1:250, Jackson ImmunoResearch) for 1 h at RT. Finally, visualization was attained with 3, 3'-diaminobenzidine (Research Genetics) and counter-staining with Gill's hematoxylin (BioGenex Laboratories). Negative staining was reported as score 0, scores 1-4 were used for increasing intensity of EGFL6. The stained slides were scored by two investigators on the basis of the histochemical score (H-score; >100 defined as high expression and <100, low expression), according to the method described previously (Ali-Fehmi, et al., 2005 ibid), which considers both the intensity of staining and the percentage of cells stained.

Statistical analysis: For animal experiments, ten mice were assigned per treatment group. This sample size gave 80% power to detect a 50% reduction in tumor weight with 95% confidence. Tumor weights and the number of tumor nodules for each group were compared using Student's t-test (for comparisons of two groups). A P-value less than 0.05 were deemed statistically significant. All statistical tests were two-sided and were performed using SPSS version 12 for Windows statistical software (SPSS, Inc., Chicago, IL, USA).

Example 4—EGFL6 Expression Upregulated in Tumor Associated Endothelial Cells

Figure 4A:
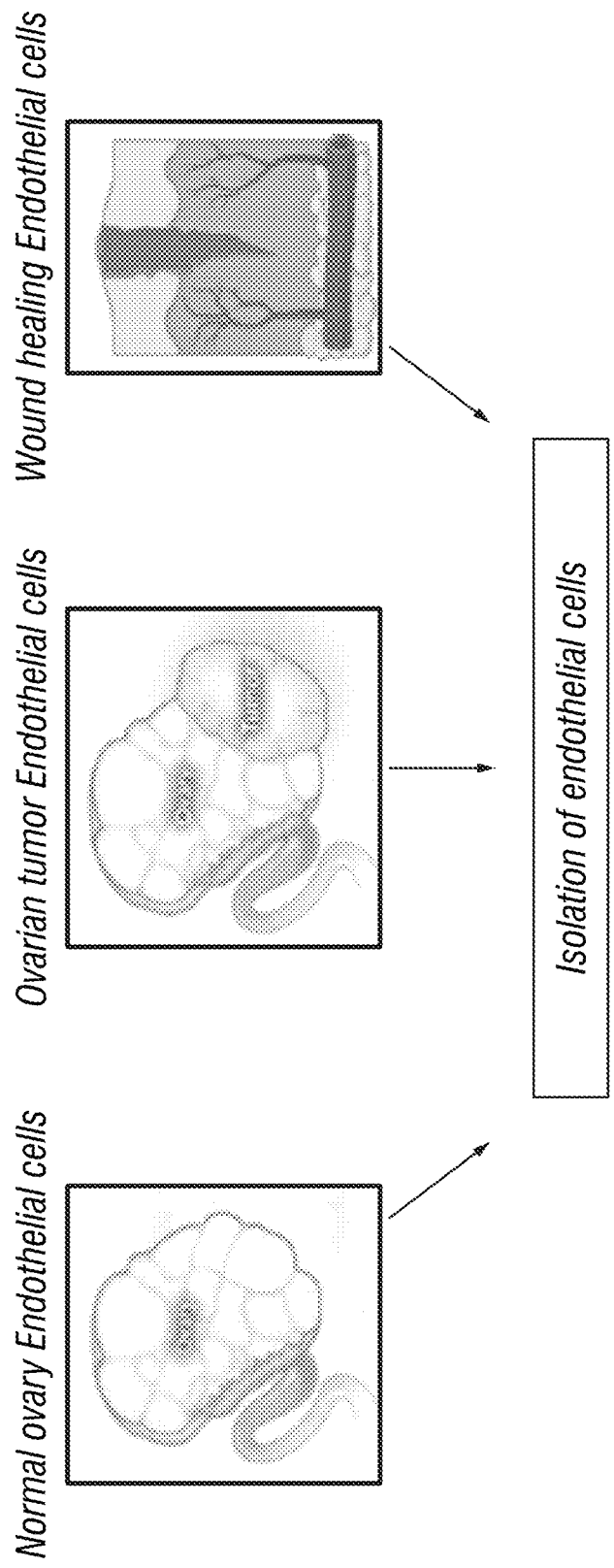
Figure 4B:
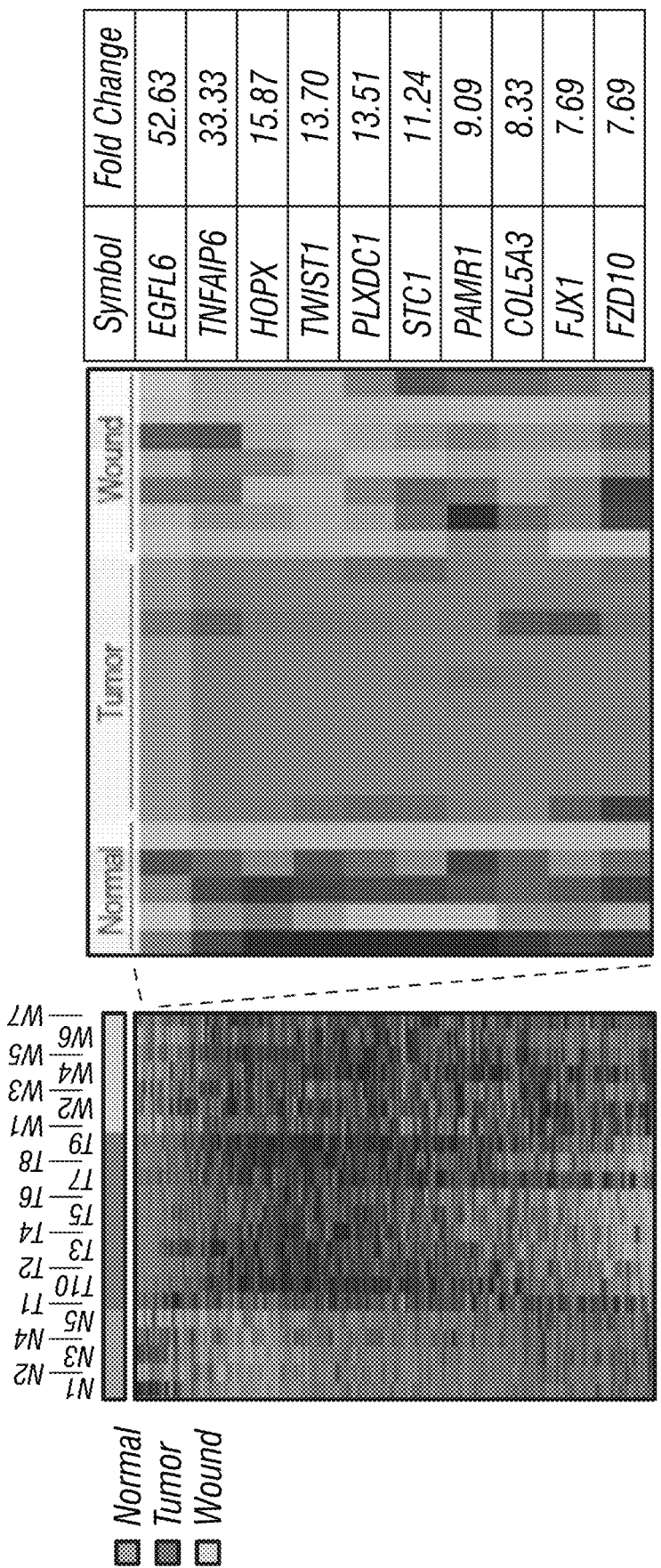
Figure 4C:
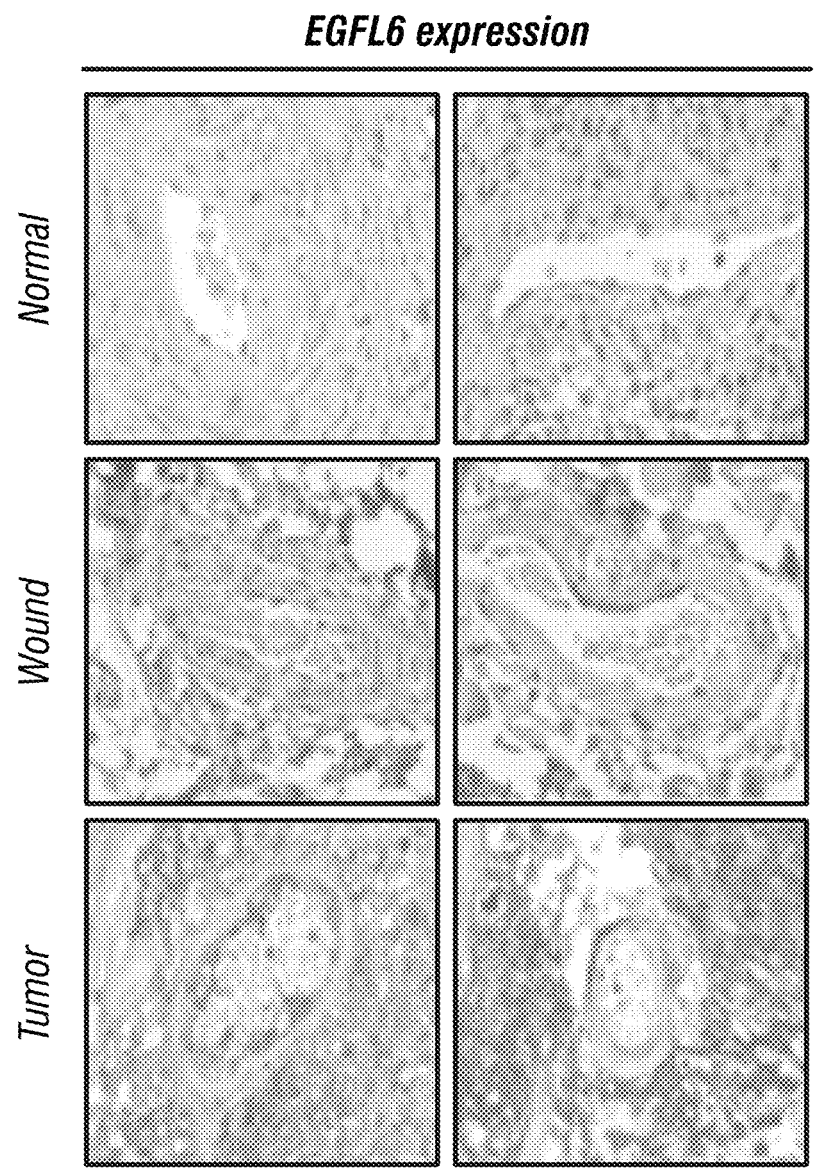

Five normal ovaries, five wound tissue samples and 10 invasive epithelial ovarian tumors were obtained and subjected to negative and positive immunoselection. Prior to carrying out microarray analysis, the purity of all samples for endothelial cells was established using the endothelial cell markers P1H12 and von Willebrand factor (FIG. 4A). Immunostaining revealed that the immunopurification technique had yielded endothelial cell purity of >95% in all samples. Analysis of the data revealed that 375 genes were upregulated in ovarian tumor endothelial cells compared to normal and wound endothelial cells (FIG. 4B). Among them, EGFL6 showed the highest differential expression in tumor endothelial cells compared to normal and wound endothelial cells (FIG. 4B). Expression of EGFL6, VEGF and CD31 in ovarian patient samples was determined (FIG. 4C). To further validate this result, endothelial cells were isolated from normal ovary, ovarian tumor and wound healing tissue and the expression of EGFL6 was determined using PCR. EGFL6 predominantly overexpressed only in tumor endothelial cells as compared to normal or wound endothelial cells (FIG. 4D). EGFL6 upregulation in tumor endothelial cells was also demonstrated. EGFL6 was expressed in endothelial cells and most of the ovarian cancer cells tested. To demonstrate the role of EGFL6 in tumor angiogenesis, RF24 cells were treated with siEGFL6 which resulted in a greater than 80% knockdown in protein levels at 72 hrs as compared to control cells. EGFL6 siRNA treated cells showed significantly less migration and tube formation compared to control siRNA treated cells indicating the importance of EGFL6 in angiogenesis.

Example 5—EGFL6 Silencing Did not Affect Wound Healing in Mice

The role of EGFL6 in wound healing was addressed using wounds generated using human dermal microvascular endothelial cells (HDMECs). Effects on wound healing were conducted using following procedures. On day 1, SKOV3ip1 cells were injected into nude mice and on day 2 wound was created on back of the tumor bearing mice (2 cm×2 cm). Animals were randomly divided into two groups (n=10), one with administration of control antibody and the other group of mice were treated with EGFL6 antibody. Antibody treatment was started on day 3 and given once a week (5 mg/kg). Wound (area=length×width) was monitored for 2 weeks until completion of wound healing. EGFL6 antibody did not prevent wound healing when tested using a wound healing in vivo study (FIG. 9C).

Figure 5A:
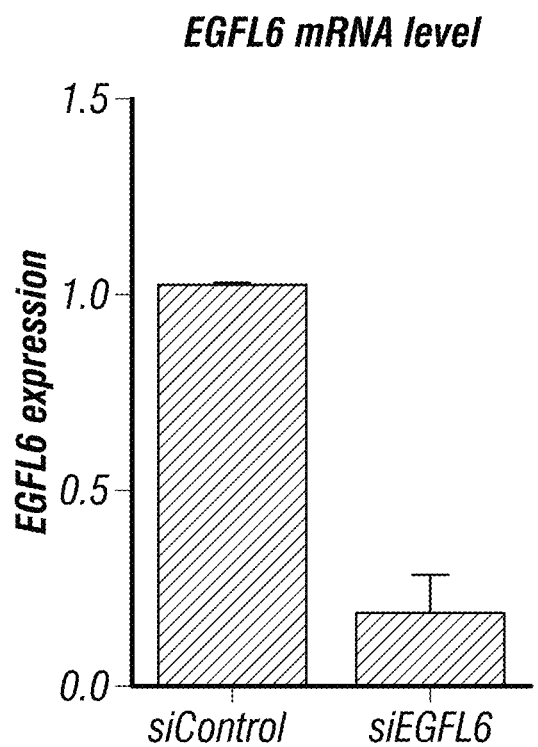
FIGS. 5A-H. EGFL6 gene silencing did not compromise wound healing but reduced the tumor burden in A2780ip2 ovarian orthotopic mouse model. A) Expression of EGFL6 in siControl and siEGFL6 treated dermal endothelial cells. B) Effect of EGFL6 silencing on wound healing in vitro. C) Bar graph represent wound healing area. D) Effect of EGFL6 silencing on wound healing E) wound volume F) Representative images of tumor burden G) tumor weight and H) tumor nodules.
Figure 5B:
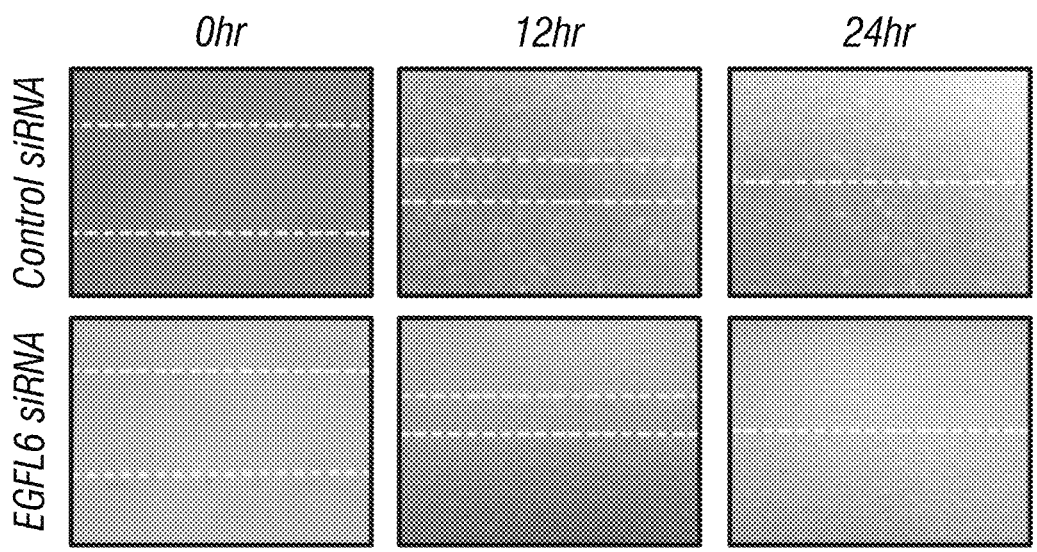
Figure 5C:
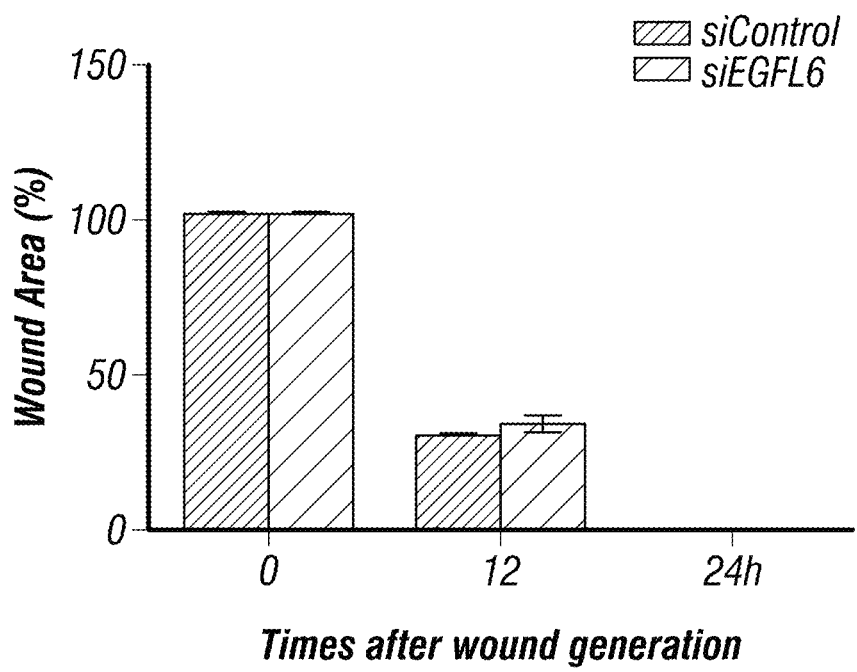
Figure 5D:
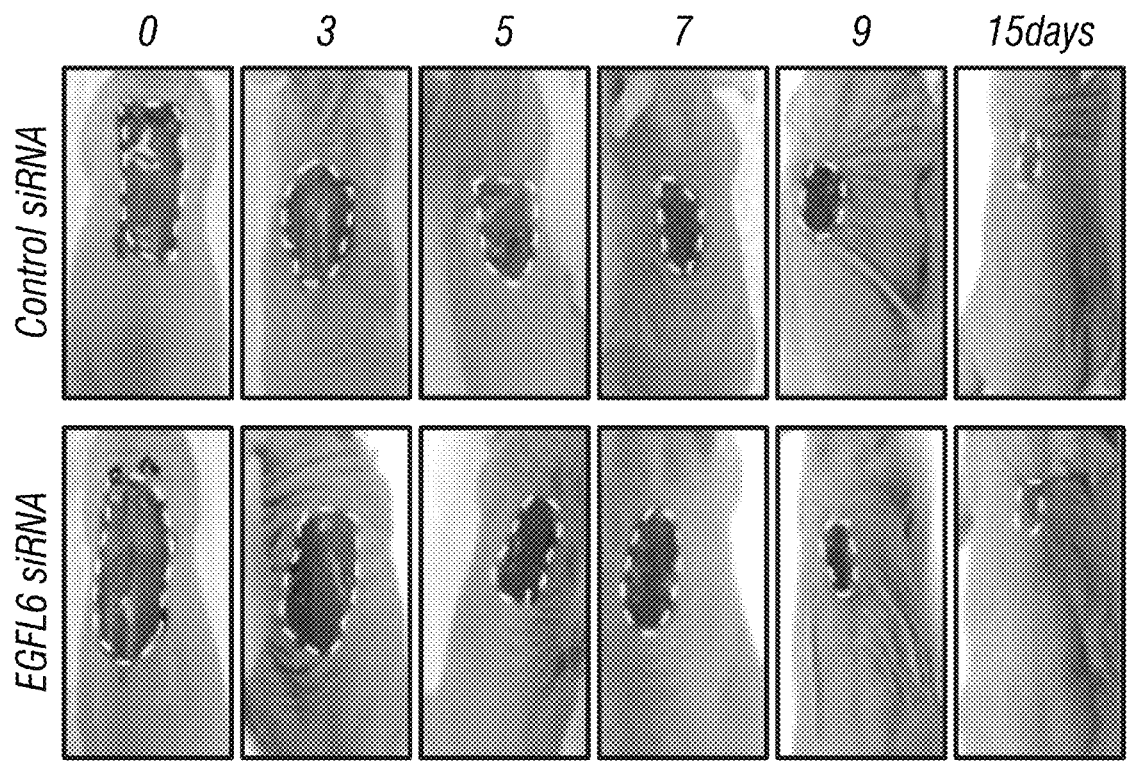
Figure 5E:
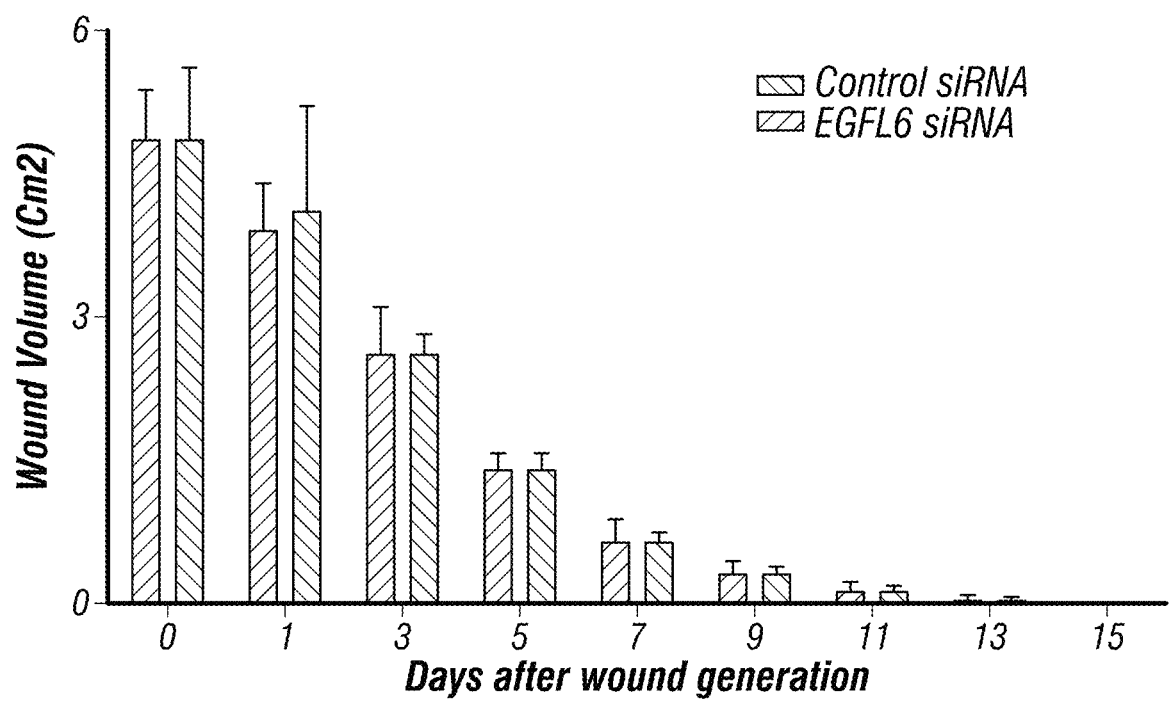

In a wound-healing assay revealed that after 24 hrs, siControl treated cells and siEGFL6 treated cells had no effect on wound healing capacity (FIGS. 5A-5C). Moreover, similar wounds generated on tumor bearing mice were used to determine the effect on wound healing of EGFL6 silencing in endothelial cell compartment using murine siRNA sequence. As shown in FIGS. 5D and 5E, no significant difference was observed in the wound healing of the animals treated with control siRNA or mouse EGFL6 siRNAs and both groups also showed similar patterns of wound healing.

Figure 5F:
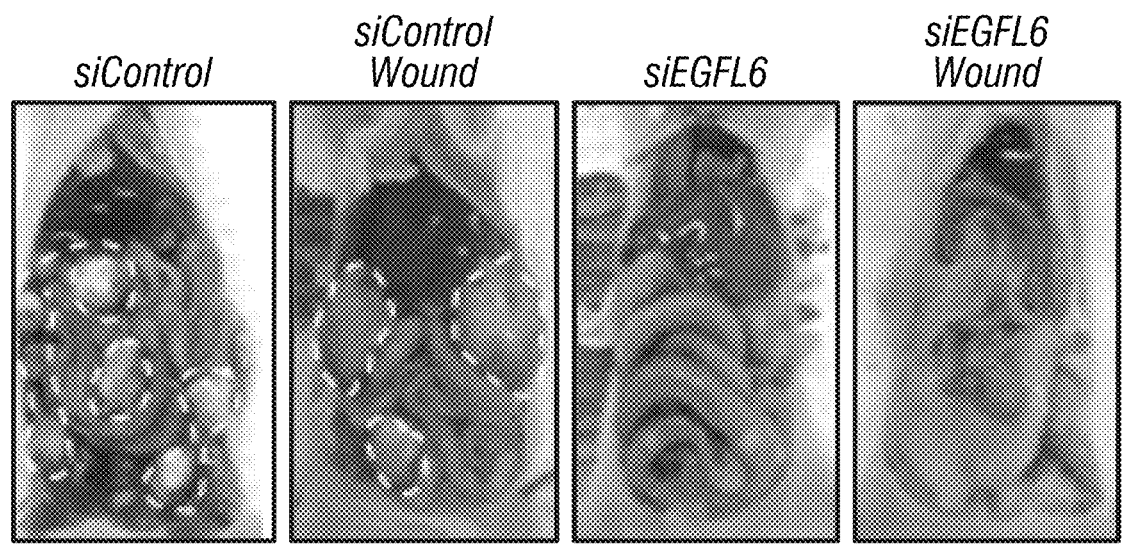
Figure 5G:
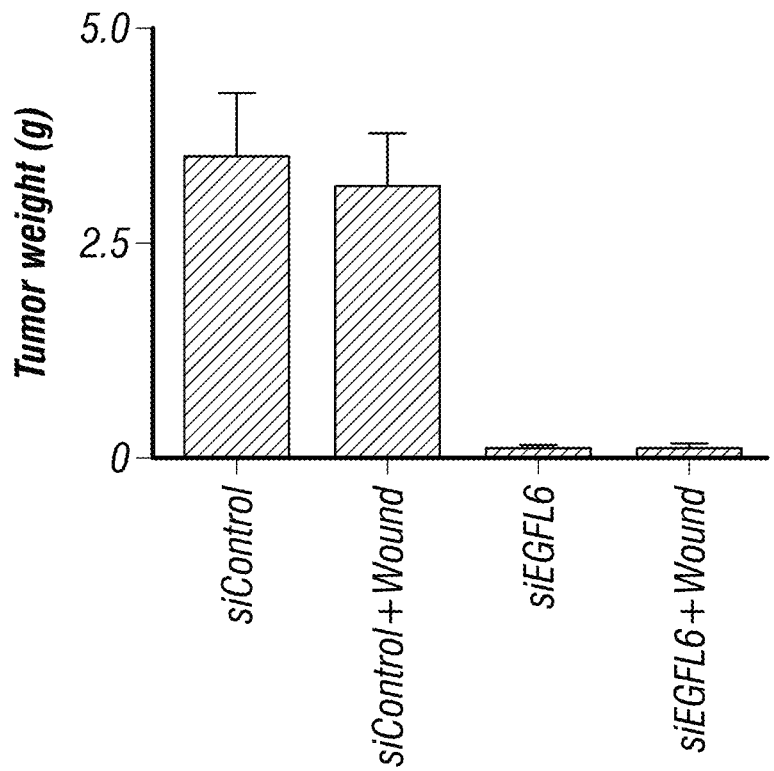
Figure 5H:
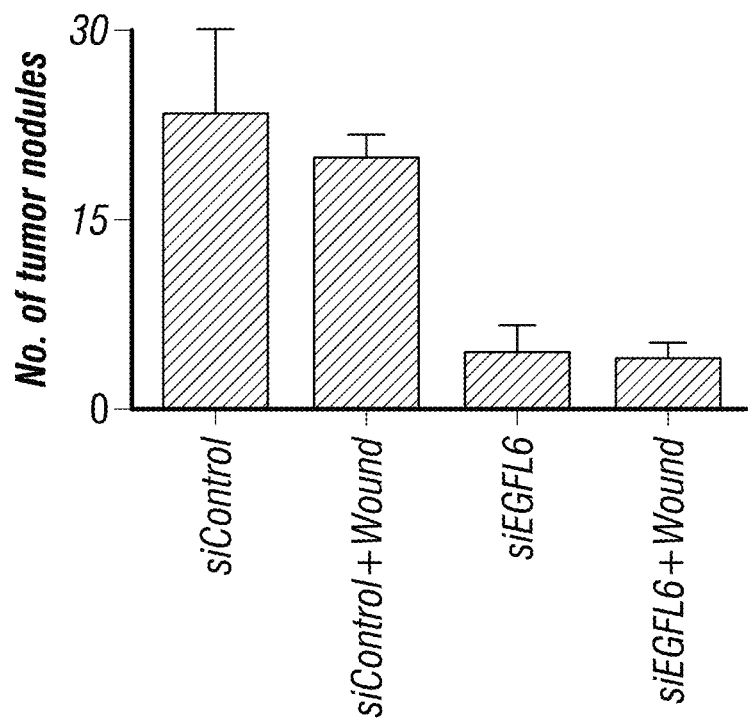

However, animals treated with mouse EGFL6 siRNA showed a significant reduction in tumor burden (FIGS. 5F-5H), suggesting that silencing of EGFL6 in the endothelial cell compartment significantly affects tumor growth but does not compromise wound healing. EGFL6 gene silencing also resulted in significant reduction in proliferation of tumor blood vessels (FIGS. 11A-11B).

Example 6—EGFL6 Enhances Angiogenesis in Endothelial Cells

Figure 6A:
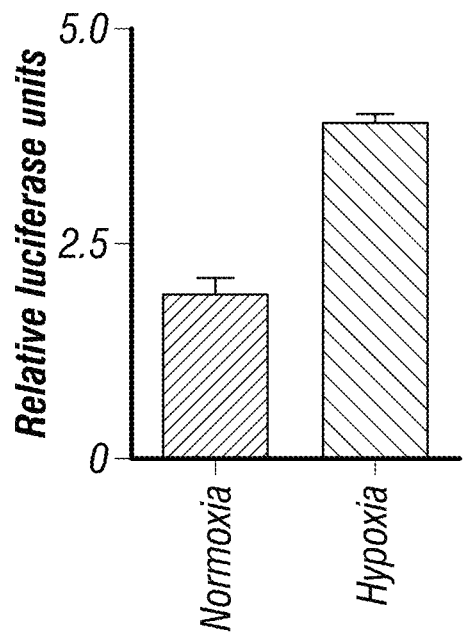
FIGS. 6A-K. TWIST1 induces EGFL6 expression in hypoxia. A,B) EGFL6 promoter reporter analysis under normoxia and hypoxic condition. C) TWIST1 Increases the expression of EGFL6 under hypoxic condition D) TWIST1 binds to promoter region of EGFL6. E and F) Ectopic expression of TWIST1 increases EGFL6 expression in RF24 cells. G) ChIP analysis of TWIST1 binding to EGFL6 promoter region in hypoxia compared to normoxia. EGFL6 and a ChIP assay of TWIST1 binding to EGFL6 promoter in human ovarian endothelial cells (RF24). Cross-linked chromatin from RF24 cells treated with TWIST1 and immunoprecipitated with EGFL6 or IgG control antibodies. The input and immunoprecipitated DNA was subjected to PCR using primers corresponding to the base pairs upstream of EGFL6 transcription start site. PCR products were examined on ethidium bromide-stained agarose gel. H) EGFL6 gene silencing using siRNA leads to increased cell death in hypoxia condition. I) Hind limb ischemia. After arterial ligation, the femoral artery was excised and mice were separated into 3 groups (n=5): normal, ischemia-24 h and ischemia-96 h. Blood flow was monitored before and after femoral artery ligation using serial laser Doppler. At each time point, tissue was harvested and frozen to perform immunofluorescence. J,K) EGFL6 expression was increased in endothelial cells in ischemic (hypoxic) condition compared to normal condition.
Figure 6B:
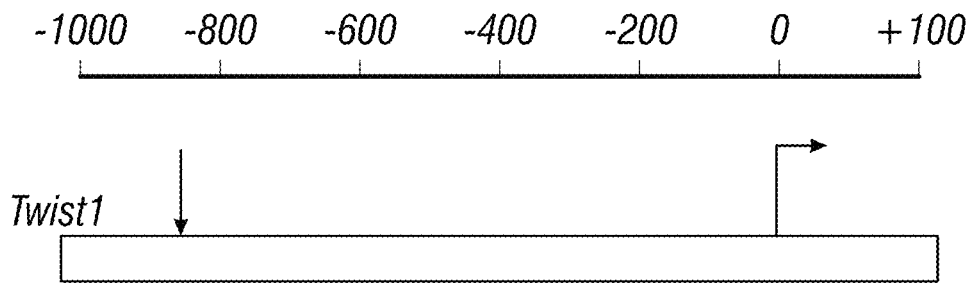
Figure 6C:
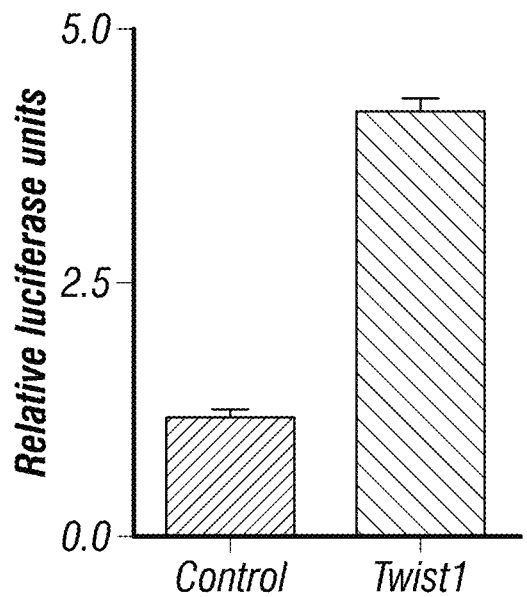
Figure 6D:
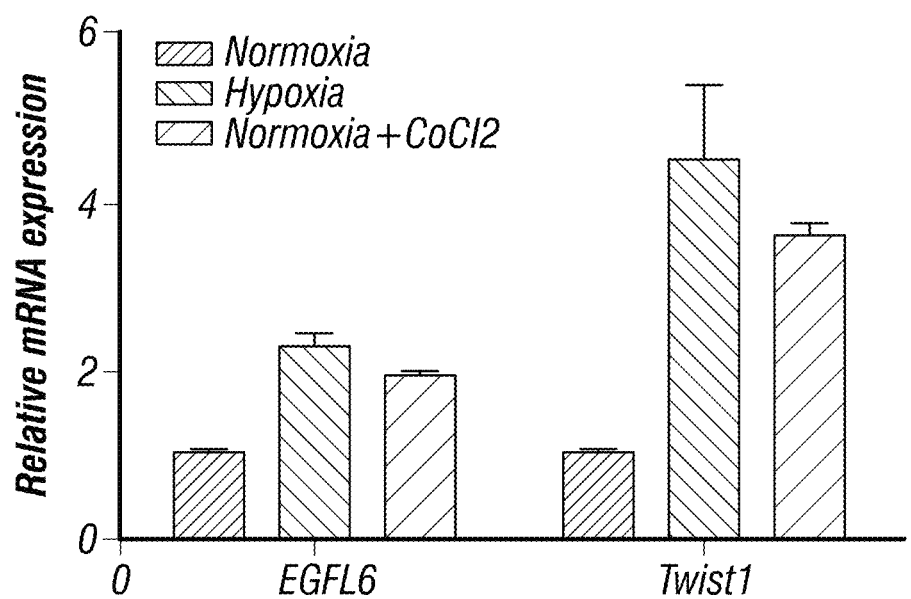
Figure 6E:
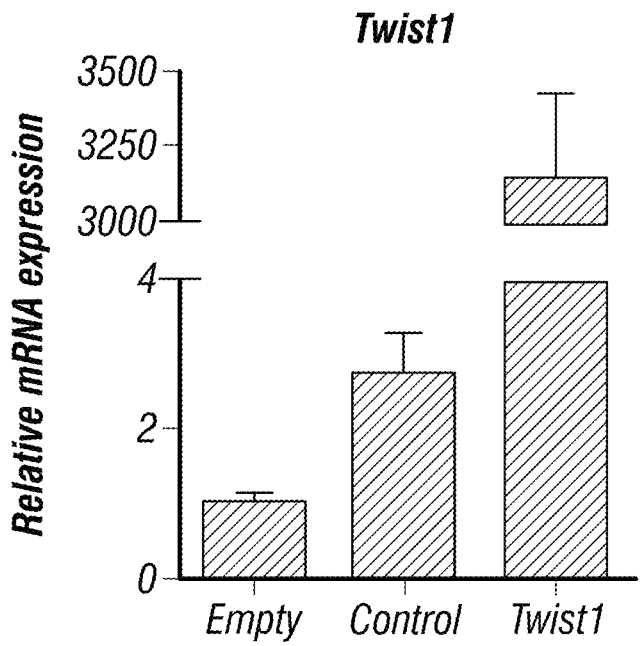
Figure 6F:
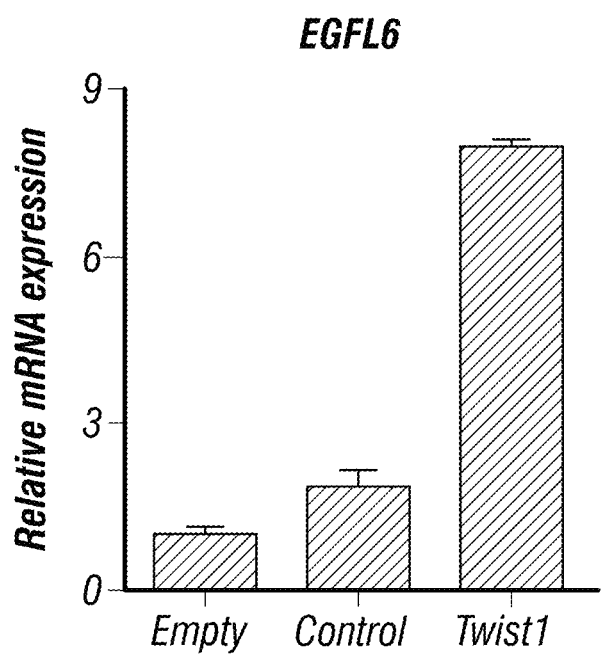
Figure 6G:
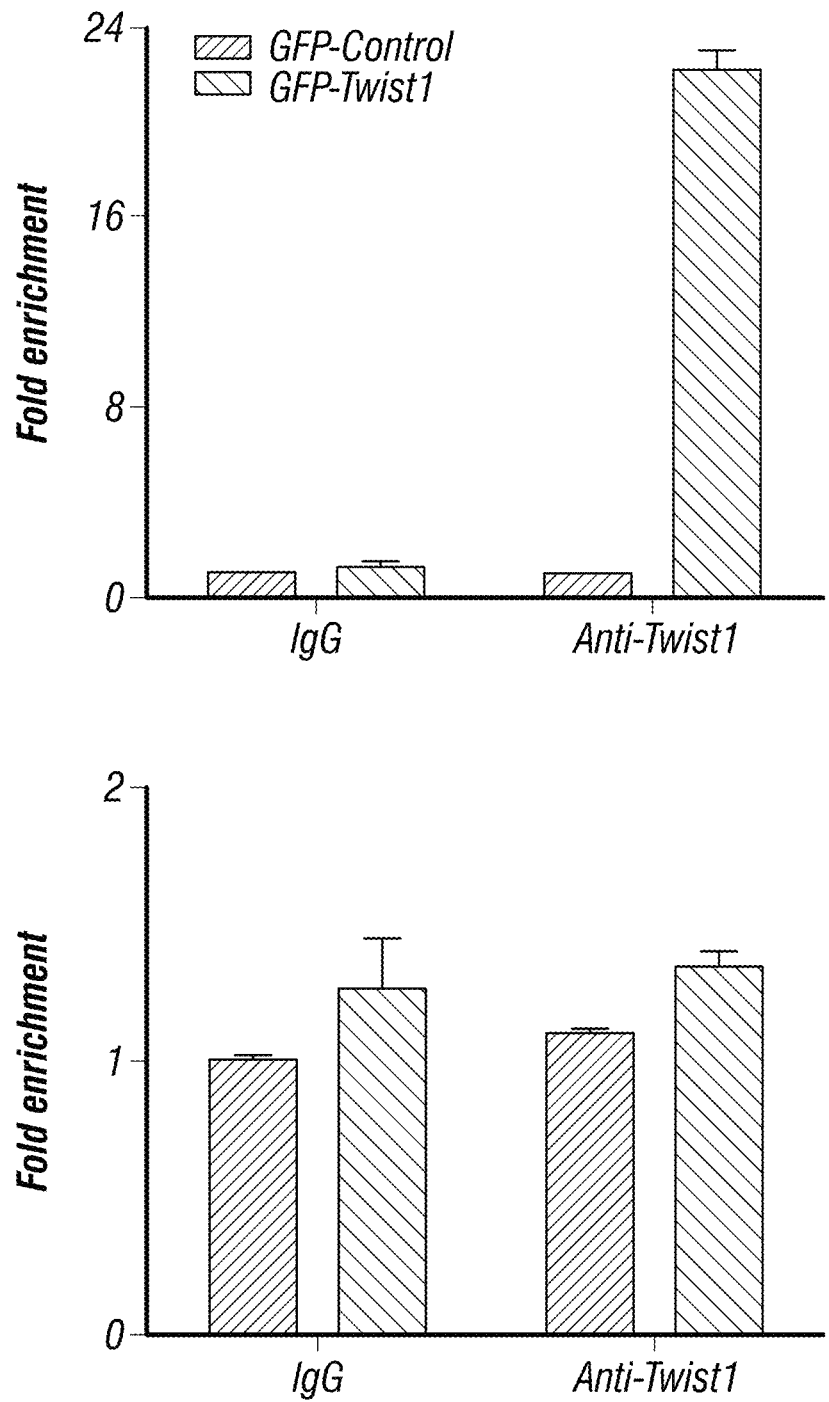
Figure 6H:
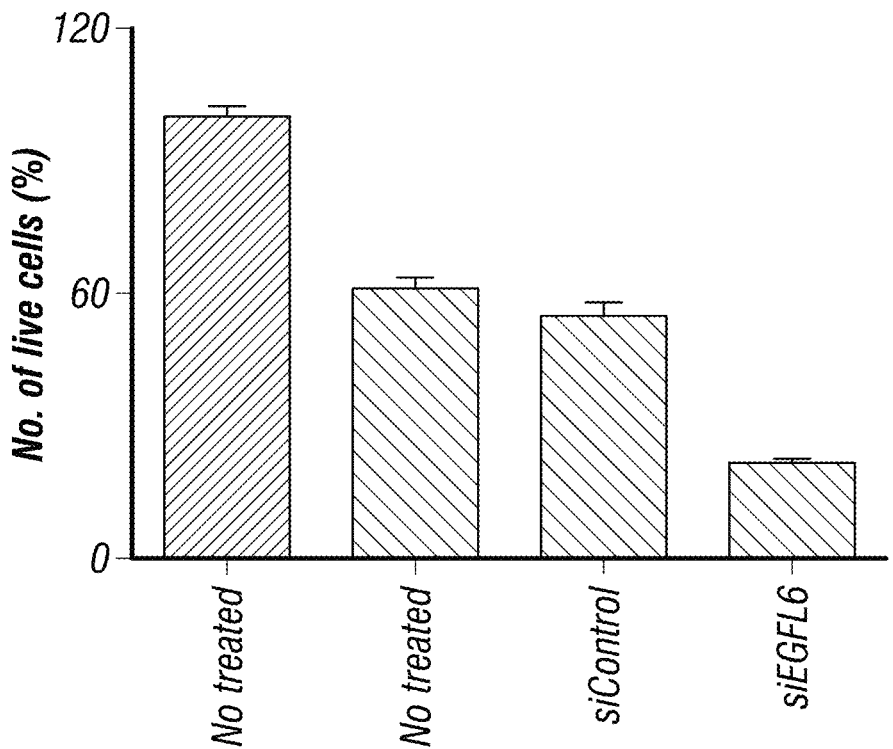
Figure 6I:
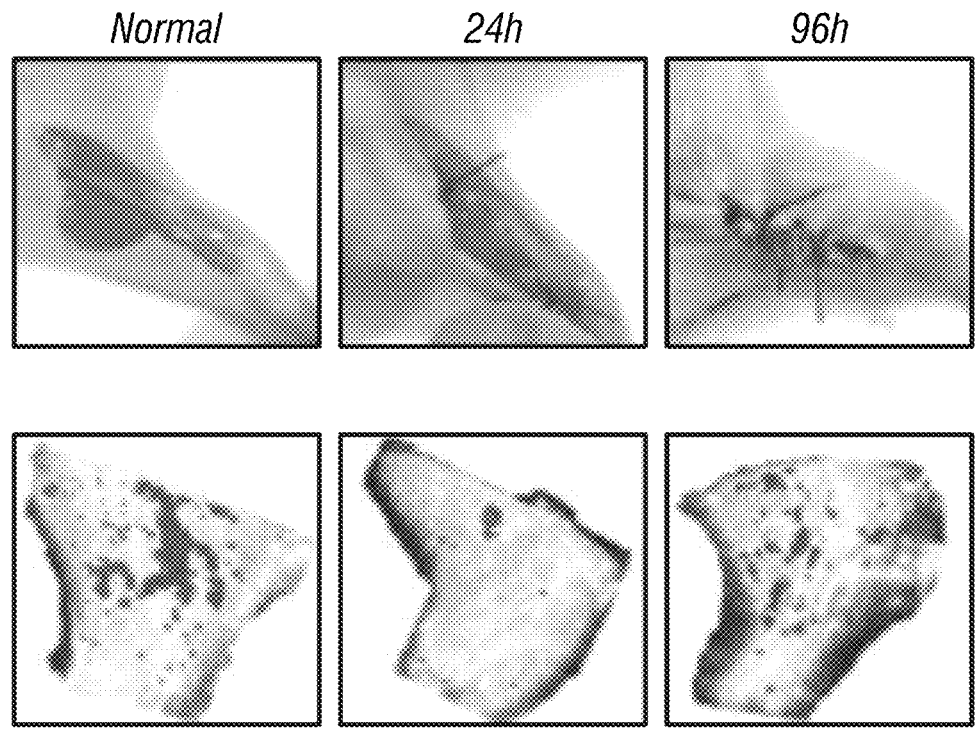
Figure 6J:
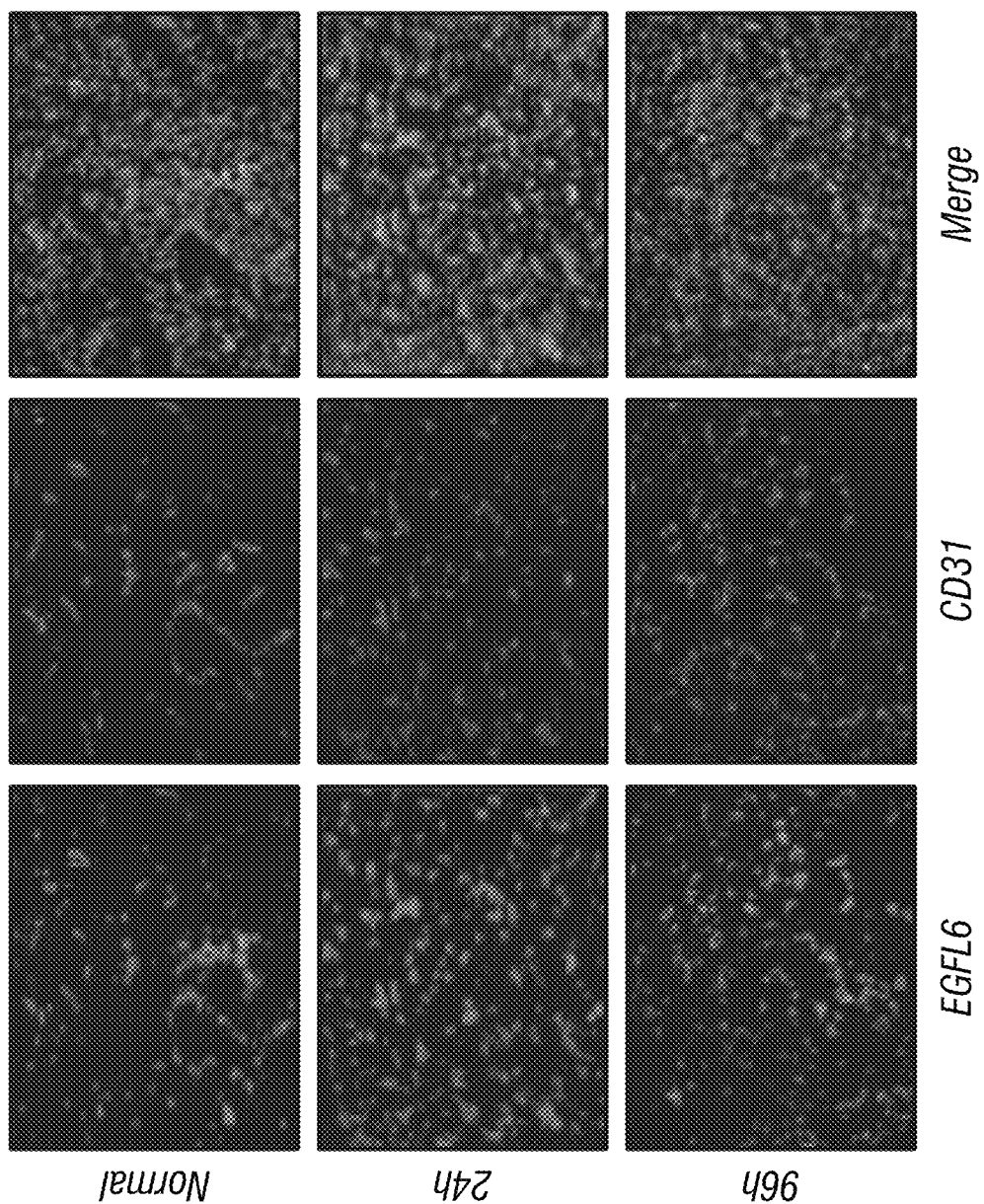
Figure 6K:
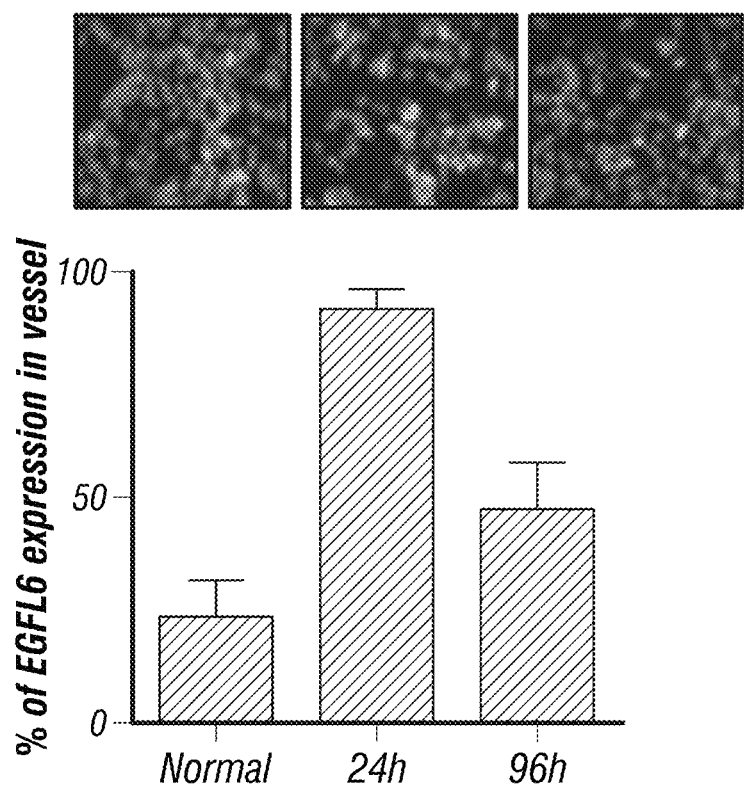
Figure 7A:
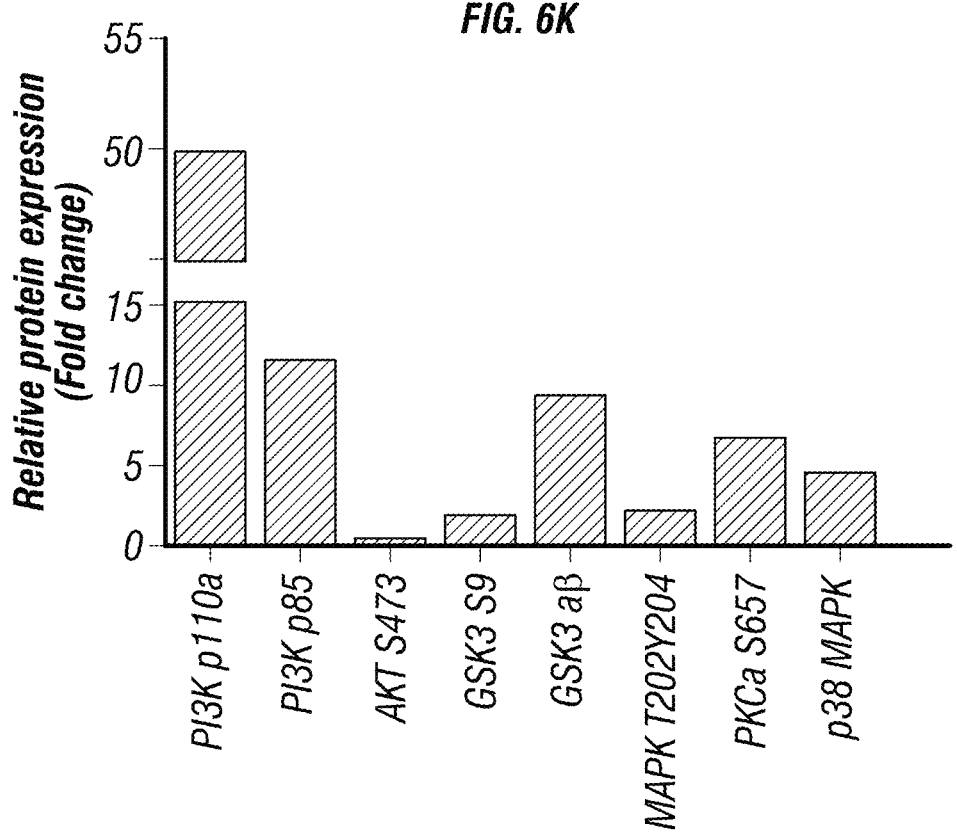
Figure 7H:
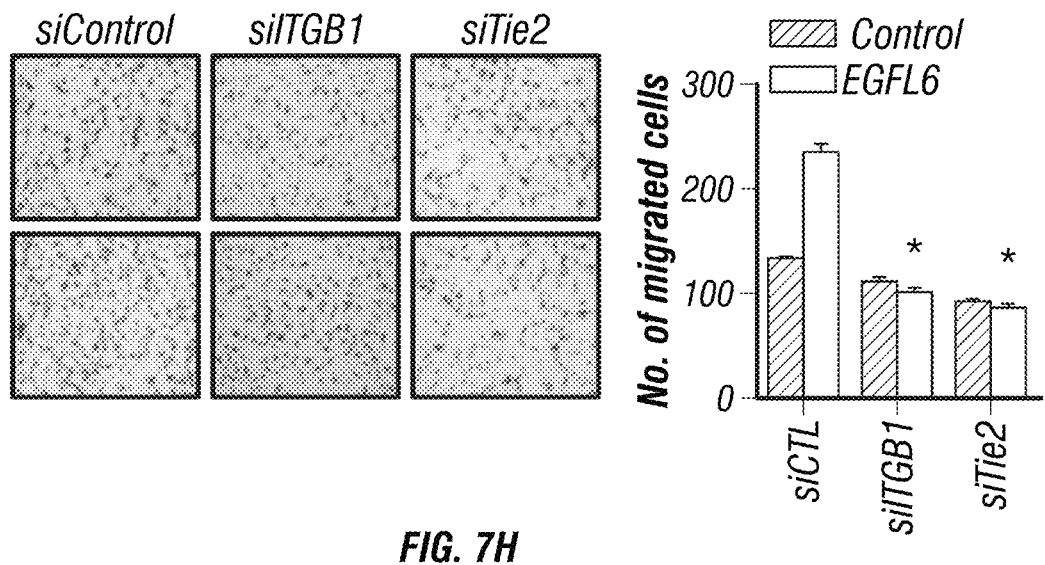
Figure 7I:
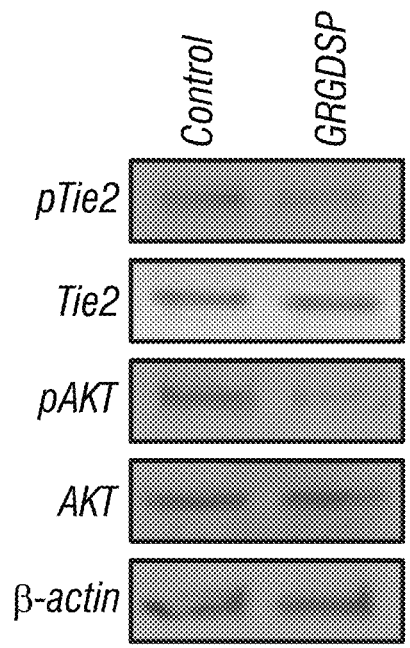
Figure 7J:
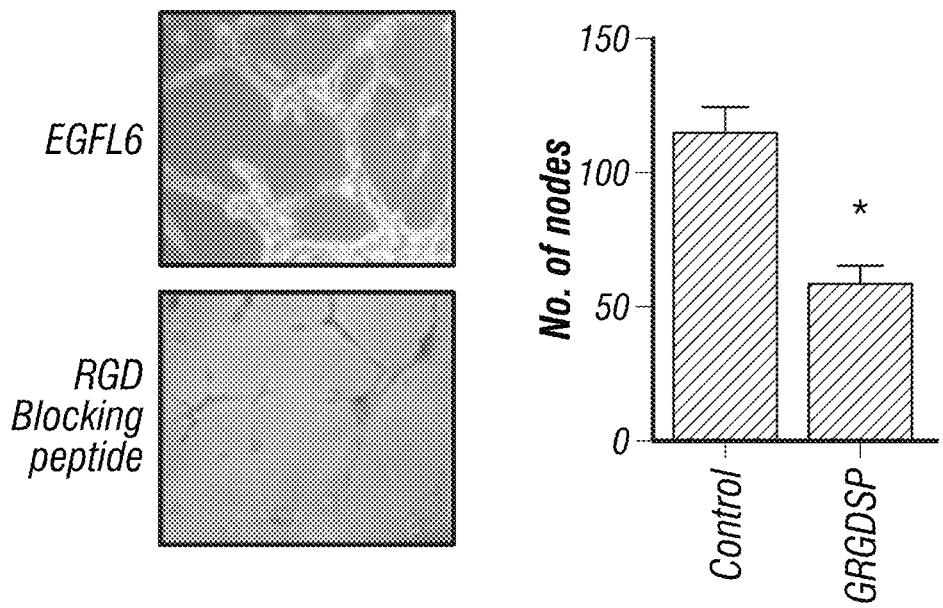
Figure 7K:
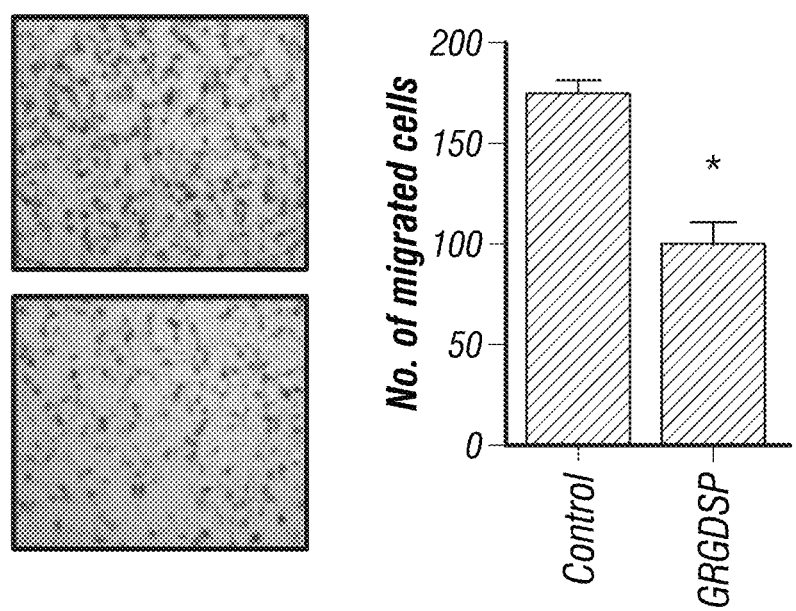
Figure 12A:
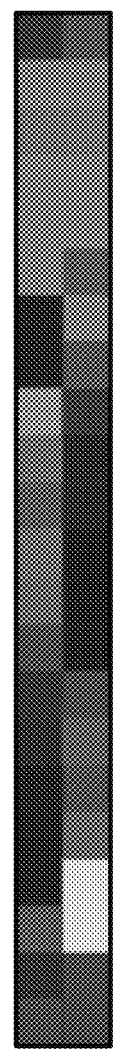
FIGS. 12A-D. Treatment of endothelial cells with EGFL6 activates PI3K/AKT signaling. A) Heat map representation of RPPA analysis showing protein expression change in Control and EGFL6-treated RF24 endothelial cells. B) Heat map representation of RPPA analysis showing protein expression change in control and EGFL6-treated RMG2 ovarian cancer cells. C), D) EGFL6-mediated migration and tube formation (lower panel) reduced by PI3K inhibition in endothelial cells.
Figure 12B:
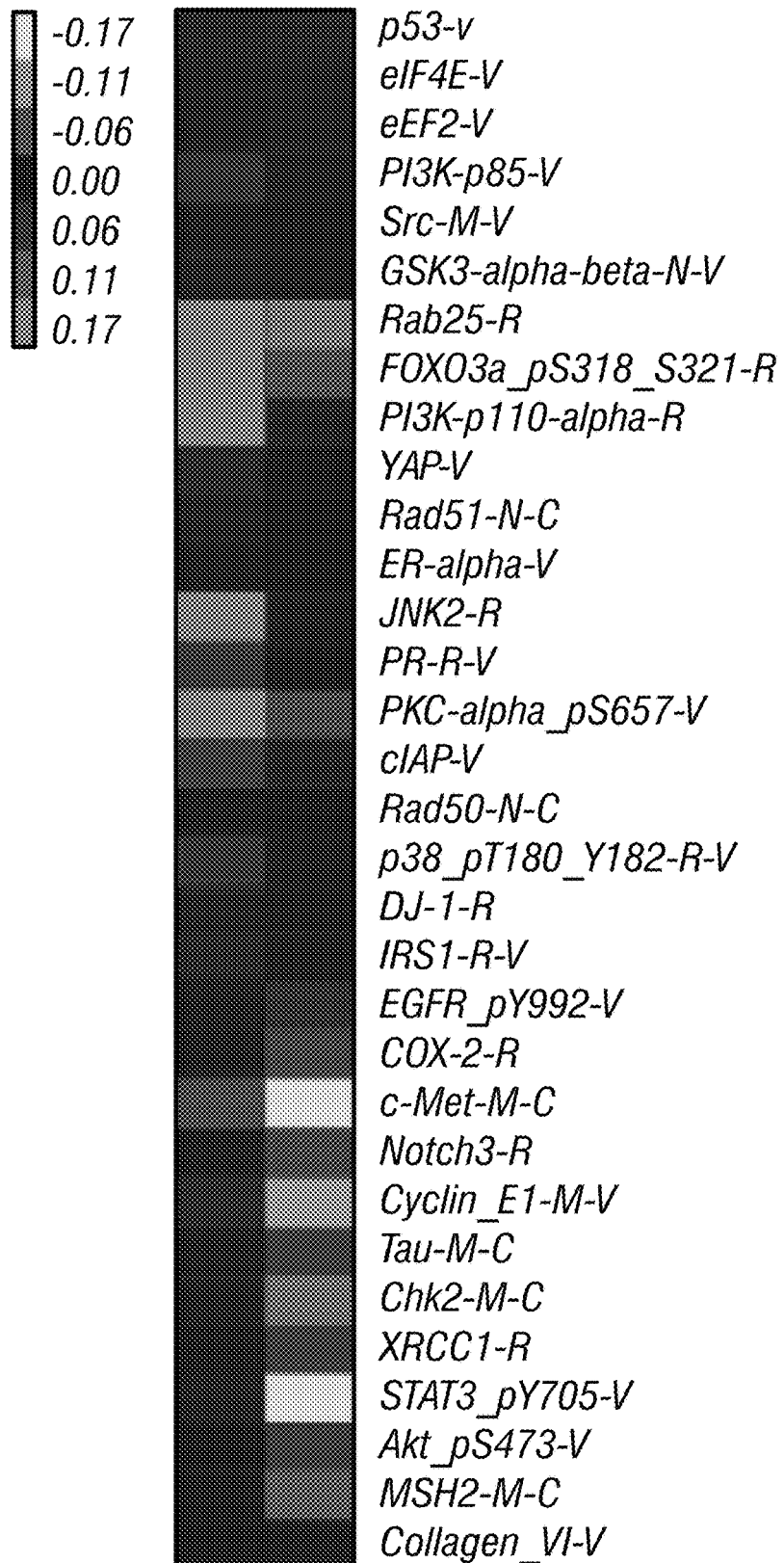
Figure 12C:
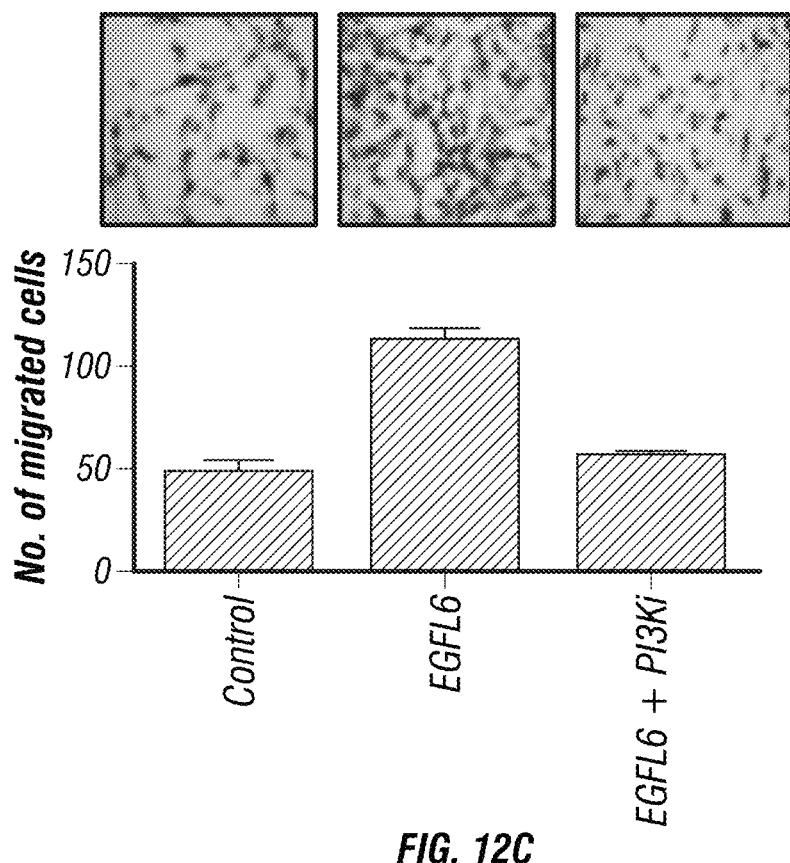
Figure 12D:
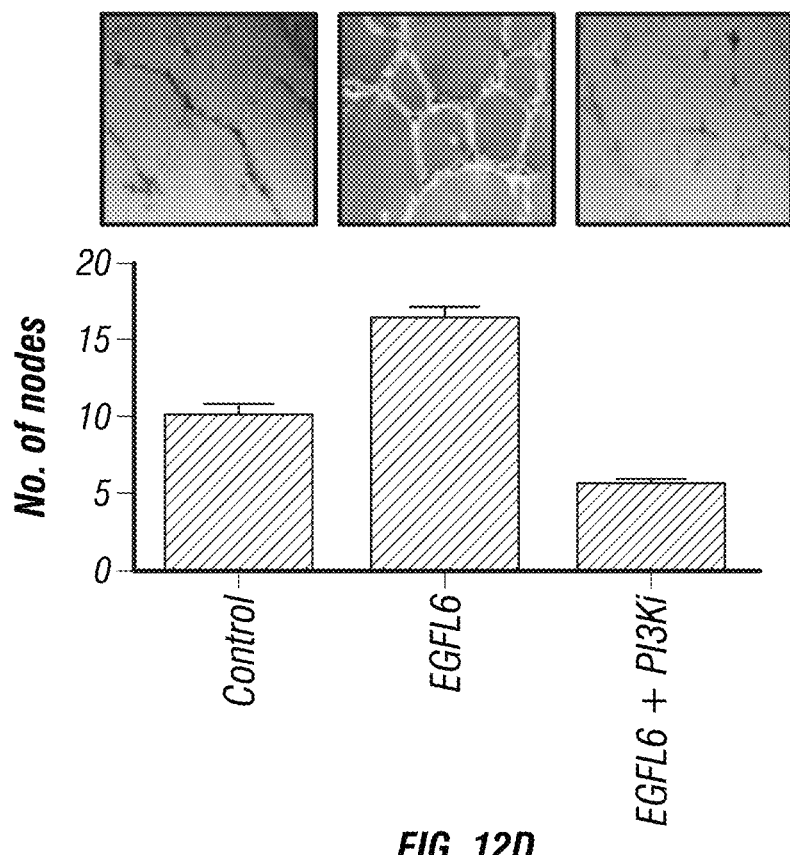

To establish that EGFL6 leads to increased survival of endothelial cells under hypoxic conditions, EGFL6 was silenced in hypoxic RF24 cells in hypoxia using EGFL6 siRNA and cell death was examined. As shown in FIG. 6A, almost 50% of the cells survived hypoxia even after 5 days compared to normoxia. In contrast to this, EGFL6 gene silencing in hypoxia resulted in 75% cell death compared to untreated cells under hypoxia and normoxia condition (FIG. 6H). hind limb ischemia was created in mice by excising the femoral artery on the hind limb of the mouse, which resulted in shut off of blood and oxygen supply to the hind limb (FIG. 6I). As shown in FIG. 6J-6K, ischemic mice showed significant reduction in MVD (blood vessels) and increase in EGFL6 expression in endothelial cells. The migration (FIG. 12C) and tube formation (FIG. 12D) of RF24 cells increased after treatment with EGFL6.

Example 7—EGFL6 Silencing Inhibits Tumor Growth and Angiogenesis

The therapeutic efficacy of EGFL6 in gene silencing was studied using two orthotopic ovarian cancer tumor models, SKOV3ip1 and OVCAR5. Female athymic nude mice (NCr-nu) were purchased from the NCI-Frederick Cancer Research and Development Center (Frederick, MD) and all mouse studies were approved by the Institutional Animal Care and Use Committee. Mice were cared for in accordance with guidelines set forth by the American Association for Accreditation of Laboratory Animal Care and the US Public Health Service Policy on Human Care and Use of Laboratory Animals. For tumor cells injection, SKOV3ip1 cells ($1\times10^6$) were injected through intra peritoneal (i.p) route. For antibody treatment groups, purified monoclonal antibody was dosed weekly for 5 weeks at 5 mg/kg body weight. At the time of sacrifice, mouse and tumor weight, number and distribution of tumors were recorded. Individuals who performed the necropsies were blinded to the treatment group assignments. Tissue specimens were fixed either with formalin, OCT (Miles, Inc., Elkhart, ID) or snap frozen in liquid nitrogen.

Figure 8H:
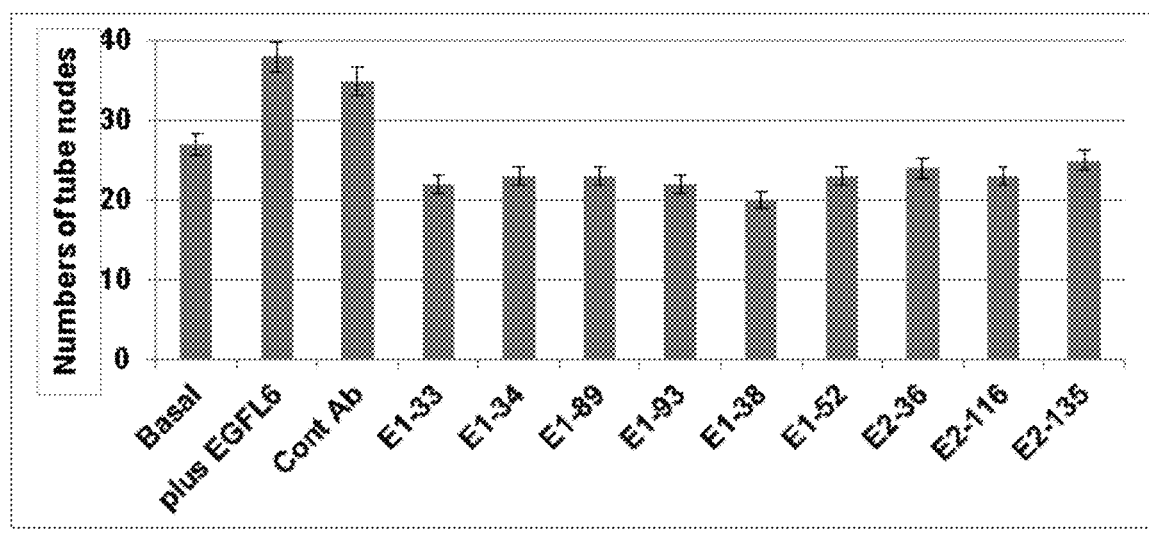
FIG. 8H. Inhibition of tube formation of endothelial cells (RF24) by EGFL6 antibodies. Antibodies (at 5 Dg/ml concentration) were added to the cell culture (RF24) in comparison with a control antibody. The number of tubes was counted after 48 hour treatment in a 96-well assay plate.

As shown in FIG. 8F, treatment of SKOV3ip1 tumor bearing animals with mouse EGFL6 siRNA alone and in combination with human EGFL6 siRNA resulted in a significant reduction in tumor growth as compared to tumor bearing mice that were treated with control siRNA. Human EGFL6 siRNA alone did not have much effect on tumor reduction. The effect of EGFL6 on the number of tumor nodules and observed tumor burden are shown in FIG. 8F. OVCAR5 tumor bearing mice treated with mouse EGFL6 siRNA alone and in combination with human EGFL6 siRNA also showed significant reduction in tumor weight and nodules.

SKOV3ip1 tumor bearing animals treated with mEGFL6 siRNA and the combination of mouse and human EGFL6siRNA showed a significant reduction in proliferating cells and microvessel density as compared to animals treated with the control siRNA (FIGS. 8C-8D). OVCAR5 tumor bearing animals also showed similar results. To determine the off-target effects of mouse EGFL6 siRNA sequences, the effect of EGFL6 gene silencing on SKOV3ip1 tumor growth was checked using two other mouse siRNA sequences and both sequences showed substantial reduction in tumor growth and tumor nodules.

Treatments with anti-EGFL6 antibodies Mab #135 and #93 (E2-135 & E2-93) greatly suppressed tumor growth (FIG. 8F) and only residue cancer cells were detected in EGFL6 antibody treated mice, but un-treated control mice had large tumor load and tumor spread as indicated as number of tumor nodules. Treatment with anti-EGFL6 antibodies (Mab E2-93 and E2-135) also inhibited cancer cell proliferation (Ki67 staining) and reduced micro-vasculature density (tumor angiogenesis, CD31 IHC staining) when compared to the control antibody treated groups (FIG. 8G).

Example 8—Anti-EGFL6 Blocking Antibody Reduces Angiogenesis in Endothelial Cells To demonstrate that EGFL6 blocking would affect its angiogenic mediated functions an EGFL6 functional blocking antibody was developed and tested for its activity on angiogenesis. Several EGFL6 antibody clones bound to human and mouse EGFL6 were screened with comparable affinities. Two antibodies (93 and 135) met all binding affinity and in vitro activity criteria were chosen to carry out for further studies. As shown in FIG. 8B, treatment of endothelial cells with EGFL6 recombinant protein increased the expression of both phosphorylated Tie2 and AKT proteins. In contrast to this, EGFL6 blocking antibodies 93 and 135 resulted in reduction in expression of both phosphorylated proteins. As shown in FIGS. 8D-E, treatment of endothelial cells with EGFL6 recombinant protein enhanced the migration and tube formation in these cells. However, the EGFL6 mediated functional effects of both tube formation and migration was significantly reduced by EGFL6 blocking antibodies.

One of the antibodies was subject to humanization in which it was placed within the human IgG1 backbone to enable use in human cancer patients, and it was demonstrated that the binding affinity and in vitro activities of antibody were preserved after humanization.

Example 9—Anti-EGFL6 Blocking Antibody had Anti-Angiogenesis and Anti-Tumor Effects in Ovarian Cancer Models The in vitro activity of EGFL6 reported above indicated that blocking EGFL6 function would enhance the ability to damage tumor vessels, thereby increasing the anti-tumor efficacy. To test this, the ability of EGFL6 antibody to block the activity of EGFL6 and to inhibit angiogenesis and tumor growth and angiogenesis was investigated.

SKOV3-ip1 tumor-bearing mice were treated with control antibody and anti-EGFL6 antibodies. After 5 weeks of treatment, tumors were harvested and analyzed for anti-tumor and anti-angiogenic activity. Treatments with anti-EGFL6 antibodies resulted in potent anti-tumor activity as compared to treatments with control antibody. Treatment with both anti-EGFL6 antibodies 93 and 135 resulted in significant reduction in tumor weight and tumor nodules (FIGS. 9E and 9F). Animals treated with EGFL6 blocking antibody also showed decreased MVD compared to the control antibody treated groups (FIG. 9F), indicating that blocking EGFL6 activity inhibited tumor growth and angiogenesis. EGFL6 antibody did not prevent wound healing in vitro or in vivo (FIG. 9G), illustrating that it could regulate tumor angiogenesis, without affecting normal tissue repair.

V. ANTIBODY VARIABLE SEQUENCES

Variable DNA sequences of anti-EGFL6 antibodies are shown below.

```
>E1-33H
                                                          (SEQ ID NO: 133)
CAGTCGCTGGAGGAGTCCGAGGGAGGCCTGGTCCAGCCTGAGGGATCCCTGACACTCACCTGCAAAGCCTCTGGACTCGACC

TCAGTAGCTACTACTACATGTGCTGGGTCCGCCAGGCTCCAGGGAAGGGGCTGGAGTGGATCGCATGCATTTATGCTGGTAG

TAGTGGTAGCACTTACTACGCGAGCTGGGCGAAAGGCCGATTCACCATCTCCAAAACCTCGTCGACCACGGTGACTCTGCAA

ATGACCAGTCTGACAGCCGCGGACACGGCCACCTATTTCTGTGCGAGAGGTGGTGGTAGTACTTATGCTCAATATTTTAACT

TGTGGGGCCCAGGCACCCTGGTCACCATCTCCTCAG

>E1-33K
                                                          (SEQ ID NO: 134)
GAGCTCGATATGACCCANACACCAGCCTCCGTGTCTGCAGCTGTGGGAGGCACAGTCAGCATCAATTGCCAGTCCAGTCCGA

GTGTTTATAGGCACTACTTATCCTGGTATCAGCAGAAACCAGGGCAGCCTCCCAAGCTCCTGATCTACTGGGCTTCCACTCT

GGCATCTGGGGTCCCATCGCGGTTCAGCGGCAGTGGATCTGGGACAGAGTTCACTCTCACCATCAGCGGCGTGCAGTGTGAC

GATGCTGCCACTTACTACTGTGCAGGCGAATATGCTAGTGATAGTGATAATCATTTCGGCGGAGGGACCGAGCTGGAGATCC

TAG

>E1-34H
                                                          (SEQ ID NO: 135)
GAGCAGTCGGTGAAGGAGTCCGGGGGAGGCCTGGTCCAGCCTGAGGGATCCCTGACACTCACCTGCACAGCTTCTGGATTCT

CCTTCAGTAGTATTTATTGGATATGCTGGGTCCGCCAGGCTCCAGGGAAGGGGCTGGAGTTGATCGCATGCATTCAGATTAC

TAGTGGTATCACTTACTACGCGAGCTGGGCGAAAGGCCGATTCACCATCTCCAAAATGTCGTCGACCACGGTGACTCTGCAA

ATGACCAGTCTGACAGTCGCGGACACGGCCACCTATTTCTGTGGGAGAAGGGGATATGGTGCCTATGCTGGTACTGGTGCCT

CTGACTTGTGGGGCCCAGGCACCCTGGTCACCGTCTCTTCAG

>E1-34K
                                                          (SEQ ID NO: 136)
GAGCTCGATCTGACCCAGACTGCATCGTCCGTGTCTGCAGCTGTGGGAGGCACCGTCACCATCAATTGCCAGTCCAGTCAGA

GTGTTTATAATAACAACAACTTAGCCTGGTATCAGCAGAAACCAGGGCAGCCTCCCAAGCTCCTGATCTACGAAGCATCCAA
```

```
ACTGGCATCTGGGGTCCCATCGCGGTTCAAAGGCAGTGGATCTGGGACACAGTTCACTCTCACCATCAGCGGCGTGCAGTGT

GACGATGCTGCCACTTACTATTGTGCAGGCGGTTATGCTGGCTACATTTGGGCTTTCGGCGGAGGGACCGAGGTGGTGGTCA

AAG
```

>E1-80H
(SEQ ID NO: 137)
```
GAGCAGTCGGTGGAGGAGTCCGGGGGAGGCCTGTTCCAGCCTGGGGGATCCCTGGCACTCACCTGCAAAGCCTCTGGATTCA

CCCTCAATAGTTATTATATGTCCTGGGTCCGCCAGGCTCCAGGGAAGGGGCTGGAGTGGATCGGATGCATTGATAGTGATAG

TCCTACTACGACTGCCTACGCGAACTGGGCGAGAGGCCGATTCACCATCTCCAAGACCTCGTCGACCACGGTGACTCTGCAA

ATGACCAGTCTGACAGCCGCGGACACGGCCACCTATTTCTGTGCGAGAGGCTATGGTCCTGTTCGATTGGATCTCTGGGGCC

AGGGCACCCTGGTCACCGTCTCTTCAG
```

>E1-80K
(SEQ ID NO: 138)
```
ACCCAGACACCAGCCTCCGTGTCTGCAGCTGTGGGAGGCACAGTCAGCATCAATTGCCAGTCCAGTCAGAGTGTTTATAAGA

ACGCCTATTTATCCTACTACTTAGCCTGGTATCAGCAGAAACCAGGGCAGCCTCCCAAGCTCCTGATCTACTGGGCTTCCAC

TCTGGCATCTGGGGTCCCATCGCGGTTCAAAGGCAGTGGATCTGGGACACAGTTCACTCTCACCATCAGCGACGTGCAGTGT

GACGATGCTGCCACTTACTACTGTGCAGCCAATATAGTAATGATAGTGATAATGGTTTCGGCGGAGGGACCGAGGTGGAAA

TCAAAG
```

>E1-9H
(SEQ ID NO: 139)
```
GAGCAGTCGTTGGAGGAGTCCGGGGGAGACCTGGTCAAGCCTGAGGGATCCCTGACACTCACCTGCGCAGCCTCTGGATTCT

CCTTCAGTAGCGGCTACTGGATATGCTGGGTCCGCCAGGCTCCAGGGAAGGGGCTGGAGTGGATCGGATGCATTTATGCTGG

TAGTAGTGGTGGGCACATTTATTACGCGACCTGGGCGAAAGGCCGATTCACCATCTCCCAAACCTCGTCGACCACGGTGACT

CTGCAAATGACCAGTCTGACAGCCGCGGACACGGCCACATATTTCTGTACAAGAGATAATTATGGTGGTGGTGGTTCTGCTT

CCAAATTGTGGGGCCCAGGCACCCTGGTCACCATCTCTTCAG
```

>E1-89K
(SEQ ID NO: 140)
```
GAGCTCGTGATGACCCAGACTCCATCCCCCGTGTCTGCAGCTGTGGGAGGCACAGTCACCATCAACTGCCAGTCCAGTCAGA

GTGTTTATAGTAACAACCGCTTAGCCTGGTATCAGCAGAAACCAGGGCAGCCTCCCAAGCTCCTGGTCTATTATGCAGCCAC

TCTGGCATCTGGGGTCCCGTCGCGGTTCAAAGGCAGTGGATATGGGACACAGTCCACTCTCACCATCGCCGATGGTGTGT

GACGATGCTGCCACTTACTACTGTGCAGGATATAAAACTGCTGATTCTGATGGTATTGCTTTCGGCGGAGGGACCGAGGTGG

AAATCAAAG
```

>E2-93H
(SEQ ID NO: 141)
```
CAGTCGGTGAAGGAGTCCGAGGGAGGCCTGGTCCAGCCTGAGGGATCCCTGACACTCACCTGCAAAGCCTCTGGATTCTCCT

TCAGTAGTTATGGAGTGAACTGGGTCCGCCAGGCTCCAGGGAAGGGGCTGGAGTGGATCGCGTATATTGGTCTTAGTAGTGA

GATCACTTACTACGCGGGCTGGGCGAAAGGCCGATTCACCATCTCCAAGCCCTCGTCGACCACGGTGACTCTGCAAATGACC

AGTCTGACAGCCGCGGACACGGCCACCTATTTCTGTGTGAGAGATCTTTATCATAGTAATGGTTTGTGGGGCCCAGGCACCC

TGGTCACCATCTCTTCAG
```

>E2-93K
(SEQ ID NO: 142)
```
GAGCTCGATCTGACCCAGACTCCATCCCCCGTGTCTGCAGCTGTGGGAGGCACAGTCACCGTCAGTTGCCAGGCCAGTGAGA

GCGTTTATAATAATAACCGCTTATCCTGGTATCAGCAGAAACCAGGGCAGCCTCCCAAGCTCCTGATCTATTATGCATCCAC

TCTGGCATCTGGGGTCCCATCGCGGTTCAGCGGCAGTGGATCTGGGACACAGTTCACTCTCACCATCAGCAGCGTGCAATGT

GCTGATGCTGCCACGTATTATTGTGTAGCCTTTAAAGGTTATGGTACTGACGGCAATGCTTTCGGCGGAGGGACCGAGGTGG

AAATCAAAG
```

-continued

>E1-38H (SEQ ID NO: 143)
GAGCAGTCGGTGAAGGAGTCCGGGGGAGACCTGGTCAAGCCTGAGGGATCCCTGACACTCACCTGCACAGCCTCTGGATTCT
CCTTCAATAGCGGCTACTGGGTATGCTGGGTCCGCCAGGCTCCAGGGAAGGGGCTGGAGTGGATCGCTTGCATCTATACTAG
TAGTCCTACTGGTGCCATATACTACGCGACCTGGGCGAAAGGCCGATTCACCATCTCCCAAACCTCGTCGACCACGGTGACT
CTGCAAATGACCAGTCTGACAGCCGCGGACACGGCCACCTATTTCTGTACAAGAGATAATTTTGGTGGTGGTGGTTCTGCTT
CCAAATTGTGGGGCCCAGGCACCCTGGTCACCATCTCTTCAG

>E1-38K (SEQ ID NO: 144)
GAGCTCGTGATGACCCAGACTCCATCTTCCAAGTCTGTCCCTGTGGGAGGCACAGTCACCATCGATTGCCAGGCCAGTGAGA
GTGTTTATAGTAACAACCGCTGTGCCTGGTATCAGCAGAAACCAGGGCAGCCTCCCAAGCTCCTGATCTATTATGCATCCAC
TCTGGCATCTGGGGTCCCGTCGCGGTTCAAATGCAGTGGATCTGGGACACGGTTCACTCTCACCATCAGCGGCGTGCAGTGT
GAAGATGCTGCCACTTACTACTGTGCAGGATATAAGACTGCCGATTCTGATGGTCTTGGTTTCGGCGGAGGGACCGAGGTGG
AAATCAAA

>E1-52H (SEQ ID NO: 145)
GAGCAGTCGGTGAAGGAGTCCGAGGGAGACCTGGTCAAGCCTGAGGGATCCCTGACACTCGCCTGCACAGCTTCTGGATTCA
CCCTCAGTAGCTACTACATGTGCTGGGTCCGCCAGGCTCCAGGGAAGGGGCTGGAATGGATCGCATGCATTGATACTGATAA
TGATATTAGGACTGCCTACGCGAGCTGGGCGAGGGGCCGATTCACCATCTCCAGGACCTCGTCGACCACGGTGACTCTGCAA
ATGACCAGTCTGACAGCCGCGGACACGGCCACCTATTTCTGTGGGAGAGGCTATGGTGCGCTTCGGTTGGATCTCTGGGGCC
AGGGCCCCTGGTCACCGTCTCTTCAG

>E1-2K (SEQ ID NO: 146)
GAGCTCGATCTGACCCAGACACCAGCCTCCGTGTCTGCAGCTGTGGGAGGCACAGTCAGCATCAATTGCCAGTCCAGTCCGA
GTGTTTATAGGCACTACTTATCCTGGTATCAGCAGAAACCAGGGCAGCCTCCCAAGCTCCTGATCTACTGGGCTTCCACTCT
GGCATCTGGGGTCCCATCGCGGTTCAGCGGCAGTGGATCTGGGACAGAGTTCACTCTCACCATCAGCGGCGTGCAGTGTGAC
GATGCTGCCACTTACTACTGTGCAGGCGAATATGCTAGTGATAGTGATAATCATTTCGGCGGAGGGACCGAGGTGGAAATCA
AAG

>E2-36H (SEQ ID NO: 147)
CAGTCGGTGAAGGAGTCCGAGGGTCGCCTGGTCACGCCTGGGACACCCCTGACACTCACCTGCACAGTCTCTGGATTCTCCC
TCAGTAGCTACCACATGGGCTGGGTCCGCCAGGCTCCAGGGAAGGGGCTGGAATACATCGGAATCATTAATAATTATGGTGC
CACATACTACGCGAGCTGGGCAAAAGGCCGATTCACCATCTCCAGAACCTCGACCACGGTGGATCTGAAAATGACCAGTCTG
ACAACCGAGGACACGGCCACCTATTTCTGTGCCAGAAGTCCTGGGATTCCTGGTTATAATTCGTGGGGCCCAGGCACCCTGG
TCACCATCTCCTCAG

>E2-36K (SEQ ID NO: 148)
GAGCTCGATCTGACCCAGACTCCATCTTCCACGTCTGCGGCTGTGGGAGGCACAGTCACCATCAACTGCCAGTCCAGTCAGA
ATGTTTATAGTTACAACCGCTTATCCTGGTTTCAGCAGAAACCAGGGCAGCCTCCCAAGCTCCTGATCTACGAAGCATCCAA
ACTGGCATCTGGGGTCCCATCGCGGTTCAAAGGCAGTGGATCTGGGACACAGTTCACTCTCACCATCAGCGGCGTGCAGTGT
GACGATGCTGCCACTTACTACTGTGCAGGCGGTTATGATTGTAGGAGTTCTGATTGTGATGCTTTCGGCGGAGGGACCGAGG
TGGAAATCAAAC

>E1-95H (SEQ ID NO: 149)
AGCAGTTCGGTGGAGGAGTCCGGGGGAGACCTGGTCAAGCCCGGGGCATCCCTGACACTCACCTGCACAGCCTCTGGATTCT
CCTTCAGTAGCAATTCAATGTGCTGGGTCCGCCAGGCTCCAGGGAAGGGGCTGGAGTGGATCGGATGCATTGCTAGTAGTAG
TAGTCATAGTACTTACTACGCGAGCTGGGCGAAAGGCCGATTCACCATCTCCAAAACCTCGTCGACCACGGTGACTCTGCAA

ATGACCAGTCTGACAGCCGCGGACATGGCCACCTATTTCTGTGCGAGAGATTCTGGTAATCGTGGTTACCTTTATGCGGCG

ACTTTAACTTGTGGGGCCCAGGCACCCTGGTCACCGTCTCTTCAG

>E1-95K                                                                    (SEQ ID NO: 150)
GAGCTCGTGCTGACCCAGACTCCAGCCTCTGTGGAGGTAGCTGTGGGAGGCACAGTCACCATCAATTGCCAGGCCAGTCAGA

GCATTAATAGTTGGTTATCCTGGTATCAGCAGAAACCAGGGCAGCGTCCCAAACTCCTGATCTACGAAGCATCCACTCTGGC

ATCTGGGGTCTCATCGCGGTTCAGTGGCAGTGGATCTGGGACACAGTTCACTCTCACCATCAGCGGCGTGCAGTGTGACGAT

GCTGCCACTTACTACTGTCAACAGGGTTATAGTTATAGTAATGTTGATAATAATATTTTCGGCGGAGGGACCGAGGTGGTGG

TCAAAG

>E2-116H                                                                   (SEQ ID NO: 151)
CAGTCGTTGGAGGAGTCCGGGGGAGGCCTGGTCAAGCCTGAGGGATCCCTGACACTCACCTGCACAGCCTCTGGATTCGACC

TCAGTAGCTCCTACTACATGTGCTGGGTCCGCCAGGCTCCAGGGAAGGGGCTGGAGTGGATCGTCTGTATTGACGGTGGTGG

GGGTGAGCCCACTGCCTACCCGAGCTGGGCGAAAGGCCGATTCACCGTCTCCAAAACCTCGTCGACCACGGTGACTCTTCAA

ATGACCAGTCTGACAGTCGCGGACACGGCCACGTATTTCTGTGCGAGACGAGATGCTGGTGCTGGGAACGCCTTTAGCTTGT

GGGGCCCAGGCACCCTGGTCACCATCTCCTCAG

>E2-116K                                                                   (SEQ ID NO: 152)
GAGCTCGATATGACCCAGACTCCATCCCCCGTGTCTGCAGCTGTGGGAGGCACAGTCACCATCAGTTGCCAGTCCAGTCAAA

GTGTTTATCTTCAGAACAACTTAGCCTGGTATCAGCAGAAACCAGGGCAGCCTCCCAAGCTCCTGATCTATTATGCATCCAC

TCTGGCATCTGGGGTCTCATCGCGGTTCAAAGGCAGTGGATCTGGGACACAGTTCACTCTCACCATCAGCGACCTGGAGTGT

GACGATGCTGCCACTTACTACTGTCAGGGCGGTTACAGTGGATATATCAATTCTTTCGGCGGAGGGACCGAGGTGGAAATCA

AAG

>E2-135H                                                                   (SEQ ID NO: 153)
CAGTCGGTGAAGGAGTCCGAGGGAGACCTGGTCAAGCCTGGGGCATCCCTGACACTCACCTGCAAAGCCTCTGGATTCGACT

TCAGTAGCAGCTACTTTATGTGCTGGGTCCGCCAGGCTCCAGGGAGGGGGCTGGAGTGGATCGCATGCATTTATACTGTTAT

TAGTCGTAAGACTTATTACGCGAGCTGGGCGAAAGGCCGATTCACCATCTCCAAAACCTCGGCGACCACGGTGGATCTGCAA

ATGACCAGTCTGACAGCCGCGGACACGGCCACCTATTTCTGTGCGAGATCGGCAACAATTGAAAGATTGGATCTCTGGGGCC

AGGGCACCCTGGTCACCGTCTCCTCAG

>E2-35K                                                                    (SEQ ID NO: 154)
GAGCTCGATCTGACCCAGACTCCATCGCCCGTGTCTGCACCTGTGGGAGGCACAGTCACCATCAATTGCCAGGCCAGTGAGA

GTGTTTATAATAACTACCGCTTATCCTGGTATCAGCAGAAACCAGGGCAGCCTCCCAAGCTCCTAATCTATGCTGCATCCAC

TCTGGCATCTGGGGTCCCATCGCGGTTCAAAGGCAGTGGATCTGGGACACAGTTCACTCTCGCCATCAGCGATGTGGTGTGT

GACGATGCTGCCACTTACTACTGTGTAGGATATAAAAGTGGTTATATTGATAGTATTCCTTTCGGCGGAGGGACCGAGGTGG

TGGTCAAAG

>E1-142H                                                                   (SEQ ID NO: 155)
CAGTCGTTGGAGGAGTCCGGGGGAGACCTGGTCAAGCCTGGGGCATCCCTGACACTCACCTGCACAGCTTCTGGATTCACCA

TCAATAACTACAACATTAACTGGGTCCGCCAGGCTCCAGGGAAGGGGCTGGAGTGGATCGCACGTATTTGGAATGGTGATGG

CAGCACATACTACGCGAGCTGGGCGAAAGGCCGATTCACCATCTCCAAAACCTCGTCGACCACGGTGACTCTACAAATGACC

AGTCTGACAGCCGCGGACACGGCCACCTATTTCTGTGCGAGAAATTTTAACTTGTGGGGCCCAGGCACCCTGGTCACCATCT

CTTCAG

>E1-142K                                                                   (SEQ ID NO: 156)
GAGCTCGTGCTGACCCAGACTCCATCTCCCGTGTCTGCAGCTGTGGGAGGCACAGTCACCATCAATTGCCAGTCCAGTCGCA

GTGTTTATAGTAACAACTACTTATCCTGGTTTCAGCAGAAACCAGGGCAGCCTCCCAAGCCCCTGATCTATTATGCATCCAC

```
TCTGGCATCTGGGGTCCCATCGCGGTTTAAAGGCAGTGGATCTGGGACACAGTTCACTCTCACCATCAGCGACGTGCAGTGT

GACGATGCTGCCACTTACTACTGTGCAGGCGATTATAGTAGTAGTAGTGATATGTGTATTTTCGGCGGAGGGACCGAGCTGG

AAATCAAAG
```

Variable amino acid sequences of anti-EGFL6 antibodies are shown below.

>E1-33H
(SEQ ID NO: 157)
QSLEESEGGLVQPEGSLTLTCKASGLDLSSYYYMCWVRQAPGKGLEWIAC
IYAGSSGSTYYASWAKGRFTISKTSSTTVTLQMTSLTAADTATYFCARGG
GSTYAQYFNLWGPGTLVTISS

>E1-33L
(SEQ ID NO: 158)
ELDMTTPASVSAAVGGTVSINCQSSPSVYRHYLSWYQQKPGQPPKLLIYW
ASTLASGVPSRFSGSGSGTEFTLTISGVQCDDAATYYCAGEYASDSDNHF
GGGTELEIL

>E1-34H
(SEQ ID NO: 159)
EQSVKESGGGLVQPEGSLTLTCTASGFSFSSIYWICWVRQAPGKGLELIA
CIQITSGITYYASWAKGRFTISKMSSTTVTLQMTSLTVADTATYFCGRRG
YGAYAGTGASDLWGPGTLVTVSS

>E1-34L
(SEQ ID NO: 160)
ELDLTQTASSVSAAVGGTVTINCQSSQSVYNNNNLAWYQQKPGQPPKLLI
YEASKLASGVPSRFKGSGSGTQFTLTISGVQCDDAATYYCAGGYAGYIWA
FGGGTEVVVK

>E1-80H
(SEQ ID NO: 161)
EQSVEESGGGLFQPGGSLALTCKASGFTLNSYYMSWVRQAPGKGLEWIGC
IDSDSPTTTAYANWARGRFTISKTSSTTVTLQMTSLTAADTATYFCARGY
GPVRLDLWGQGTLVTVSS

>E1-80LK
(SEQ ID NO: 162)
TQTPASVSAAVGGTVSINCQSSQSVYKNAYLSYYLAWYQQKPGQPPKLLI
YWASTLASGVPSRFKGSGSGTQFTLTISDVQCDDAATYYCAAEYSNDSDN
GFGGGTEVEIK

>E1-89H
(SEQ ID NO: 163)
EQSLEESGGDLVKPEGSLTLTCAASGFSFSSGYWICWVRQAPGKGLEWIG
CIYAGSSGGHIYYATWAKGRFTISQTSSTTVTLQMTSLTAADTATYFCTR
DNYGGGGSASKLWGPGTLVTISS

>E1-89L
(SEQ ID NO: 164)
ELVMTQTPSPVSAAVGGTVTINCQSSQSVYSNNRLAWYQQKPGQPPKLLV
YYAATLASGVPSRFKGSGYGTQSTLTIADVVCDDAATYYCAGYKTADSDG
IAFGGGTEVEIK

>E2-93H
(SEQ ID NO: 165)
QSVKESEGGLVQPEGSLTLTCKASGFSFSSYGVNWVRQAPGKGLEWIAYI
GLSSEITYYAGWAKGRFTISKPSSTTVTLQMTSLTAADTATYFCVRDLYH
SNGLWGPGTLVTISS

>E2-93L
(SEQ ID NO: 166)
ELDLTQTPSPVSAAVGGTVTVSCQASESVYNNNRLSWYQQKPGQPPKLLI
YYASTLASGVPSRFSGSGSGTQFTLTISSVQCADAATYYCVAFKGYGTDG
NAFGGGTEVEIK

>E1-38H
(SEQ ID NO: 167)
EQSVKESGGDLVKPEGSLTLTCTASGFSFNSGYWVCWVRQAPGKGLEWIA
CIYTSSPTGAIYYATWAKGRFTISQTSSTTVTLQMTSLTAADTATYFCTR
DNFGGGGSASKLWGPGTLVTISS

>E1-38L
(SEQ ID NO: 168)
ELVMTQTPSSKSVPVGGTVTIDCQASESVYSNNRCAWYQQKPGQPPKLLI
YYASTLASGVPSRFKCSGSGTRFTLTISGVQCEDAATYYCAGYKTADSDG
LGFGGGTEVEIK

>E1-52H
(SEQ ID NO: 169)
EQSVKESEGDLVKPEGSLTLACTASGFTLSSYYMCWVRQAPGKGLEWIAC
IDTDNDIRTAYASWARGRFTISRTSSTTVTLQMTSLTAADTATYFCGRGY
GALRLDLWGQGTLVTISS

>E1-52L
(SEQ ID NO: 170)
ELDLTQTPASVSAAVGGTVSINCQSSPSVYRHYLSWYQQKPGQPPKLLIY
WASTLASGVPSRFSGSGSGTEFTLTISGVQCDDAATYYCAGEYASDSDNH
FGGGTEVEIK

>E2-36H
(SEQ ID NO: 171)
QSVKESEGRLVTPGTPLTLTCTVSGFSLSSYHMGWVRQAPGKGLEYIGII
NNYGATYYASWAKGRFTISRTSTTVDLKMTSLTTEDTATYFCARSPGIPG
YNSWGPGTLVTISS

>E2-36L
(SEQ ID NO: 172)
ELDLTQTPSSTSAAVGGTVTINCQSSQNVYSYNRLSWFQQKPGQPPKLLI
YEASKLASGVPSRFKGSGSGTQFTLTISGVQCDDAATYYCAGGYDCRSSD
CDAFGGGTEVEIK

```
>E1-95H
                                    (SEQ ID NO: 173)
SSSVEESGGDLVKPGASLTLTCTASGFSFSSNSMCWVRQAPGKGLEWIGC

IASSSSHSTYYASWAKGRFTISKTSSTTVTLQMTSLTAADMATYFCARDS

GNRGYLYAGDFNLWGPGTLVTVSS

>E1-95L
                                    (SEQ ID NO: 174)
ELVLTQTPASVEVAVGGTVTINCQASQSINSWLSWYQQKPGQRPKLLIYE

ASTLASGVSSRFSGSGSGTQFTLTISGVQCDDAATYYCQQGYSYSNVDNN

IFGGGTEVVVK

>E2-116H
                                    (SEQ ID NO: 175)
QSLEESGGGLVKPEGSLTLTCTASGFDLSSSYYMCWVRQAPGKGLEWIVC

IDGGGGEPTAYPSWAKGRFTVSKTSSTTVTLQMTSLTVADTATYFCARRD

AGAGNAFSLWGPGTLVTISS

>E2-116L
                                    (SEQ ID NO: 176)
ELDMTQTPSPVSAAVGGTVTISCQSSQSVYLQNNLAWYQQKPGQPPKLLI

YYASTLASGVSSRFKGSGSGTQFTLTISDLECDDAATYYCQGGYSGYINS

FGGGTEVEIK

>E2-135H
                                    (SEQ ID NO: 177)
QSVKESEGDLVKPGASLTLTCKASGFDFSSSYFMCWVRQAPGRGLEWIAC

IYTVISRKTYYASWAKGRFTISKTSATTVDLQMTSLTAADTATYFCARSA

TIERLDLWGQGTLVTVSS

>E2-135L
                                    (SEQ ID NO: 178)
ELDLTQTPSPVSAPVGGTVTINCQASESVYNNYRLSWYQQKPGQPPKLLI

YAASTLASGVPSRFKGSGSGTQFTLAISDVVCDDAATYYCVGYKSGYIDS

IPFGGGTEVVVK

>E1-142H
                                    (SEQ ID NO: 179)
QSLEESGGDLVKPGASLTLTCTASGFTINNYNINWVRQAPGKGLEWIARI

WNGDGSTYYASWAKGRFTISKTSSTTVTLQMTSLTAADTATYFCARNFNL

WGPGTLVTISS

>E1-142L
                                    (SEQ ID NO: 180)
ELVLTQTPSPVSAAVGGTVTINCQSSASVYSNNYLSWFQQKPGQPPKPLI

YYASTLASGVPSRFKGSGSGTQFTLTISDVQCDDAATYYCAGDYSSSSDM

CIFGGGTELEIK

* * *
```

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Application No. 2002/0172677
U.S. Patent Application No. 2004/0126828
U.S. Patent Application No. 2005/0214860
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,870,287
U.S. Pat. No. 4,938,948
U.S. Pat. No. 4,946,778
U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,739,169
U.S. Pat. No. 5,760,395
U.S. Pat. No. 5,770,376
U.S. Pat. No. 5,789,208
U.S. Pat. No. 5,801,005
U.S. Pat. No. 5,821,337
U.S. Pat. No. 5,824,311
U.S. Pat. No. 5,830,880
U.S. Pat. No. 5,844,091
U.S. Pat. No. 5,846,945
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259

U.S. Pat. No. 6,861,572
U.S. Pat. No. 6,875,434
U.S. Pat. No. 6,881,557
U.S. Pat. No. 6,891,024
U.S. Pat. No. 6,946,646
Ali-Fehmi et al., Expression of cyclooxygenase-2 in advanced stage ovarian serous carcinoma: correlation with tumor cell proliferation, apoptosis, angiogenesis, and survival. American journal of obstetrics and gynecology 192, 819-825, 2005.
Baluk et al., Cellular abnormalities of blood vessels as targets in cancer. Current opinion in genetics & development 15, 102-111, 2005.
Buckanovich et al. Tumor vascular proteins as biomarkers in ovarian cancer. Journal of clinical oncology: official journal of the American Society of Clinical Oncology 25, 852-861, 2007.
Chim et al. EGFL6 promotes endothelial cell migration and angiogenesis through the activation of extracellular signal-regulated kinase. The Journal of biological chemistry 286, 22035-22046, 2011.
Donninger et al., Whole genome expression profiling of advance stage papillary serous ovarian cancer reveals activated pathways. Oncogene 23, 8065-8077, 2004.
Halder et al., Focal adhesion kinase targeting using in vivo short interfering RNA delivery in neutral liposomes for ovarian carcinoma therapy. Clinical cancer research: an official journal of the American Association for Cancer Research 12, 4916-4924, 2006.
Landen et al., Therapeutic EphA2 gene targeting in vivo using neutral liposomal small interfering RNA delivery. Cancer research 65, 6910-6918, 2005.
Langley et al., Tissue-specific microvascular endothelial cell lines from H-2K(b)-tsA58 mice for studies of angiogenesis and metastasis. Cancer Research 63, 2971-2976, 2003.
Lu et al., Gene alterations identified by expression profiling in tumor-associated endothelial cells from invasive ovarian carcinoma. Cancer research 67, 1757-1768, 2007.
Lu et al., Regulation of tumor angiogenesis by EZH2. Cancer cell 18, 185-197, 2010.
Oberauer et al., EGFL6 is increasingly expressed in human obesity and promotes proliferation of adipose tissue-derived stromal vascular cells. Molecular and cellular biochemistry 343, 257-269, 2010.
Sood et al., Molecular determinants of ovarian cancer plasticity. American Journal of Pathology 158, 1279-1288, 2001.
Thaker et al., Chronic stress promotes tumor growth and angiogenesis in a mouse model of ovarian carcinoma. Nature medicine 12, 939-944, 2006.
Yeung et al., Cloning of a novel epidermal growth factor repeat containing gene EGFL6: expressed in tumor and fetal tissues. Genomics 62, 304-307, 1999.

What is claimed is:

1. A method for treating a subject having an ovarian cancer tumor comprising administering an effective amount of a first cancer therapy comprising a monoclonal antibody or antibody fragment that binds specifically to EGFL6 to the subject, wherein said antibody or antibody fragment comprises:
    (a) a first $V_H$ CDR is identical to SEQ ID NO: 64;
    (b) a second $V_H$ CDR is identical to SEQ ID NO: 65;
    (c) a third $V_H$ CDR is identical to SEQ ID NO: 66;
    (d) a first $V_L$ CDR is identical to SEQ ID NO: 126;
    (e) a second $V_L$ CDR is identical to SEQ ID NO: 127; and
    (f) a third $V_L$ CDR is identical to SEQ ID NO: 128; and
    wherein treating results in one or more of a reduction in the size of the ovarian cancer tumor, a reduction in the invasiveness of the ovarian cancer tumor, reduction in the growth rate of the ovarian cancer tumor, or prolonging survival of the subject.

2. The method of claim 1, wherein the monoclonal antibody or antibody fragment is administered systemically.

3. The method of claim 1, further comprising administering at least a second anticancer therapy to the subject.

4. The method of claim 1, wherein the antibody is administered intravenously, intradermally, intramuscularly, intraperitoneally, or subcutaneously.

5. The method of claim 1, wherein the antibody is administered intratumorally.

* * * * *

SEQUENCE LISTING

```
<160> NUMBER OF SEQ ID NOS: 180

<210> SEQ ID NO 1
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 1
ggactcgacc tcagtagcta ctactac                                            27

<210> SEQ ID NO 2
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 2
atttatgctg gtagtagtgg tagcact                                            27

<210> SEQ ID NO 3
<211> LENGTH: 42
<212> TYPE: DNA
<213> ORGANISM: Artificial sequence
<220> FEATURE:
<223> OTHER INFORMATION: Synthetic CDR sequence

<400> SEQUENCE: 3
gcgagaggtg gtggtagtac ttatgctcaa tattttaact tg                           42

<210> SEQ ID NO 4
<211> LENGTH: 9
<212> TYPE: PRT
<213> ORGANISM: Artificial sequence
<220> FEATURE:
```

```
<223> OTHER INFORMATION: Synthetic CDR sequence

<400> SEQUENCE: 4

Gly Leu Asp Leu Ser Ser Tyr Tyr Tyr
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 5

Ile Tyr Ala Gly Ser Ser Gly Ser Thr
1               5

<210> SEQ ID NO 6
<211> LENGTH: 14
<212> TYPE: PRT
<213> ORGANISM: Artificial sequence
<220> FEATURE:
<223> OTHER INFORMATION: Synthetic CDR sequence

<400> SEQUENCE: 6

Ala Arg Gly Gly Gly Ser Thr Tyr Ala Gln Tyr Phe Asn Leu
1               5                   10

<210> SEQ ID NO 7
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 7
ggattctcct tcagtagtat ttattgg                                         27

<210> SEQ ID NO 8
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 8
attcagatta ctagtggtat cact                                            24

<210> SEQ ID NO 9
<211> LENGTH: 45
<212> TYPE: DNA
<213> ORGANISM: Artificial sequence
<220> FEATURE:
<223> OTHER INFORMATION: Synthetic CDR sequence

<400> SEQUENCE: 9
agaaggggat atggtgccta tgctggtact ggtgcctctg acttg                     45

<210> SEQ ID NO 10
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 10
```

```
Gly Phe Ser Phe Ser Ser Ile Tyr Trp
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 11

Ile Gln Ile Thr Ser Gly Ile Thr
1               5

<210> SEQ ID NO 12
<211> LENGTH: 15
<212> TYPE: PRT
<213> ORGANISM: Artificial sequence
<220> FEATURE:
<223> OTHER INFORMATION: Synthetic CDR sequence

<400> SEQUENCE: 12

Arg Arg Gly Tyr Gly Ala Tyr Ala Gly Thr Gly Ala Ser Asp Leu
1               5                   10                  15

<210> SEQ ID NO 13
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 13
ggattcaccc tcaatagtta ttat                                         24

<210> SEQ ID NO 14
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 14
attgatagtg atagtcctac tacg                                         24

<210> SEQ ID NO 15
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 15
gcgagaggct atggtcctgt tcgattggat ctc                               33

<210> SEQ ID NO 16
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 16

Gly Phe Thr Leu Asn Ser Tyr Tyr
1               5
```

```
<210> SEQ ID NO 17
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 17

Ile Asp Ser Asp Ser Pro Thr Thr
1               5

<210> SEQ ID NO 18
<211> LENGTH: 11
<212> TYPE: PRT
<213> ORGANISM: Artificial sequence
<220> FEATURE:
<223> OTHER INFORMATION: Synthetic CDR sequence

<400> SEQUENCE: 18

Ala Arg Gly Tyr Gly Pro Val Arg Leu Asp Leu
1               5                   10

<210> SEQ ID NO 19
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 19
ggattctcct tcagtagcgg ctactgg                                      27

<210> SEQ ID NO 20
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 20
atttatgctg gtagtagtgg tgggcac                                      27

<210> SEQ ID NO 21
<211> LENGTH: 45
<212> TYPE: DNA
<213> ORGANISM: Artificial sequence
<220> FEATURE:
<223> OTHER INFORMATION: Synthetic CDR sequence

<400> SEQUENCE: 21
tgtacaagag ataattatgg tggtggtggt tctgcttcca aattg                  45

<210> SEQ ID NO 22
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 22

Gly Phe Ser Phe Ser Ser Gly Tyr Trp
1               5

<210> SEQ ID NO 23
<211> LENGTH: 9
<212> TYPE: PRT
<213> ORGANISM: Artificial sequence
```

```
<220> FEATURE:
<223> OTHER INFORMATION: Synthetic CDR sequence

<400> SEQUENCE: 23

Ile Tyr Ala Gly Ser Ser Gly Gly His
1               5

<210> SEQ ID NO 24
<211> LENGTH: 15
<212> TYPE: PRT
<213> ORGANISM: Artificial sequence
<220> FEATURE:
<223> OTHER INFORMATION: Synthetic CDR sequence

<400> SEQUENCE: 24

Cys Thr Arg Asp Asn Tyr Gly Gly Gly Ser Ala Ser Lys Leu
1               5                   10                  15

<210> SEQ ID NO 25
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 25
ggattctcct tcagtagtta tgga                                          24

<210> SEQ ID NO 26
<211> LENGTH: 21
<212> TYPE: DNA
<213> ORGANISM: Artificial sequence
<220> FEATURE:
<223> OTHER INFORMATION: Synthetic CDR sequence

<400> SEQUENCE: 26
attggtctta gtagtgagat c                                             21

<210> SEQ ID NO 27
<211> LENGTH: 30
<212> TYPE: DNA
<213> ORGANISM: Artificial sequence
<220> FEATURE:
<223> OTHER INFORMATION: Synthetic CDR sequence

<400> SEQUENCE: 27
gtgagagatc tttatcatag taatggtttg                                    30

<210> SEQ ID NO 28
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 28

Gly Phe Ser Phe Ser Ser Tyr Gly
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic CDR sequence

<400> SEQUENCE: 29
```

```
Ile Gly Leu Ser Ser Glu Ile
1               5
```

<210> SEQ ID NO 30
<211> LENGTH: 10
<212> TYPE: PRT
<213> ORGANISM: Artificial sequence
<220> FEATURE:
<223> OTHER INFORMATION: Synthetic CDR sequence

<400> SEQUENCE: 30

```
Val Arg Asp Leu Tyr His Ser Asn Gly Leu
1               5                   10
```

<210> SEQ ID NO 31
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 31
ggattctcct tcaatagcgg ctactgg                                        27

<210> SEQ ID NO 32
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 32
atctatacta gtagtcctac tggtgcc                                        27

<210> SEQ ID NO 33
<211> LENGTH: 45
<212> TYPE: DNA
<213> ORGANISM: Artificial sequence
<220> FEATURE:
<223> OTHER INFORMATION: Synthetic CDR sequence

<400> SEQUENCE: 33
tgtacaagag ataattttgg tggtggtggt tctgcttcca aattg                    45

<210> SEQ ID NO 34
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 34

```
Gly Phe Ser Phe Asn Ser Gly Tyr Trp
1               5
```

<210> SEQ ID NO 35
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 35

```
Ile Tyr Thr Ser Ser Pro Thr Gly Ala
1               5
```

```
<210> SEQ ID NO 36
<211> LENGTH: 15
<212> TYPE: PRT
<213> ORGANISM: Artificial sequence
<220> FEATURE:
<223> OTHER INFORMATION: Synthetic CDR sequence

<400> SEQUENCE: 36

Cys Thr Arg Asp Asn Phe Gly Gly Gly Gly Ser Ala Ser Lys Leu
1               5                   10                  15

<210> SEQ ID NO 37
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 37
ggattcaccc tcagtagcta ctac                                            24

<210> SEQ ID NO 38
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 38
attgatactg ataatgatat tagg                                            24

<210> SEQ ID NO 39
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 39
gggagaggct atggtgcgct tcggttggat ctc                                  33

<210> SEQ ID NO 40
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 40

Gly Phe Thr Leu Ser Ser Tyr Tyr
1               5

<210> SEQ ID NO 41
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 41

Ile Asp Thr Asp Asn Asp Ile Arg
1               5

<210> SEQ ID NO 42
<211> LENGTH: 11
<212> TYPE: PRT
```

-continued

<213> ORGANISM: Artificial sequence
<220> FEATURE:
<223> OTHER INFORMATION: Synthetic CDR sequence

<400> SEQUENCE: 42

Gly Arg Gly Tyr Gly Ala Leu Arg Leu Asp Leu
1               5                   10

<210> SEQ ID NO 43
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 43
ggattctccc tcagtagcta ccac                                          24

<210> SEQ ID NO 44
<211> LENGTH: 21
<212> TYPE: DNA
<213> ORGANISM: Artificial sequence
<220> FEATURE:
<223> OTHER INFORMATION: Synthetic CDR sequence

<400> SEQUENCE: 44
attaataatt atggtgccac a                                             21

<210> SEQ ID NO 45
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 45
gccagaagtc ctgggattcc tggttataat tcg                                33

<210> SEQ ID NO 46
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 46

Gly Phe Ser Leu Ser Ser Tyr His
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic CDR sequence

<400> SEQUENCE: 47

Ile Asn Asn Tyr Gly Ala Thr
1               5

<210> SEQ ID NO 48
<211> LENGTH: 11
<212> TYPE: PRT
<213> ORGANISM: Artificial sequence
<220> FEATURE:
<223> OTHER INFORMATION: Synthetic CDR sequence

```
<400> SEQUENCE: 48

Ala Arg Ser Pro Gly Ile Pro Gly Tyr Asn Ser
1               5                   10

<210> SEQ ID NO 49
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 49
ggattctcct tcagtagcaa ttca                                          24

<210> SEQ ID NO 50
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 50
attgctagta gtagtagtca tagt                                          24

<210> SEQ ID NO 51
<211> LENGTH: 51
<212> TYPE: DNA
<213> ORGANISM: Artificial sequence
<220> FEATURE:
<223> OTHER INFORMATION: Synthetic CDR sequence

<400> SEQUENCE: 51
gcgagagatt ctggtaatcg tggttacctt tatgcgggcg actttaactt g            51

<210> SEQ ID NO 52
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 52

Gly Phe Ser Phe Ser Ser Asn Ser
1               5

<210> SEQ ID NO 53
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 53

Ile Ala Ser Ser Ser Ser His Ser
1               5

<210> SEQ ID NO 54
<211> LENGTH: 17
<212> TYPE: PRT
<213> ORGANISM: Artificial sequence
<220> FEATURE:
<223> OTHER INFORMATION: Synthetic CDR sequence

<400> SEQUENCE: 54

Ala Arg Asp Ser Gly Asn Arg Gly Tyr Leu Tyr Ala Gly Asp Phe Asn
1               5                   10                  15
```

Leu

<210> SEQ ID NO 55
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 55
ggattcgacc tcagtagctc ctactac                                          27

<210> SEQ ID NO 56
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 56
attgacggtg gtgggggtga gcccact                                          27

<210> SEQ ID NO 57
<211> LENGTH: 39
<212> TYPE: DNA
<213> ORGANISM: Artificial sequence
<220> FEATURE:
<223> OTHER INFORMATION: Synthetic CDR sequence

<400> SEQUENCE: 57
gcgagacgag atgctggtgc tgggaacgcc tttagcttg                             39

<210> SEQ ID NO 58
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 58

Gly Phe Asp Leu Ser Ser Ser Tyr Tyr
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 59

Ile Asp Gly Gly Gly Gly Glu Pro Thr
1               5

<210> SEQ ID NO 60
<211> LENGTH: 13
<212> TYPE: PRT
<213> ORGANISM: Artificial sequence
<220> FEATURE:
<223> OTHER INFORMATION: Synthetic CDR sequence

<400> SEQUENCE: 60

Ala Arg Arg Asp Ala Gly Ala Gly Asn Ala Phe Ser Leu
1               5                   10

<210> SEQ ID NO 61
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 61
ggattcgact tcagtagcag ctacttt                                27

<210> SEQ ID NO 62
<211> LENGTH: 27
<212> TYPE: DNA
<213> ORGANISM: Artificial sequence
<220> FEATURE:
<223> OTHER INFORMATION: Synthetic CDR sequence

<400> SEQUENCE: 62
atttatactg ttattagtcg taagact                                27

<210> SEQ ID NO 63
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 63
gcgagatcgg caacaattga aagattggat ctc                         33

<210> SEQ ID NO 64
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 64

Gly Phe Asp Phe Ser Ser Ser Tyr Phe
1               5

<210> SEQ ID NO 65
<211> LENGTH: 9
<212> TYPE: PRT
<213> ORGANISM: Artificial sequence
<220> FEATURE:
<223> OTHER INFORMATION: Synthetic CDR sequence

<400> SEQUENCE: 65

Ile Tyr Thr Val Ile Ser Arg Lys Thr
1               5

<210> SEQ ID NO 66
<211> LENGTH: 11
<212> TYPE: PRT
<213> ORGANISM: Artificial sequence
<220> FEATURE:
<223> OTHER INFORMATION: Synthetic CDR sequence

<400> SEQUENCE: 66

Ala Arg Ser Ala Thr Ile Glu Arg Leu Asp Leu
1               5                   10

<210> SEQ ID NO 67
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 67
ggattcacca tcaataacta caac        24

<210> SEQ ID NO 68
<211> LENGTH: 21
<212> TYPE: DNA
<213> ORGANISM: Artificial sequence
<220> FEATURE:
<223> OTHER INFORMATION: Synthetic CDR sequence

<400> SEQUENCE: 68
atttggaatg gtgatggcag c        21

<210> SEQ ID NO 69
<211> LENGTH: 18
<212> TYPE: DNA
<213> ORGANISM: Artificial sequence
<220> FEATURE:
<223> OTHER INFORMATION: Synthetic CDR sequence

<400> SEQUENCE: 69
gcgagaaatt ttaacttg        18

<210> SEQ ID NO 70
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 70

Gly Phe Thr Ile Asn Asn Tyr Asn
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic CDR sequence

<400> SEQUENCE: 71

Ile Trp Asn Gly Asp Gly Ser
1               5

<210> SEQ ID NO 72
<211> LENGTH: 6
<212> TYPE: PRT
<213> ORGANISM: Artificial sequence
<220> FEATURE:
<223> OTHER INFORMATION: Synthetic CDR sequence

<400> SEQUENCE: 72

Ala Arg Asn Phe Asn Leu
1               5

<210> SEQ ID NO 73
<211> LENGTH: 21
<212> TYPE: DNA
<213> ORGANISM: Artificial sequence
<220> FEATURE:
<223> OTHER INFORMATION: Synthetic CDR sequence

<400> SEQUENCE: 73
ccgagtgttt ataggcacta c                                           21

<210> SEQ ID NO 74
<211> LENGTH: 9
<212> TYPE: DNA
<213> ORGANISM: Artificial sequence
<220> FEATURE:
<223> OTHER INFORMATION: Synthetic CDR sequence

<400> SEQUENCE: 74 tgggcttcc                                                          9

<210> SEQ ID NO 75
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 75
gcaggcgaat atgctagtga tagtgataat cat                              33

<210> SEQ ID NO 76
<211> LENGTH: 7
<212> TYPE: PRT
<213> ORGANISM: Artificial sequence
<220> FEATURE:
<223> OTHER INFORMATION: Synthetic CDR sequence

<400> SEQUENCE: 76

Pro Ser Val Tyr Arg His Tyr
1               5

<210> SEQ ID NO 77
<211> LENGTH: 3
<212> TYPE: PRT
<213> ORGANISM: Artificial sequence
<220> FEATURE:
<223> OTHER INFORMATION: Synthetic CDR sequence

<400> SEQUENCE: 77

Trp Ala Ser
1

<210> SEQ ID NO 78
<211> LENGTH: 11
<212> TYPE: PRT
<213> ORGANISM: Artificial sequence
<220> FEATURE:
<223> OTHER INFORMATION: Synthetic CDR sequence

<400> SEQUENCE: 78

Ala Gly Glu Tyr Ala Ser Asp Ser Asp Asn His
1               5                   10

<210> SEQ ID NO 79
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 79
cagagtgttt ataataacaa caac                                        24

<210> SEQ ID NO 80
<211> LENGTH: 9
<212> TYPE: DNA
<213> ORGANISM: Artificial sequence
<220> FEATURE:
<223> OTHER INFORMATION: Synthetic CDR sequence

<400> SEQUENCE: 80 gaagcatcc                                                                  9

<210> SEQ ID NO 81
<211> LENGTH: 30
<212> TYPE: DNA
<213> ORGANISM: Artificial sequence
<220> FEATURE:
<223> OTHER INFORMATION: Synthetic CDR sequence

<400> SEQUENCE: 81
gcaggcggtt atgctggcta catttgggct                                          30

<210> SEQ ID NO 82
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 82

Gln Ser Val Tyr Asn Asn Asn Asn
1               5

<210> SEQ ID NO 83
<211> LENGTH: 3
<212> TYPE: PRT
<213> ORGANISM: Artificial sequence
<220> FEATURE:
<223> OTHER INFORMATION: Synthetic CDR sequence

<400> SEQUENCE: 83

Glu Ala Ser
1

<210> SEQ ID NO 84
<211> LENGTH: 10
<212> TYPE: PRT
<213> ORGANISM: Artificial sequence
<220> FEATURE:
<223> OTHER INFORMATION: Synthetic CDR sequence

<400> SEQUENCE: 84

Ala Gly Gly Tyr Ala Gly Tyr Ile Trp Ala
1               5                   10

<210> SEQ ID NO 85
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 85
aagaacgcct atttatccta ctac                                                24

<210> SEQ ID NO 86
<211> LENGTH: 9
<212> TYPE: DNA
<213> ORGANISM: Artificial sequence

```
<220> FEATURE:
<223> OTHER INFORMATION: Synthetic CDR sequence

<400> SEQUENCE: 86 tgggcttcc                                                                    9

<210> SEQ ID NO 87
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 87
gcagccgaat atagtaatga tagtgataat ggt                                         33

<210> SEQ ID NO 88
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 88

Lys Asn Ala Tyr Leu Ser Tyr Tyr
1               5

<210> SEQ ID NO 89
<211> LENGTH: 11
<212> TYPE: PRT
<213> ORGANISM: Artificial sequence
<220> FEATURE:
<223> OTHER INFORMATION: Synthetic CDR sequence

<400> SEQUENCE: 89

Ala Ala Glu Tyr Ser Asn Asp Ser Asp Asn Gly
1               5                   10

<210> SEQ ID NO 90
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 90
cagagtgttt atagtaacaa ccgc                                                   24

<210> SEQ ID NO 91
<211> LENGTH: 9
<212> TYPE: DNA
<213> ORGANISM: Artificial sequence
<220> FEATURE:
<223> OTHER INFORMATION: Synthetic CDR sequence

<400> SEQUENCE: 91 tatgcagcc                                                                    9

<210> SEQ ID NO 92
<211> LENGTH: 36
<212> TYPE: DNA
<213> ORGANISM: Artificial sequence
<220> FEATURE:
<223> OTHER INFORMATION: Synthetic CDR sequence

<400> SEQUENCE: 92
```
gcaggatata aaactgctga ttctgatggt attgct        36

<210> SEQ ID NO 93
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 93

Gln Ser Val Tyr Ser Asn Asn Arg
1               5

<210> SEQ ID NO 94
<211> LENGTH: 3
<212> TYPE: PRT
<213> ORGANISM: Artificial sequence
<220> FEATURE:
<223> OTHER INFORMATION: Synthetic CDR sequence

<400> SEQUENCE: 94

Tyr Ala Ala
1

<210> SEQ ID NO 95
<211> LENGTH: 12
<212> TYPE: PRT
<213> ORGANISM: Artificial sequence
<220> FEATURE:
<223> OTHER INFORMATION: Synthetic CDR sequence

<400> SEQUENCE: 95

Ala Gly Tyr Lys Thr Ala Asp Ser Asp Gly Ile Ala
1               5                   10

<210> SEQ ID NO 96
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 96
gagagcgttt ataataataa ccgc        24

<210> SEQ ID NO 97
<211> LENGTH: 9
<212> TYPE: DNA
<213> ORGANISM: Artificial sequence
<220> FEATURE:
<223> OTHER INFORMATION: Synthetic CDR sequence

<400> SEQUENCE: 97 tatgcatcc        9

<210> SEQ ID NO 98
<211> LENGTH: 36
<212> TYPE: DNA
<213> ORGANISM: Artificial sequence
<220> FEATURE:
<223> OTHER INFORMATION: Synthetic CDR sequence

<400> SEQUENCE: 98
gtagccttta aaggttatgg tactgacggc aatgct        36

<210> SEQ ID NO 99

```
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 99

Glu Ser Val Tyr Asn Asn Asn Arg
1               5

<210> SEQ ID NO 100
<211> LENGTH: 3
<212> TYPE: PRT
<213> ORGANISM: Artificial sequence
<220> FEATURE:
<223> OTHER INFORMATION: Synthetic CDR sequence

<400> SEQUENCE: 100

Tyr Ala Ser
1

<210> SEQ ID NO 101
<211> LENGTH: 12
<212> TYPE: PRT
<213> ORGANISM: Artificial sequence
<220> FEATURE:
<223> OTHER INFORMATION: Synthetic CDR sequence

<400> SEQUENCE: 101

Val Ala Phe Lys Gly Tyr Gly Thr Asp Gly Asn Ala
1               5                   10

<210> SEQ ID NO 102
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 102
gagagtgttt atagtaacaa ccgc                                              24

<210> SEQ ID NO 103
<211> LENGTH: 36
<212> TYPE: DNA
<213> ORGANISM: Artificial sequence
<220> FEATURE:
<223> OTHER INFORMATION: Synthetic CDR sequence

<400> SEQUENCE: 103
gcaggatata agactgccga ttctgatggt cttggt                                 36

<210> SEQ ID NO 104
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 104

Glu Ser Val Tyr Ser Asn Asn Arg
1               5

<210> SEQ ID NO 105
<211> LENGTH: 12
<212> TYPE: PRT
<213> ORGANISM: Artificial sequence
```

```
<220> FEATURE:
<223> OTHER INFORMATION: Synthetic CDR sequence

<400> SEQUENCE: 105

Ala Gly Tyr Lys Thr Ala Asp Ser Asp Gly Leu Gly
1               5                   10

<210> SEQ ID NO 106
<211> LENGTH: 21
<212> TYPE: DNA
<213> ORGANISM: Artificial sequence
<220> FEATURE:
<223> OTHER INFORMATION: Synthetic CDR sequence

<400> SEQUENCE: 106
ccgagtgttt ataggcacta c                                                 21

<210> SEQ ID NO 107
<211> LENGTH: 33
<212> TYPE: DNA
<213> ORGANISM: Artificial sequence
<220> FEATURE:
<223> OTHER INFORMATION: Synthetic CDR sequence

<400> SEQUENCE: 107
gcaggcgaat atgctagtga tagtgataat cat                                    33

<210> SEQ ID NO 108
<211> LENGTH: 7
<212> TYPE: PRT
<213> ORGANISM: Artificial sequence
<220> FEATURE:
<223> OTHER INFORMATION: Synthetic CDR sequence

<400> SEQUENCE: 108

Pro Ser Val Tyr Arg His Tyr
1               5

<210> SEQ ID NO 109
<211> LENGTH: 11
<212> TYPE: PRT
<213> ORGANISM: Artificial sequence
<220> FEATURE:
<223> OTHER INFORMATION: Synthetic CDR sequence

<400> SEQUENCE: 109

Ala Gly Glu Tyr Ala Ser Asp Ser Asp Asn His
1               5                   10

<210> SEQ ID NO 110
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 110
cagaatgttt atagttacaa ccgc                                              24

<210> SEQ ID NO 111
<211> LENGTH: 9
<212> TYPE: DNA
<213> ORGANISM: Artificial sequence
<220> FEATURE:
<223> OTHER INFORMATION: Synthetic CDR sequence

<400> SEQUENCE: 111
```

```
gaagcatcc                                                              9

<210> SEQ ID NO 112
<211> LENGTH: 39
<212> TYPE: DNA
<213> ORGANISM: Artificial sequence
<220> FEATURE:
<223> OTHER INFORMATION: Synthetic CDR sequence

<400> SEQUENCE: 112
gcaggcggtt atgattgtag gagttctgat tgtgatgct                             39

<210> SEQ ID NO 113
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 113

Gln Asn Val Tyr Ser Tyr Asn Arg
1               5

<210> SEQ ID NO 114
<211> LENGTH: 13
<212> TYPE: PRT
<213> ORGANISM: Artificial sequence
<220> FEATURE:
<223> OTHER INFORMATION: Synthetic CDR sequence

<400> SEQUENCE: 114

Ala Gly Gly Tyr Asp Cys Arg Ser Ser Asp Cys Asp Ala
1               5                   10

<210> SEQ ID NO 115
<211> LENGTH: 18
<212> TYPE: DNA
<213> ORGANISM: Artificial sequence
<220> FEATURE:
<223> OTHER INFORMATION: Synthetic CDR sequence

<400> SEQUENCE: 115
cagagcatta atagttgg                                                    18

<210> SEQ ID NO 116
<211> LENGTH: 39
<212> TYPE: DNA
<213> ORGANISM: Artificial sequence
<220> FEATURE:
<223> OTHER INFORMATION: Synthetic CDR sequence

<400> SEQUENCE: 116
caacagggtt atagttatag taatgttgat aataatatt                             39

<210> SEQ ID NO 117
<211> LENGTH: 6
<212> TYPE: PRT
<213> ORGANISM: Artificial sequence
<220> FEATURE:
<223> OTHER INFORMATION: Synthetic CDR sequence

<400> SEQUENCE: 117

Gln Ser Ile Asn Ser Trp
1               5
```

```
<210> SEQ ID NO 118
<211> LENGTH: 13
<212> TYPE: PRT
<213> ORGANISM: Artificial sequence
<220> FEATURE:
<223> OTHER INFORMATION: Synthetic CDR sequence

<400> SEQUENCE: 118

Gln Gln Gly Tyr Ser Tyr Ser Asn Val Asp Asn Asn Ile
1               5                   10

<210> SEQ ID NO 119
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 119
caaagtgttt atcttcagaa caac                                         24

<210> SEQ ID NO 120
<211> LENGTH: 30
<212> TYPE: DNA
<213> ORGANISM: Artificial sequence
<220> FEATURE:
<223> OTHER INFORMATION: Synthetic CDR sequence

<400> SEQUENCE: 120
cagggcggtt acagtggata tatcaattct                                   30

<210> SEQ ID NO 121
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 121

Gln Ser Val Tyr Leu Gln Asn Asn
1               5

<210> SEQ ID NO 122
<211> LENGTH: 10
<212> TYPE: PRT
<213> ORGANISM: Artificial sequence
<220> FEATURE:
<223> OTHER INFORMATION: Synthetic CDR sequence

<400> SEQUENCE: 122

Gln Gly Gly Tyr Ser Gly Tyr Ile Asn Ser
1               5                   10

<210> SEQ ID NO 123
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 123
gagagtgttt ataataacta ccgc                                         24

<210> SEQ ID NO 124
<211> LENGTH: 9
<212> TYPE: DNA
<213> ORGANISM: Artificial sequence
```

```
<220> FEATURE:
<223> OTHER INFORMATION: Synthetic CDR sequence

<400> SEQUENCE: 124 gctgcatcc                                                                    9

<210> SEQ ID NO 125
<211> LENGTH: 36
<212> TYPE: DNA
<213> ORGANISM: Artificial sequence
<220> FEATURE:
<223> OTHER INFORMATION: Synthetic CDR sequence

<400> SEQUENCE: 125
gtaggatata aaagtggtta tattgatagt attcct                                     36

<210> SEQ ID NO 126
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 126

Glu Ser Val Tyr Asn Asn Tyr Arg
1               5

<210> SEQ ID NO 127
<211> LENGTH: 3
<212> TYPE: PRT
<213> ORGANISM: Artificial sequence
<220> FEATURE:
<223> OTHER INFORMATION: Synthetic CDR sequence

<400> SEQUENCE: 127

Ala Ala Ser
1

<210> SEQ ID NO 128
<211> LENGTH: 12
<212> TYPE: PRT
<213> ORGANISM: Artificial sequence
<220> FEATURE:
<223> OTHER INFORMATION: Synthetic CDR sequence

<400> SEQUENCE: 128

Val Gly Tyr Lys Ser Gly Tyr Ile Asp Ser Ile Pro
1               5                   10

<210> SEQ ID NO 129
<211> LENGTH: 24
<212> TYPE: DNA
<213> ORGANISM: Artificial sequence
<220> FEATURE:
<223> OTHER INFORMATION: Synthetic CDR sequence

<400> SEQUENCE: 129
gcgagtgttt atagtaacaa ctac                                                  24

<210> SEQ ID NO 130
<211> LENGTH: 36
<212> TYPE: DNA
<213> ORGANISM: Artificial sequence
<220> FEATURE:
<223> OTHER INFORMATION: Synthetic CDR sequence

<400> SEQUENCE: 130
```
gcaggcgatt atagtagtag tagtgatatg tgtatt                                    36

<210> SEQ ID NO 131
<211> LENGTH: 8
<212> TYPE: PRT
<213> ORGANISM: Artificial sequence
<220> FEATURE:
<223> OTHER INFORMATION: Synthetic CDR sequence

<400> SEQUENCE: 131

Ala Ser Val Tyr Ser Asn Asn Tyr
1               5

<210> SEQ ID NO 132
<211> LENGTH: 12
<212> TYPE: PRT
<213> ORGANISM: Artificial sequence
<220> FEATURE:
<223> OTHER INFORMATION: Synthetic CDR sequence

<400> SEQUENCE: 132

Ala Gly Asp Tyr Ser Ser Ser Asp Met Cys Ile
1               5                   10

<210> SEQ ID NO 133
<211> LENGTH: 364
<212> TYPE: DNA
<213> ORGANISM: Artificial sequence
<220> FEATURE:
<223> OTHER INFORMATION: Synthetic oligonucleotide

<400> SEQUENCE: 133
cagtcgctgg aggagtccga gggaggcctg gtccagcctg aggatccct gacactcacc            60 tgcaaagcct ctggactcga cctcagtagc tactactaca tgtgctgggt ccgccaggct           120
ccagggaagg ggctggagtg gatcgcatgc atttatgctg gtagtagtgg tagcacttac           180
tacgcgagct gggcgaaagg ccgattcacc atctccaaaa cctcgtcgac cacggtgact           240
ctgcaaatga ccagtctgac agccgcggac acggccacct atttctgtgc gagaggtggt          300
ggtagtactt atgctcaata ttttaacttg tggggcccag gcaccctggt caccatctcc          360
tcag                                                                       364

<210> SEQ ID NO 134
<211> LENGTH: 331
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (18)..(18)
<223> OTHER INFORMATION: n is a, c, g, or t

<400> SEQUENCE: 134
gagctcgata tgacccanac accagcctcc gtgtctgcag ctgtgggagg cacagtcagc           60
atcaattgcc agtccagtcc gagtgtttat aggcactact tatcctggta tcagcagaaa         120
ccagggcagc ctcccaagct cctgatctac tgggcttcca ctctggcatc tggggtccca         180
tcgcggttca gcggcagtgg atctgggaca gagttcactc tcaccatcag cggcgtgcag         240
tgtgacgatg ctgccactta ctactgtgca ggcgaatatg ctagtgatag tgataatcat         300
ttcggcggag ggaccgagct ggagatccta g                                        331

```
<210> SEQ ID NO 135
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 135
gagcagtcgg tgaaggagtc cggggaggc ctggtccagc ctgagggatc cctgacactc     60
acctgcacag cttctggatt ctccttcagt agtatttatt ggatatgctg ggtccgccag    120
gctccaggga aggggctgga gttgatcgca tgcattcaga ttactagtgg tatcacttac    180
tacgcgagct gggcgaaagg ccgattcacc atctccaaaa tgtcgtcgac cacggtgact    240
ctgcaaatga ccagtctgac agtcgcggac acgccacct atttctgtgg gagaagggga    300
tatggtgcct atgctggtac tggtgcctct gacttgtggg gcccaggcac cctggtcacc    360
gtctcttcag                                                          370

<210> SEQ ID NO 136
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 136
gagctcgatc tgacccagac tgcatcgtcc gtgtctgcag ctgtgggagg caccgtcacc     60
atcaattgcc agtccagtca gagtgtttat aataacaaca acttagcctg gtatcagcag    120
aaaccagggc agcctcccaa gctcctgatc tacgaagcat ccaaactggc atctggggtc    180
ccatcgcggt tcaaaggcag tggatctggg acacagttca ctctcaccat cagcggcgtg    240
cagtgtgacg atgctgccac ttactattgt gcaggcggtt atgctggcta catttgggct    300
ttcggcggag ggaccgaggt ggtggtcaaa g                                   331

<210> SEQ ID NO 137
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 137
gagcagtcgg tggaggagtc cggggaggc ctgttccagc ctgggggatc cctggcactc     60
acctgcaaag cctctggatt caccctcaat agttattata tgtcctgggt ccgccaggct    120
ccagggaagg ggctggagtg gatcggatgc attgatagtg atagtcctac tacgactgcc    180
tacgcgaact gggcgagagg ccgattcacc atctccaaga cctcgtcgac cacggtgact    240
ctgcaaatga ccagtctgac agccgcggac acgccacct atttctgtgc gagaggctat    300
ggtcctgttc gattggatct ctggggccag ggcaccctgg tcaccgtctc ttcag         355

<210> SEQ ID NO 138
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 138
acccagacac cagcctccgt gtctgcagct gtgggaggca cagtcagcat caattgccag     60
```

```
tccagtcaga gtgtttataa gaacgcctat ttatcctact acttagcctg gtatcagcag    120
aaaccagggc agcctcccaa gctcctgatc tactgggctt ccactctggc atctggggtc    180
ccatcgcggt tcaaaggcag tggatctggg acacagttca ctctcaccat cagcgacgtg    240
cagtgtgacg atgctgccac ttactactgt gcagccgaat atagtaatga tagtgataat    300
ggtttcggcg agggaccga ggtggaaatc aaag                                 334
```

<210> SEQ ID NO 139
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 139

```
gagcagtcgt tggaggagtc cggggagac ctggtcaagc ctgagggatc cctgacactc     60
acctgcgcag cctctggatt ctccttcagt agcggctact ggatatgctg ggtccgccag    120
gctccaggga aggggctgga gtggatcgga tgcatttatg ctggtagtag tggtgggcac    180
atttattacg cgacctggc gaaaggccga ttcaccatct cccaaacctc gtcgaccacg    240
gtgactctgc aaatgaccag tctgacagcc gcggacacgg ccacatattt ctgtacaaga    300
gataattatg gtggtggtgg ttctgcttcc aaattgtggg gccaggcac cctggtcacc     360 atctcttcag                                                            370
```

<210> SEQ ID NO 140
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 140

```
gagctcgtga tgacccagac tccatcccc gtgtctgcag ctgtgggagg cacagtcacc     60
atcaactgcc agtccagtca gagtgtttat agtaacaacc gcttagcctg gtatcagcag    120
aaaccagggc agcctcccaa gctcctggtc tattatgcag ccactctggc atctggggtc    180
ccgtcgcggt tcaaaggcag tggatatggg acacagtcca ctctcaccat cgccgatgtg    240
gtgtgtgacg atgctgccac ttactactgt gcaggatata aaactgctga ttctgatggt    300
attgctttcg gcggagggac cgaggtggaa atcaaag                              337
```

<210> SEQ ID NO 141
<211> LENGTH: 346
<212> TYPE: DNA
<213> ORGANISM: Artificial sequence
<220> FEATURE:
<223> OTHER INFORMATION: Synthetic oligonucleotide

<400> SEQUENCE: 141

```
cagtcggtga aggagtccga ggggaggcctg gtccagcctg agggatccct gacactcacc     60
tgcaaagcct ctggattctc cttcagtagt tatggagtga actgggtccg ccaggctcca    120
gggaaggggc tggagtggat cgcgtatatt ggtcttagta gtgagatcac ttactacgcg    180
ggctgggcga aaggccgatt caccatctcc aagccctcgt cgaccacggt gactctgcaa    240
atgaccagtc tgacagccgc ggacacggcc acctatttct gtgtgagaga tctttatcat    300
agtaatggtt tgtggggccc aggcaccctg gtcaccatct cttcag                    346
```

<210> SEQ ID NO 142
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 142

```
gagctcgatc tgacccagac tccatccccc gtgtctgcag ctgtgggagg cacagtcacc      60
gtcagttgcc aggccagtga gagcgtttat aataataacc gcttatcctg gtatcagcag     120
aaaccagggc agcctcccaa gctcctgatc tattatgcat ccactctggc atctggggtc     180
ccatcgcggt tcagcggcag tggatctggg acacagttca ctctcaccat cagcagcgtg     240
caatgtgctg atgctgccac gtattattgt gtagccttta aaggttatgg tactgacggc     300
aatgctttcg gcggagggac cgaggtggaa atcaaag                              337
```

<210> SEQ ID NO 143
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 143

```
gagcagtcgg tgaaggagtc cggggggagac ctggtcaagc ctgagggatc cctgacactc      60
acctgcacag cctctggatt ctccttcaat agcggctact gggtatgctg ggtccgccag     120
gctccaggga aggggctgga gtggatcgct tgcatctata ctagtagtcc tactggtgcc     180
atatactacg cgacctgggc gaaaggccga ttcaccatct cccaaacctc gtcgaccacg     240
gtgactctgc aaatgaccag tctgacagcc gcggacacgg ccacctattt ctgtacaaga     300 gataatttg tggtggtgg ttctgcttcc aaattgtggg gcccaggcac cctggtcacc     360
atctcttcag                                                             370
```

<210> SEQ ID NO 144
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 144

```
gagctcgtga tgacccagac tccatcttcc aagtctgtcc ctgtgggagg cacagtcacc      60
atcgattgcc aggccagtga gagtgtttat agtaacaacc gctgtgcctg gtatcagcag     120
aaaccagggc agcctcccaa gctcctgatc tattatgcat ccactctggc atctggggtc     180
ccgtcgcggt tcaaatgcag tggatctggg acacggttca ctctcaccat cagcggcgtg     240
cagtgtgaag atgctgccac ttactactgt gcaggatata agactgccga ttctgatggt     300
cttggtttcg gcggagggac cgaggtggaa atcaaa                                336
```

<210> SEQ ID NO 145
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 145

```
gagcagtcgg tgaaggagtc cgagggagac ctggtcaagc ctgagggatc cctgacactc      60
```

```
gcctgcacag cttctggatt caccctcagt agctactaca tgtgctgggt ccgccaggct    120
ccagggaagg ggctggaatg gatcgcatgc attgatactg ataatgatat taggactgcc    180
tacgcgagct gggcgagggg ccgattcacc atctccagga cctcgtcgac cacggtgact    240
ctgcaaatga ccagtctgac agccgcggac acggccacct atttctgtgg gagaggctat    300
ggtgcgcttc ggttggatct ctggggccag ggcccctggt caccgtctct tcag          354

<210> SEQ ID NO 146
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 146
gagctcgatc tgacccagac accagcctcc gtgtctgcag ctgtgggagg cacagtcagc     60
atcaattgcc agtccagtcc gagtgtttat aggcactact tatcctggta tcagcagaaa    120
ccagggcagc ctcccaagct cctgatctac tgggcttcca ctctggcatc tggggtccca    180
tcgcggttca gcggcagtgg atctgggaca gagttcactc tcaccatcag cggcgtgcag    240
tgtgacgatg ctgccactta ctactgtgca ggcgaatatg ctagtgatag tgataatcat    300
ttcggcggag ggaccgaggt ggaaatcaaa g                                   331

<210> SEQ ID NO 147
<211> LENGTH: 343
<212> TYPE: DNA
<213> ORGANISM: Artificial sequence
<220> FEATURE:
<223> OTHER INFORMATION: Synthetic oligonucleotide

<400> SEQUENCE: 147
cagtcggtga aggagtccga gggtcgcctg gtcacgcctg gacacccct gacactcacc      60 tgcacagtct ctggattctc cctcagtagc taccacatgg gctgggtccg ccaggctcca    120
gggaaggggc tggaatacat cggaatcatt aataattatg gtgccacata ctacgcgagc    180
tgggcaaaag gccgattcac catctccaga acctcgacca cggtggatct gaaaatgacc    240
agtctgacaa ccgaggacac ggccacctat ttctgtgcca gaagtcctgg gattcctggt    300
tataattcgt ggggcccagg caccctggtc accatctcct cag                      343

<210> SEQ ID NO 148
<211> LENGTH: 340
<212> TYPE: DNA
<213> ORGANISM: Artificial sequence
<220> FEATURE:
<223> OTHER INFORMATION: Synthetic oligonucleotide

<400> SEQUENCE: 148
gagctcgatc tgacccagac tccatcttcc acgtctgcgg ctgtgggagg cacagtcacc     60
atcaactgcc agtccagtca gaatgtttat agttacaacc gcttatcctg gtttcagcag    120
aaaccagggc agcctcccaa gctcctgatc tacgaagcat ccaaactggc atctggggtc    180
ccatcgcggt tcaaaggcag tggatctggg acacagttca ctctcaccat cagcggcgtg    240
cagtgtgacg atgctgccac ttactactgt gcaggcggtt atgattgtag gagttctgat    300
tgtgatgctt tcggcggagg gaccgaggtg gaaatcaaac                          340

<210> SEQ ID NO 149
```

```
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 149
agcagttcgg tggaggagtc cggggagac ctggtcaagc ccggggcatc cctgacactc      60
acctgcacag cctctggatt ctccttcagt agcaattcaa tgtgctgggt ccgccaggct    120
ccagggaagg gctggagtg atcggatgc attgctagta gtagtagtca tagtacttac     180
tacgcgagct gggcgaaagg ccgattcacc atctccaaaa cctcgtcgac cacggtgact    240
ctgcaaatga ccagtctgac agccgcggac atggccacct atttctgtgc gagagattct    300
ggtaatcgtg gttaccttta tgcgggcgac tttaacttgt ggggcccagg caccctggtc    360
accgtctctt cag                                                       373

<210> SEQ ID NO 150
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 150
gagctcgtgc tgacccagac tccagcctct gtggaggtag ctgtgggagg cacagtcacc     60
atcaattgcc aggccagtca gagcattaat agttggttat cctggtatca gcagaaacca    120
gggcagcgtc ccaaactcct gatctacgaa gcatccactc tggcatctgg ggtctcatcg    180
cggttcagtg gcagtggatc tgggacacag ttcactctca ccatcagcgg cgtgcagtgt    240
gacgatgctg ccacttacta ctgtcaacag ggttatagtt atagtaatgt tgataataat    300
attttcggcg gagggaccga ggtggtggtc aaag                                334

<210> SEQ ID NO 151
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 151
cagtcgttgg aggagtccgg gggaggcctg gtcaagcctg agggatccct gacactcacc     60
tgcacagcct ctggattcga cctcagtagc tcctactaca tgtgctgggt ccgccaggct    120
ccagggaagg gctggagtg atcgtctgt attgacggtg gtggggtga gcccactgcc     180 tacccgagct gggcgaaagg ccgattcacc gtctccaaaa cctcgtcgac cacggtgact    240
cttcaaatga ccagtctgac agtcgcggac acggccacgt atttctgtgc gagacgagat    300
gctggtgctg ggaacgcctt tagcttgtgg ggcccaggca ccctggtcac catctcctca    360
g                                                                    361

<210> SEQ ID NO 152
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 152
gagctcgata tgacccagac tccatccccc gtgtctgcag ctgtgggagg cacagtcacc     60
```

```
atcagttgcc agtccagtca aagtgtttat cttcagaaca acttagcctg gtatcagcag    120
aaaccagggc agcctcccaa gctcctgatc tattatgcat ccactctggc atctggggtc    180
tcatcgcggt tcaaaggcag tggatctggg acacagttca ctctcaccat cagcgacctg    240
gagtgtgacg atgctgccac ttactactgt cagggcggtt acagtggata tatcaattct    300
ttcggcggag ggaccgaggt ggaaatcaaa g                                   331
```

```
<210> SEQ ID NO 153
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 153
cagtcggtga aggagtccga gggagacctg gtcaagcctg ggcatccct gacactcacc     60 tgcaaagcct ctggattcga cttcagtagc agctacttta tgtgctgggt ccgccaggct    120
ccagggaggg gctggagtg atcgcatgc atttatactg ttattagtcg taagacttat      180
tacgcgagct gggcgaaagg ccgattcacc atctccaaaa cctcggcgac acggtggat     240 ctgcaaatga ccagtctgac agccgcggac acggccacct atttctgtgc gagatcggca    300
acaattgaaa gattggatct ctggggccag ggcaccctgg tcaccgtctc ctcag         355
```

```
<210> SEQ ID NO 154
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 154
gagctcgatc tgacccagac tccatcgccc gtgtctgcac ctgtgggagg cacagtcacc     60
atcaattgcc aggccagtga gagtgtttat aataactacc gcttatcctg gtatcagcag    120
aaaccagggc agcctcccaa gctcctaatc tatgctgcat ccactctggc atctggggtc    180
ccatcgcggt tcaaaggcag tggatctggg acacagttca ctctcgccat cagcgatgtg    240
gtgtgtgacg atgctgccac ttactactgt gtaggatata aaagtggtta tattgatagt    300
attcctttcg gcggagggac cgaggtggtg gtcaaag                             337
```

```
<210> SEQ ID NO 155
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 155
cagtcgttgg aggagtccgg gggagacctg gtcaagcctg ggcatccct gacactcacc      60 tgcacagctt ctggattcac catcaataac tacaacatta ctgggtccg ccaggctcca     120 gggaagggc tggagtggat cgcacgtatt tggaatggtg atggcagcac atactacgcg     180
agctgggcga aaggccgatt caccatctcc aaaacctcgt cgaccacggt gactctacaa    240
atgaccagtc tgacagccgc ggacacggcc acctatttct gtgcgagaaa ttttaacttg    300
tggggcccag gcaccctggt caccatctct tcag                                334
```

```
<210> SEQ ID NO 156
```

<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 156
gagctcgtgc tgacccagac tccatctccc gtgtctgcag ctgtgggagg cacagtcacc    60
atcaattgcc agtccagtgc gagtgtttat agtaacaact acttatcctg gtttcagcag   120
aaaccagggc agcctcccaa gcccctgatc tattatgcat ccactctggc atctggggtc   180
ccatcgcggt ttaaaggcag tggatctggg acacagttca ctctcaccat cagcgacgtg   240
cagtgtgacg atgctgccac ttactactgt gcaggcgatt atagtagtag tagtgatatg   300
tgtattttcg gcggagggac cgagctggaa atcaaag                             337

<210> SEQ ID NO 157
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 157

Gln Ser Leu Glu Glu Ser Gly Gly Leu Val Gln Pro Glu Gly Ser
1               5                   10                  15

Leu Thr Leu Thr Cys Lys Ala Ser Gly Leu Asp Leu Ser Tyr Tyr
                20                  25                  30

Tyr Met Cys Trp Val Arg Gln Ala Pro Gly Lys Gly Leu Glu Trp Ile
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Gly Gly Ser Thr Tyr Ala Gln Tyr Phe Asn Leu Trp Gly
            100                 105                 110

Pro Gly Thr Leu Val Thr Ile Ser Ser
        115                 120

<210> SEQ ID NO 158
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 158

Glu Leu Asp Met Thr Thr Pro Ala Ser Val Ser Ala Ala Val Gly Gly
1               5                   10                  15

Thr Val Ser Ile Asn Cys Gln Ser Ser Pro Ser Val Tyr Arg His Tyr
                20                  25                  30

Leu Ser Trp Tyr Gln Gln Lys Pro Gly Gln Pro Pro Lys Leu Leu Ile
            35                  40                  45

Tyr Trp Ala Ser Thr Leu Ala Ser Gly Val Pro Ser Arg Phe Ser Gly
        50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Ala Gly Glu Tyr Ser Asp Ser
                85                  90                  95

Asp Asn His Phe Gly Gly Gly Thr Glu Leu Glu Ile Leu
            100                 105

<210> SEQ ID NO 159
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 159

Glu Gln Ser Val Lys Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ile
                20                  25                  30

Tyr Trp Ile Cys Trp Val Arg Gln Ala Pro Gly Lys Gly Leu Glu Leu
            35                  40                  45

Ile Ala Cys Ile Gln Ile Thr Ser Gly Ile Thr Tyr Tyr Ala Ser Trp
50                  55                  60

Ala Lys Gly Arg Phe Thr Ile Ser Lys Met Ser Ser Thr Thr Val Thr
65                  70                  75                  80

Leu Gln Met Thr Ser Leu Thr Val Ala Asp Thr Ala Thr Tyr Phe Cys
                85                  90                  95

Gly Arg Arg Gly Tyr Gly Ala Tyr Ala Gly Thr Gly Ala Ser Asp Leu
            100                 105                 110

Trp Gly Pro Gly Thr Leu Val Thr Val Ser Ser
            115                 120

<210> SEQ ID NO 160
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 160

Glu Leu Asp Leu Thr Gln Thr Ala Ser Ser Val Ser Ala Ala Val Gly
1               5                   10                  15

Gly Thr Val Thr Ile Asn Cys Gln Ser Ser Gln Ser Val Tyr Asn Asn
                20                  25                  30

Asn Asn Leu Ala Trp Tyr Gln Gln Lys Pro Gly Gln Pro Pro Lys Leu
            35                  40                  45

Leu Ile Tyr Glu Ala Ser Lys Leu Ala Ser Gly Val Pro Ser Arg Phe
50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Gly Tyr Ala Gly
                85                  90                  95

Tyr Ile Trp Ala Phe Gly Gly Gly Thr Glu Val Val Val Lys
            100                 105                 110

<210> SEQ ID NO 161
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 161

Glu Gln Ser Val Glu Glu Ser Gly Gly Gly Leu Phe Gln Pro Gly Gly
1               5                   10                  15

Ser Leu Ala Leu Thr Cys Lys Ala Ser Gly Phe Thr Leu Asn Ser Tyr
            20                  25                  30

Tyr Met Ser Trp Val Arg Gln Ala Pro Gly Lys Gly Leu Glu Trp Ile
        35                  40                  45

Gly Cys Ile Asp Ser Asp Ser Pro Thr Thr Ala Tyr Ala Asn Trp
50                  55                  60

Ala Arg Gly Arg Phe Thr Ile Ser Lys Thr Ser Ser Thr Val Thr
65                  70                  75                  80

Leu Gln Met Thr Ser Leu Thr Ala Ala Asp Thr Ala Thr Tyr Phe Cys
                85                  90                  95

Ala Arg Gly Tyr Gly Pro Val Arg Leu Asp Leu Trp Gly Gln Gly Thr
            100                 105                 110

Leu Val Thr Val Ser Ser
        115

<210> SEQ ID NO 162
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 162

Thr Gln Thr Pro Ala Ser Val Ser Ala Ala Val Gly Gly Thr Val Ser
1               5                   10                  15

Ile Asn Cys Gln Ser Ser Gln Ser Val Tyr Lys Asn Ala Tyr Leu Ser
            20                  25                  30

Tyr Tyr Leu Ala Trp Tyr Gln Gln Lys Pro Gly Gln Pro Pro Lys Leu
        35                  40                  45

Leu Ile Tyr Trp Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Ala Glu Tyr Ser Asn
                85                  90                  95

Asp Ser Asp Asn Gly Phe Gly Gly Thr Glu Val Glu Ile Lys
            100                 105                 110

<210> SEQ ID NO 163
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 163

Glu Gln Ser Leu Glu Glu Ser Gly Gly Asp Leu Val Lys Pro Glu Gly
1               5                   10                  15

Ser Leu Thr Leu Thr Cys Ala Ala Ser Gly Phe Ser Phe Ser Ser Gly
            20                  25                  30

Tyr Trp Ile Cys Trp Val Arg Gln Ala Pro Gly Lys Gly Leu Glu Trp
        35                  40                  45

Ile Gly Cys Ile Tyr Ala Gly Ser Ser Gly Gly His Ile Tyr Tyr Ala
    50                  55                  60

```
Thr Trp Ala Lys Gly Arg Phe Thr Ile Ser Gln Ser Ser Thr Thr
 65                  70                  75                  80

Val Thr Leu Gln Met Thr Ser Leu Thr Ala Ala Asp Thr Ala Thr Tyr
                 85                  90                  95

Phe Cys Thr Arg Asp Asn Tyr Gly Gly Gly Ser Ala Ser Lys Leu
            100                 105                 110

Trp Gly Pro Gly Thr Leu Val Thr Ile Ser Ser
            115                 120
```

<210> SEQ ID NO 164
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 164

```
Glu Leu Val Met Thr Gln Thr Pro Ser Pro Val Ser Ala Ala Val Gly
  1               5                  10                  15

Gly Thr Val Thr Ile Asn Cys Gln Ser Ser Gln Ser Val Tyr Ser Asn
                 20                  25                  30

Asn Arg Leu Ala Trp Tyr Gln Gln Lys Pro Gly Gln Pro Pro Lys Leu
             35                  40                  45

Leu Val Tyr Tyr Ala Ala Thr Leu Ala Ser Gly Val Pro Ser Arg Phe
 50                  55                  60

Lys Gly Ser Gly Tyr Gly Thr Gln Ser Thr Leu Thr Ile Ala Asp Val
 65                  70                  75                  80

Val Cys Asp Asp Ala Ala Thr Tyr Tyr Cys Ala Gly Tyr Lys Thr Ala
                 85                  90                  95

Asp Ser Asp Gly Ile Ala Phe Gly Gly Gly Thr Glu Val Glu Ile Lys
            100                 105                 110
```

<210> SEQ ID NO 165
<211> LENGTH: 115
<212> TYPE: PRT
<213> ORGANISM: Artificial sequence
<220> FEATURE:
<223> OTHER INFORMATION: Synthetic polypeptide

<400> SEQUENCE: 165

```
Gln Ser Val Lys Glu Ser Glu Gly Gly Leu Val Gln Pro Glu Gly Ser
  1               5                  10                  15

Leu Thr Leu Thr Cys Lys Ala Ser Gly Phe Ser Phe Ser Ser Tyr Gly
                 20                  25                  30

Val Asn Trp Val Arg Gln Ala Pro Gly Lys Gly Leu Glu Trp Ile Ala
             35                  40                  45

Tyr Ile Gly Leu Ser Ser Glu Ile Thr Tyr Tyr Ala Gly Trp Ala Lys
 50                  55                  60

Gly Arg Phe Thr Ile Ser Lys Pro Ser Ser Thr Thr Val Thr Leu Gln
 65                  70                  75                  80

Met Thr Ser Leu Thr Ala Ala Asp Thr Ala Thr Tyr Phe Cys Val Arg
                 85                  90                  95

Asp Leu Tyr His Ser Asn Gly Leu Trp Gly Pro Gly Thr Leu Val Thr
            100                 105                 110

Ile Ser Ser
        115
```

<210> SEQ ID NO 166

<211> LENGTH: 112
<212> TYPE: PRT
<213> ORGANISM: Artificial sequence
<220> FEATURE:
<223> OTHER INFORMATION: Synthetic polypeptide

<400> SEQUENCE: 166

Glu Leu Asp Leu Thr Gln Thr Pro Ser Pro Val Ser Ala Ala Val Gly
1               5                   10                  15

Gly Thr Val Thr Val Ser Cys Gln Ala Ser Glu Ser Val Tyr Asn Asn
            20                  25                  30

Asn Arg Leu Ser Trp Tyr Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Gln Phe Thr Leu Thr Ile Ser Ser Val
65                  70                  75                  80

Gln Cys Ala Asp Ala Ala Thr Tyr Tyr Cys Val Ala Phe Lys Gly Tyr
                85                  90                  95

Gly Thr Asp Gly Asn Ala Phe Gly Gly Gly Thr Glu Val Glu Ile Lys
            100                 105                 110

<210> SEQ ID NO 167
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 167

Glu Gln Ser Val Lys Glu Ser Gly Gly Asp Leu Val Lys Pro Glu Gly
1               5                   10                  15

Ser Leu Thr Leu Thr Cys Thr Ala Ser Gly Phe Ser Phe Asn Ser Gly
            20                  25                  30

Tyr Trp Val Cys Trp Val Arg Gln Ala Pro Gly Lys Gly Leu Glu Trp
        35                  40                  45

Ile Ala Cys Ile Tyr Thr Ser Ser Pro Thr Gly Ala Ile Tyr Tyr Ala
    50                  55                  60

Thr Trp Ala Lys Gly Arg Phe Thr Ile Ser Gln Thr Ser Ser Thr Thr
65                  70                  75                  80

Val Thr Leu Gln Met Thr Ser Leu Thr Ala Ala Asp Thr Ala Thr Tyr
                85                  90                  95

Phe Cys Thr Arg Asp Asn Phe Gly Gly Gly Ser Ala Ser Lys Leu
            100                 105                 110

Trp Gly Pro Gly Thr Leu Val Thr Ile Ser Ser
        115                 120

<210> SEQ ID NO 168
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 168

Glu Leu Val Met Thr Gln Thr Pro Ser Ser Lys Ser Val Pro Val Gly
1               5                   10                  15

Gly Thr Val Thr Ile Asp Cys Gln Ala Ser Glu Ser Val Tyr Ser Asn
            20                  25                  30

```
Asn Arg Cys Ala Trp Tyr Gln Gln Lys Pro Gly Gln Pro Lys Leu
            35                  40                  45

Leu Ile Tyr Tyr Ala Ser Thr Leu Ala Ser Gly Val Pro Ser Arg Phe
 50                  55                  60

Lys Cys Ser Gly Ser Gly Thr Arg Phe Thr Leu Thr Ile Ser Gly Val
 65                  70                  75                  80

Gln Cys Glu Asp Ala Ala Thr Tyr Tyr Cys Ala Gly Tyr Lys Thr Ala
                 85                  90                  95

Asp Ser Asp Gly Leu Gly Phe Gly Gly Gly Thr Glu Val Glu Ile Lys
            100                 105                 110
```

<210> SEQ ID NO 169
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 169

```
Glu Gln Ser Val Lys Glu Ser Glu Gly Asp Leu Val Lys Pro Glu Gly
 1               5                  10                  15

Ser Leu Thr Leu Ala Cys Thr Ala Ser Gly Phe Thr Leu Ser Ser Tyr
             20                  25                  30

Tyr Met Cys Trp Val Arg Gln Ala Pro Gly Lys Gly Leu Glu Trp Ile
         35                  40                  45

Ala Cys Ile Asp Thr Asp Asn Asp Ile Arg Thr Ala Tyr Ala Ser Trp
     50                  55                  60

Ala Arg Gly Arg Phe Thr Ile Ser Arg Thr Ser Thr Thr Val Thr
 65                  70                  75                  80

Leu Gln Met Thr Ser Leu Thr Ala Ala Asp Thr Ala Thr Tyr Phe Cys
                 85                  90                  95

Gly Arg Gly Tyr Gly Ala Leu Arg Leu Asp Leu Trp Gly Gln Gly Thr
            100                 105                 110

Leu Val Thr Ile Ser Ser
        115
```

<210> SEQ ID NO 170
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 170

```
Glu Leu Asp Leu Thr Gln Thr Pro Ala Ser Val Ser Ala Ala Val Gly
 1               5                  10                  15

Gly Thr Val Ser Ile Asn Cys Gln Ser Ser Pro Ser Val Tyr Arg His
             20                  25                  30

Tyr Leu Ser Trp Tyr Gln Gln Lys Pro Gly Gln Pro Pro Lys Leu Leu
         35                  40                  45

Ile Tyr Trp Ala Ser Thr Leu Ala Ser Gly Val Pro Ser Arg Phe Ser
     50                  55                  60

Gly Ser Gly Ser Gly Thr Glu Phe Thr Leu Thr Ile Ser Gly Val Gln
 65                  70                  75                  80

Cys Asp Asp Ala Ala Thr Tyr Tyr Cys Ala Gly Glu Tyr Ala Ser Asp
                 85                  90                  95

Ser Asp Asn His Phe Gly Gly Gly Thr Glu Val Glu Ile Lys
            100                 105                 110
```

<210> SEQ ID NO 171
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 171

```
Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Ser Tyr His
            20                  25                  30

Met Gly Trp Val Arg Gln Ala Pro Gly Lys Gly Leu Glu Tyr Ile Gly
        35                  40                  45

Ile Ile Asn Asn Tyr Gly Ala Thr Tyr Tyr Ala Ser Trp Ala Lys Gly
    50                  55                  60

Arg Phe Thr Ile Ser Arg Thr Ser Thr Val Asp Leu Lys Met Thr
65                  70                  75                  80

Ser Leu Thr Thr Glu Asp Thr Ala Thr Tyr Phe Cys Ala Arg Ser Pro
                85                  90                  95

Gly Ile Pro Gly Tyr Asn Ser Trp Gly Pro Gly Thr Leu Val Thr Ile
            100                 105                 110

Ser Ser
```

<210> SEQ ID NO 172
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 172

```
Glu Leu Asp Leu Thr Gln Thr Pro Ser Ser Thr Ser Ala Ala Val Gly
1               5                   10                  15

Gly Thr Val Thr Ile Asn Cys Gln Ser Ser Gln Asn Val Tyr Ser Tyr
            20                  25                  30

Asn Arg Leu Ser Trp Phe Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Gly Tyr Asp Cys
                85                  90                  95

Arg Ser Ser Asp Cys Asp Ala Phe Gly Gly Thr Glu Val Glu Ile
            100                 105                 110

Lys
```

<210> SEQ ID NO 173
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 173

```
Ser Ser Ser Val Glu Glu Ser Gly Gly Asp Leu Val Lys Pro Gly Ala
1               5                   10                  15
```

```
Ser Leu Thr Leu Thr Cys Thr Ala Ser Gly Phe Ser Phe Ser Ser Asn
         20                  25                  30

Ser Met Cys Trp Val Arg Gln Ala Pro Gly Lys Gly Leu Glu Trp Ile
         35                  40                  45

Gly Cys Ile Ala Ser Ser Ser His Ser Thr Tyr Tyr Ala Ser Trp
 50                  55                  60

Ala Lys Gly Arg Phe Thr Ile Ser Lys Thr Ser Thr Thr Val Thr
 65                  70                  75                  80

Leu Gln Met Thr Ser Leu Thr Ala Ala Asp Met Ala Thr Tyr Phe Cys
             85                  90                  95

Ala Arg Asp Ser Gly Asn Arg Gly Tyr Leu Tyr Ala Gly Asp Phe Asn
             100                 105                 110

Leu Trp Gly Pro Gly Thr Leu Val Thr Val Ser Ser
             115                 120
```

<210> SEQ ID NO 174
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 174

```
Glu Leu Val Leu Thr Gln Thr Pro Ala Ser Val Glu Val Ala Val Gly
 1               5                  10                  15

Gly Thr Val Thr Ile Asn Cys Gln Ala Ser Gln Ser Ile Asn Ser Trp
             20                  25                  30

Leu Ser Trp Tyr Gln Gln Lys Pro Gly Gln Arg Pro Lys Leu Leu Ile
             35                  40                  45

Tyr Glu Ala Ser Thr Leu Ala Ser Gly Val Ser Ser Arg Phe Ser Gly
 50                  55                  60

Ser Gly Ser Gly Thr Gln Phe Thr Leu Thr Ile Ser Gly Val Gln Cys
 65                  70                  75                  80

Asp Asp Ala Ala Thr Tyr Tyr Cys Gln Gln Gly Tyr Ser Tyr Ser Asn
             85                  90                  95

Val Asp Asn Asn Ile Phe Gly Gly Gly Thr Glu Val Val Val Lys
             100                 105                 110
```

<210> SEQ ID NO 175
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 175

```
Gln Ser Leu Glu Glu Ser Gly Gly Gly Leu Val Lys Pro Glu Gly Ser
 1               5                  10                  15

Leu Thr Leu Thr Cys Thr Ala Ser Gly Phe Asp Leu Ser Ser Tyr
         20                  25                  30

Tyr Met Cys Trp Val Arg Gln Ala Pro Gly Lys Gly Leu Glu Trp Ile
         35                  40                  45

Val Cys Ile Asp Gly Gly Gly Glu Pro Thr Ala Tyr Pro Ser Trp
 50                  55                  60

Ala Lys Gly Arg Phe Thr Val Ser Lys Thr Ser Thr Thr Val Thr
 65                  70                  75                  80

Leu Gln Met Thr Ser Leu Thr Val Ala Asp Thr Ala Thr Tyr Phe Cys
```

```
                    85                  90                  95

Ala Arg Arg Asp Ala Gly Ala Gly Asn Ala Phe Ser Leu Trp Gly Pro
                100                 105                 110

Gly Thr Leu Val Thr Ile Ser Ser
            115                 120

<210> SEQ ID NO 176
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 176

Glu Leu Asp Met Thr Gln Thr Pro Ser Pro Val Ser Ala Ala Val Gly
1               5                   10                  15

Gly Thr Val Thr Ile Ser Cys Gln Ser Ser Gln Ser Val Tyr Leu Gln
            20                  25                  30

Asn Asn Leu Ala Trp Tyr Gln Gln Lys Pro Gly Gln Pro Pro Lys Leu
        35                  40                  45

Leu Ile Tyr Tyr Ala Ser Thr Leu Ala Ser Gly Val Ser Ser Arg Phe
50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Gly Tyr Ser Gly
                85                  90                  95

Tyr Ile Asn Ser Phe Gly Gly Gly Thr Glu Val Glu Ile Lys
                100                 105                 110

<210> SEQ ID NO 177
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 177

Gln Ser Val Lys Glu Ser Glu Gly Asp Leu Val Lys Pro Gly Ala Ser
1               5                   10                  15

Leu Thr Leu Thr Cys Lys Ala Ser Gly Phe Asp Phe Ser Ser Ser Tyr
            20                  25                  30

Phe Met Cys Trp Val Arg Gln Ala Pro Gly Arg Gly Leu Glu Trp Ile
        35                  40                  45

Ala Cys Ile Tyr Thr Val Ile Ser Arg Lys Thr Tyr Tyr Ala Ser Trp
50                  55                  60

Ala Lys Gly Arg Phe Thr Ile Ser Lys Thr Ser Ala Thr Thr Val Asp
65                  70                  75                  80

Leu Gln Met Thr Ser Leu Thr Ala Ala Asp Thr Ala Thr Tyr Phe Cys
                85                  90                  95

Ala Arg Ser Ala Thr Ile Glu Arg Leu Asp Leu Trp Gly Gln Gly Thr
                100                 105                 110

Leu Val Thr Val Ser Ser
            115

<210> SEQ ID NO 178
<211> LENGTH: 112
<212> TYPE: PRT
<213> ORGANISM: Artificial sequence
<220> FEATURE:
```

<223> OTHER INFORMATION: Synthetic polypeptide

<400> SEQUENCE: 178

```
Glu Leu Asp Leu Thr Gln Thr Pro Ser Pro Val Ser Ala Pro Val Gly
1               5                   10                  15

Gly Thr Val Thr Ile Asn Cys Gln Ala Ser Glu Ser Val Tyr Asn Asn
            20                  25                  30

Tyr Arg Leu Ser Trp Tyr Gln Gln Lys Pro Gly Gln Pro Pro Lys Leu
        35                  40                  45

Leu Ile Tyr Ala Ala Ser Thr Leu Ala Ser Gly Val Pro Ser Arg Phe
    50                  55                  60

Lys Gly Ser Gly Ser Gly Thr Gln Phe Thr Leu Ala Ile Ser Asp Val
65                  70                  75                  80

Val Cys Asp Asp Ala Ala Thr Tyr Tyr Cys Val Gly Tyr Lys Ser Gly
                85                  90                  95

Tyr Ile Asp Ser Ile Pro Phe Gly Gly Gly Thr Glu Val Val Val Lys
            100                 105                 110
```

<210> SEQ ID NO 179
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 179

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Thr Ile Asn Asn Tyr Asn
            20                  25                  30

Ile Asn Trp Val Arg Gln Ala Pro Gly Lys Gly Leu Glu Trp Ile Ala
        35                  40                  45

Arg Ile Trp Asn Gly Asp Gly Ser Thr Tyr Tyr Ala Ser Trp Ala Lys
    50                  55                  60

Gly Arg Phe Thr Ile Ser Lys Thr Ser Ser Thr Val Thr Leu Gln
65                  70                  75                  80

Met Thr Ser Leu Thr Ala Ala Asp Thr Ala Thr Tyr Phe Cys Ala Arg
                85                  90                  95

Asn Phe Asn Leu Trp Gly Pro Gly Thr Leu Val Thr Ile Ser Ser
            100                 105                 110
```

<210> SEQ ID NO 180
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 180

```
Glu Leu Val Leu Thr Gln Thr Pro Ser Pro Val Ser Ala Ala Val Gly
1               5                   10                  15

Gly Thr Val Thr Ile Asn Cys Gln Ser Ser Ala Ser Val Tyr Ser Asn
            20                  25                  30

Asn Tyr Leu Ser Trp Phe Gln Gln Lys Pro Gly Gln Pro Pro Lys Pro
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
```

-continued

```
                65                  70                  75                  80
Gln Cys Asp Asp Ala Ala Thr Tyr Tyr Cys Ala Gly Asp Tyr Ser Ser
                    85                      90                  95

Ser Ser Asp Met Cys Ile Phe Gly Gly Gly Thr Glu Leu Glu Ile Lys
                100                 105                 110
```